United States Patent
Yahagi et al.

(10) Patent No.: US 10,241,406 B2
(45) Date of Patent: *Mar. 26, 2019

(54) RESIST COMPOSITION AND METHOD FOR FORMING RESIST PATTERN

(71) Applicant: TOKYO OHKA KOGYO CO., LTD., Kawasaki-shi (JP)

(72) Inventors: Masahito Yahagi, Kawasaki (JP); Issei Suzuki, Kawasaki (JP); Yuki Fukumura, Kawasaki (JP); Toshikazu Takayama, Kawasaki (JP); Takashi Kamizono, Kawasaki (JP); Tatsuya Fujii, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/629,035

(22) Filed: Jun. 21, 2017

(65) Prior Publication Data
US 2017/0371241 A1   Dec. 28, 2017

(30) Foreign Application Priority Data
Jun. 28, 2016 (JP) .................................. 2016-128091

(51) Int. Cl.
| G03F 7/004 | (2006.01) |
| G03F 7/038 | (2006.01) |
| G03F 7/039 | (2006.01) |
| C07C 307/02 | (2006.01) |
| C07C 309/06 | (2006.01) |
| C07C 309/07 | (2006.01) |

(52) U.S. Cl.
CPC ............ *G03F 7/039* (2013.01); *C07C 307/02* (2013.01); *C07C 309/06* (2013.01); *C07C 309/07* (2013.01); *G03F 7/0045* (2013.01); *G03F 7/0046* (2013.01); *G03F 7/038* (2013.01); *G03F 7/0382* (2013.01); *G03F 7/0392* (2013.01); *G03F 7/0397* (2013.01)

(58) Field of Classification Search
CPC ................................. G03F 7/038; G03F 7/039
See application file for complete search history.

(56) References Cited

U.S. PATENT DOCUMENTS

| 7,511,169 | B2 | 3/2009 | Ohsawa et al. | |
|---|---|---|---|---|
| 8,263,307 | B2 | 9/2012 | Irie et al. | |
| 8,765,354 | B2 | 7/2014 | Utsumi et al. | |
| 8,795,944 | B2 | 8/2014 | Saegusa et al. | |
| 2010/0113818 | A1 | 5/2010 | Oh et al. | |
| 2010/0129738 | A1* | 5/2010 | Takemura | C08F 220/30 430/5 |
| 2010/0285405 | A1* | 11/2010 | Shimokawa | G03F 7/0045 430/270.1 |
| 2012/0100486 | A1 | 4/2012 | Sageashi et al. | |
| 2013/0115554 | A1 | 5/2013 | Takaki et al. | |
| 2013/0143159 | A1 | 6/2013 | Iwashita et al. | |
| 2014/0093824 | A1* | 4/2014 | Kawana | G03F 7/0388 430/296 |
| 2015/0111157 | A1 | 4/2015 | Kato et al. | |
| 2015/0338743 | A1 | 11/2015 | Iwato | |
| 2016/0024005 | A1 | 1/2016 | Yokokawa et al. | |
| 2016/0202608 | A1* | 7/2016 | Namai | G03F 7/0045 430/270.1 |
| 2016/0363860 | A1 | 12/2016 | Hirayama et al. | |

(Continued)

FOREIGN PATENT DOCUMENTS

| JP | 2012-108182 A | * | 6/2012 |
| JP | B-5149236 | | 2/2013 |

(Continued)

OTHER PUBLICATIONS

English translation of JP, 2012-108182 A (2012) from machine translation from AIPN Japan Patent Office National Center for Industrial Property Information and Training, generated Jan. 4, 2018, 106 pages.*

(Continued)

*Primary Examiner* — Cynthia Hamilton
(74) *Attorney, Agent, or Firm* — Knobbe Martens Olson & Bear LLP

(57) ABSTRACT

A resist composition containing a resin component having a structural unit represented by general formula (a0-1), and a compound represented by general formula (b1). In general formula (a0-1), R is a hydrogen atom, an alkyl group, or a halogenated alkyl group. $Va^1$ is a divalent hydrocarbon group. $n_{a1}$ represents an integer of 0 to 2. $Ra'^{12}$ and $Ra'^{13}$ are a monovalent chain saturated hydrocarbon group having 1 to 10 carbon atoms or a hydrogen atom. $Ra'^{14}$ is a phenyl group, a naphthyl group, or an anthryl group. In general formula (b1), $R^{b1}$ represents a cyclic hydrocarbon group. $Y^{b1}$ represents a divalent linking group containing an ester bond. $V^{b1}$ represents an alkylene group, a fluorinated alkylene group, or a single bond. m is an integer of 1 or more, and $M^{m+}$ is an m-valent organic cation.

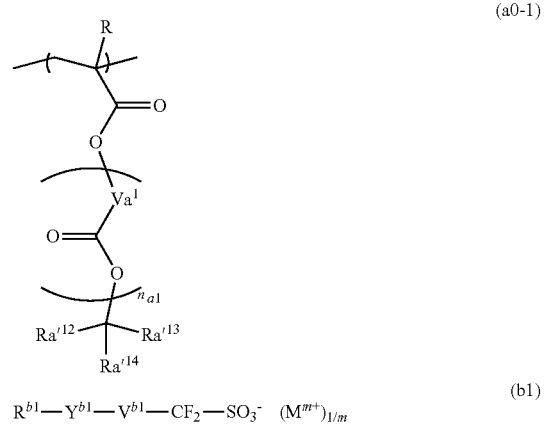

13 Claims, No Drawings

(56) References Cited

U.S. PATENT DOCUMENTS

2017/0184970 A1    6/2017  Goto et al.
2017/0369698 A1*  12/2017  Suzuki .................. C08L 51/08

FOREIGN PATENT DOCUMENTS

| JP | 2015-045702 A | 3/2015 |
| JP | 5692229 B | 4/2015 |
| WO | WO 2012/002470 A1 | 1/2012 |
| WO | WO-2015/046021 A1 * | 4/2015 |
| WO | WO 2015/133235 A1 | 9/2015 |

OTHER PUBLICATIONS

Office Action in U.S. Appl. No. 15/631,592, dated Apr. 2, 2018.
Final Office Action in U.S. Appl. No. 15/631,592, dated Sep. 18, 2018.

\* cited by examiner

RESIST COMPOSITION AND METHOD FOR FORMING RESIST PATTERN

BACKGROUND OF THE INVENTION

Field of the Invention

The present invention relates to a resist composition and a method for forming a resist pattern.

Priority of the present application is claimed based on Japanese Patent Application No. 2016-128091 filed on Jun. 28, 2016, the content of which is hereby incorporated by reference.

Background Art

A lithography technique includes steps of forming a resist film composed of a resist material on a substrate, selectively exposing the resist film and performing a developing treatment, thereby forming a resist pattern having a predetermined shape. A resist material in which an exposed area of the resist film is dissolved in a developing solution is referred to as a positive-type resist material, and a resist material in which an exposed area of the resist film is not dissolved in a developing solution is referred to as a negative-type resist material.

In recent years, in the manufacturing of semiconductor devices and liquid crystal display elements, pattern miniaturization has been rapidly progressed in accordance with the progress of the lithography technique. As a miniaturization technique, generally, shortening the wavelength (realizing high energy) of an exposure light source has been performed. Specifically, ultraviolet rays represented by a g-line and an i-line was used in the related art, but KrF excimer laser or ArF excimer laser has been used for the mass production of semiconductor devices these days. In addition, with such an excimer laser, studies regarding extreme ultraviolet rays (EUV) having a short wavelength (high energy), electron beams (EB), and an X-ray have been conducted.

The resist material is required to have lithography properties such as sensitivity with respect to the exposure light sources and resolution capable of reproducing patterns having a minute dimension.

In the related art, as a resist material satisfying such a requirement, a chemically amplified resist composition containing a base material component whose solubility in the developing solution changes under the action of an acid, and an acid generator component which generates an acid upon exposure has been used.

For example, in the case where the developing solution is an alkali developing solution (alkali developing process), a chemically amplified positive-type resist composition which contains a resin component (a base resin) whose solubility in the alkali developing solution increases under the action of the acid and an acid generator component is typically used. When a resist film formed by the aforementioned resist composition is selectively exposed to the light at the time of forming a resist pattern, an acid is generated in the exposed area from the acid generator component, the polarity of the base resin is increased under the action of the acid, and thereby the exposed area of the resist film becomes soluble in the alkali developing solution. For this reason, a positive-type pattern in which an unexposed area of the resist film remains as a pattern is formed by alkali developing.

On the other hand, in the case where such a chemically amplified resist composition is applied to a solvent developing process in which a developing solution (an organic developing solution) containing an organic solvent is used, the solubility in the organic developing solution is relatively decreased when the polarity of the base resin is increased, and thus the unexposed area of the resist film is dissolved and removed by the organic developing solution so as to form a negative-type resist pattern in which the exposed area of the resist film remains as a pattern. The solvent developing process in which such a negative-type resist pattern is formed is referred to as a negative-type developing process in some cases.

The base resin used for the chemically amplified resist composition generally has a plurality of structural units for improving the lithography properties.

For example, in the case of the resin component in which the solubility in the alkali developing solution is increased under the action of the acid, a structural unit including an acid-decomposable group which is decomposed by the action of an acid generated from the acid generator or the like so as to increase the polarity is used, and a structural unit including a lactone-containing cyclic group and a structural unit including a polar group such as a hydroxyl group are also used in combination.

In addition, in the forming of the resist pattern, behavior of the acid generated from the acid generator component upon exposure is regarded as one element that greatly affects lithography properties.

As an acid generator used in the chemically amplified resist composition, various kinds of acid generators have been proposed. For example, an onium salt-based acid generator such as an iodonium salt and a sulfonium salt, an oxime sulfonate-based acid generator, a diazomethane-based acid generator, a nitrobenzylsulfonate-based acid generator, an iminosulfonate-based acid generator, and a disulfone-based acid generator have been known.

As the onium salt-based acid generator, those containing an onium ion such as triphenylsulfonium in a cation part are mainly used. In an anion part of the onium salt-based acid generator, an alkylsulfonic acid ion or a fluorinated alkylsulfonic acid ion in which at least one hydrogen atom of an alkyl group is substituted with a fluorine atom is generally used.

In addition, in order to improve the lithography properties in the forming of the resist pattern, as the anion part of the onium salt-based acid generator, an onium salt-based acid generator which contains an anion having a specific structure containing an aromatic ring also has been proposed (for example, refer to Japanese Patent No. 5149236).

SUMMARY OF THE INVENTION

As the lithography technique further progresses and the miniaturization of the resist pattern progresses more and more, for example, a target of the lithography performed by electron beams and EUV is to form fine resist patterns of several tens of nanometers. As such, as the resist pattern dimension is small, the resist composition requires high sensitivity, and the lithography properties such as reduced roughness with respect to an exposure light source.

However, in the resist composition containing the onium salt-based acid generator in the related art as described above, when high sensitivity with respect to the exposure light source such as EUV is realized, it is less likely to obtain a desired resist pattern shape, and it is difficult to satisfy any properties described above.

The present invention has been made in consideration of the above-described circumstance, and an object thereof is to provide a resist composition which is capable of forming an excellent shaped resist pattern with high sensitivity and improved lithography properties, and a method for forming a resist pattern.

In order to solve the above-described problems, the present invention employs the following configurations.

That is, according to a first aspect of the present invention, there is provided a resist composition which generates an acid upon exposure and whose solubility in a developing solution changes under the action of the acid, the resist composition containing a base material component (A) which changes a solubility in a developing solution under the action of an acid and contains a resin component (A1) having a structural unit (a0) represented by general formula (a0-1), and an acid generator component (B) which generates an acid upon exposure and contains a compound (B1) represented by general formula (b1).

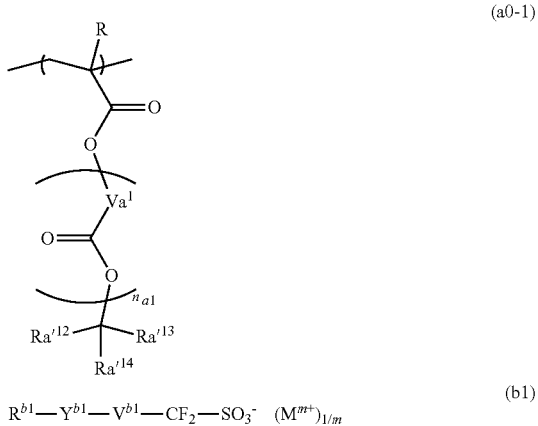

(a0-1)

$R^{b1}-Y^{b1}-V^{b1}-CF_2-SO_3^-$  $(M^{m+})_{1/m}$  (b1)

In general formula (a0-1), R represents a hydrogen atom, an alkyl group having 1 to 5 carbon atoms, or a halogenated alkyl group having 1 to 5 carbon atoms. $Va^1$ is a divalent hydrocarbon group which may have an ether bond. $n_{a1}$ represents an integer of 0 to 2. $Ra'^{12}$ and $Ra'^{13}$ each independently represent a monovalent chain saturated hydrocarbon group having 1 to 10 carbon atoms or a hydrogen atom. At least one hydrogen atom of the chain saturated hydrocarbon group may be substituted. $Ra'^{14}$ represents a phenyl group which may have a substituent, a naphthyl group which may have a substituent, or an anthryl group which may have a substituent. In general formula (b1), $R^{b1}$ represents a cyclic hydrocarbon group which may have a substituent. $Y^{b1}$ represents a divalent linking group containing an ester bond (—C(=O)—O— or —O—C(=O)—). $V^{b1}$ represents an alkylene group, a fluorinated alkylene group, or a single bond. m is an integer of 1 or more, and $M^{m+}$ is an m-valent organic cation.

According to a second aspect of the present invention, there is provided a method for forming a resist pattern, including forming a resist film on a support by using a resist composition according to the first aspect, exposing the resist film, and a step of forming a resist pattern by developing the exposed resist film.

According to the present invention, it is possible to provide a resist composition which is capable of forming an excellent shaped resist pattern with high sensitivity and improved lithography properties, and a method for forming a resist pattern.

DETAILED DESCRIPTION OF THE INVENTION

In the specification and claims of the present application, "aliphatic" is a relative concept with respect to aromatics, and is defined as a group, a compound, or the like having no aromaticity.

"Alkyl group" is assumed to contain a linear, branched, or cyclic monovalent saturated hydrocarbon group unless otherwise noted. The same is true for an alkyl group in an alkoxy group.

"Alkylene group" is assumed to contain a linear, branched, and cyclic divalent saturated hydrocarbon group unless otherwise noted.

"Halogenated alkyl group" is a group obtained by substituting at least one hydrogen atom of an alkyl group with a halogen atom, and examples of the halogen atom include a fluorine atom, a chlorine atom, a bromine atom, and an iodine atom.

"Fluorinated alkyl group" or "fluorinated alkylene group" means a group obtained by substituting at least one hydrogen atom of an alkyl group or an alkylene group with a fluorine atom.

"Structural unit" means a monomer unit constituting a polymer compound (a resin, a polymer, or a copolymer).

The phrase "may have a substituent" means both the case of substituting a hydrogen atom (—H) with a monovalent group and the case of substituting a methylene group (—CH$_2$—) with a divalent group.

"Exposure" is a concept including radiation irradiation in general.

"Structural unit derived from acrylic ester" means a structural unit formed by cleavage of an ethylenic double bond of the acrylic ester.

"Acrylic ester" is a compound obtained by substituting a hydrogen atom at a carboxy group terminal of an acrylic acid (CH$_2$=CH—COOH) with an organic group.

The acrylic ester may be obtained by substituting a hydrogen atom bonded to an α-position carbon atom with a substituent. The substituent ($R^{\alpha 0}$) with which the hydrogen atom bonded to the α-position carbon atom is substituted is an atom other than the hydrogen atom or a group, and examples thereof include an alkyl group having 1 to 5 carbon atoms and a halogenated alkyl group having 1 to 5 carbon atoms. In addition, it is assumed that the acrylic ester includes itaconic acid diester obtained by substituting the substituent ($R^{\alpha 0}$) with a substituent containing an ester bond, and α-hydroxyacrylic ester obtained by substituting the substituent ($R^{\alpha 0}$) with a group modified with a hydroxyalkyl group or a hydroxyl group thereof. Note that, the α-position carbon atom of the acrylic ester is a carbon atom to which a carbonyl group of an acrylic acid is bonded unless otherwise noted.

Hereinafter, acrylic ester obtained by substituting the hydrogen atom bonded to a α-position carbon atom with a substituent may be referred to as α-substituted acrylic ester. In addition, both of the acrylic ester and the α-substituted acrylic ester may be referred to as "(α-substituted) acrylic ester".

"Structural unit derived from acrylamide" means a structural unit formed by cleavage of an ethylenic double bond of the acrylamide.

The acrylamide may be obtained by substituting a hydrogen atom bonded to a α-position carbon atom with a substituent or may be obtained by substituting one or both of hydrogen atoms of an amino group of acrylamide with a substituent. Note that the α-position carbon atom of the acrylamide is a carbon atom to which a carbonyl group of acrylamide is bonded unless otherwise noted.

As the substituent with which a hydrogen atom bonded to the α-position carbon atom of the acrylamide is substituted, the same substituent as that (substituent ($R^{\alpha 0}$)) exemplified as a α-position substituent in the α-substituted acrylic ester can be used.

"Structural unit derived from hydroxystyrene" means a structural unit formed by cleavage of an ethylenic double bond of hydroxystyrene. "Structural unit derived from a hydroxystyrene derivative" means a structural unit formed by cleavage of an ethylenic double bond of a hydroxystyrene derivative.

"Hydroxystyrene derivative" includes those obtained by substituting an α-position hydrogen atom of hydroxystyrene with other substituents such as an alkyl group and a halogenated alkyl group, and derivatives thereof. Examples of the derivatives include a derivative obtained by substituting a hydrogen atom of a hydroxyl group of hydroxystyrene in which the α-position hydrogen atom may be substituted with a substituent with an organic group; and a derivative in which a substituent other than the hydroxyl group is bonded to a benzene ring of hydroxystyrene in which α-position hydrogen atom may be substituted with a substituent. Here, the α-position (α-position carbon atom) means a carbon atom to which a benzene ring is bonded unless otherwise noted.

As the substituent with which the α-position hydrogen atom of the hydroxystyrene is substituted, the same substituent as that exemplified as a α-position substituent in the α-substituted acrylic ester can be used.

"Structural unit derived from a vinylbenzoic acid derivative or a vinylbenzoic acid derivative" means a structural unit formed by cleavage of an ethylenic double bond of a vinylbenzoic acid or a vinylbenzoic acid derivative.

"Vinylbenzoic acid derivative" includes those obtained by substituting an α-position hydrogen atom of a vinylbenzoic acid with other substituents such as an alkyl group and a halogenated alkyl group, and derivatives thereof. Examples of the derivatives include a derivative obtained by substituting a hydrogen atom of a carboxy group of the vinylbenzoic acid in which the α-position hydrogen atom may be substituted with a substituent with an organic group; and a derivative in which a substituent other than the hydroxyl group and the carboxy group is bonded to a benzene ring of the vinylbenzoic acid in which α-position hydrogen atom may be substituted with a substituent. Here, the α-position (α-position carbon atom) means a carbon atom to which a benzene ring is bonded unless otherwise noted.

"Styrene" is a concept including styrene and those obtained by substituting an α-position hydrogen atom of the styrene with other substituents other than an alkyl group and a halogenated alkyl group.

"Styrene derivative" is a concept including those obtained by substituting the α-position hydrogen atom of the styrene with other substituents such as an alkyl group and a halogenated alkyl group, and the derivatives thereof. Examples of the derivatives include a derivative in which a substituent is bonded to a benzene ring of hydroxystyrene in which the α-position hydrogen atom may be substituted with a substituent. Here, the α-position (α-position carbon atom) means a carbon atom to which a benzene ring is bonded unless otherwise noted.

"Structural unit derived from the styrene" and "structural unit derived from the styrene derivative" mean structural units formed by cleavage of an ethylenic double bond of the styrene or the styrene derivative.

The alkyl group as the α-position substituent is preferably a linear or branched alkyl group, and specifically, examples thereof include an alkyl group having 1 to 5 carbon atoms (a methyl group, an ethyl group, a propyl group, an isopropyl group, an n-butyl group, an isobutyl group, a tert-butyl group, a pentyl group, an isopentyl group, and a neopentyl group).

In addition, specific examples of the halogenated alkyl group as the α-position substituent include a group obtained by substituting at least one hydrogen atom of "the alkyl group as the α-position substituent" with a halogen atom. Examples of the halogen atom include a fluorine atom, a chlorine atom, a bromine atom, and an iodine atom, and particularly, a fluorine atom is preferable.

Further, specific examples of the hydroxyalkyl group as the α-position substituent include a group obtained by substituting at least one hydrogen atom of the "alkyl group as the α-position substituent" with a hydroxyl group. The number of the hydroxyl groups in the hydroxyalkyl group is preferably 1 to 5, and is most preferably 1.

Resist Composition

According to the first aspect of the present invention, in a resist composition, an acid is generated upon exposure, and the solubility in a developing solution is changed under the action of the acid.

As one embodiment of the resist composition, there is provided a resist composition which contains a base material component (A) (hereinafter, also referred to as "(A) component") whose solubility in the developing solution changes under the action of an acid, and an acid generator component (B) (hereinafter, also referred to as "(B) component") which generates an acid upon exposure. In the resist composition of the present embodiment, the (A) component contains a resin component (A1) (hereinafter, also referred to as "(A1) component") having a structural unit (a0) represented by general formula (a0-1), and the (B) component contains a compound (B1) represented by general formula (b1).

When a resist film is formed by using the resist composition of the present embodiment, and the resist film is selectively exposed to the light, an acid is generated from the (B) component in the exposed area of the resist film, and the solubility of the (A) component in the developing solution changes under the action of the acid; on the other hand, in the unexposed area of the resist film, the solubility of the (A) component in the developing solution does not change. Therefore, a difference in the solubility in the developing solution occurs between the exposed area and the unexposed area. For this reason, when the resist film is developed, in the case where the resist composition is a positive-type, the exposed area of the resist film is dissolved and removed so as to form a positive-type resist pattern, and in the case where the resist composition is a negative-type, the unexposed area of the resist film is dissolved and removed so as to form a negative-type resist pattern.

In the present specification, the resist composition with which the exposed area of the resist film is dissolved and removed so as to form the positive-type resist pattern is referred to as a positive-type resist composition, and the resist composition with which the unexposed area of the resist film is dissolved and removed so as to form a negative-type resist pattern is referred to as a negative-type resist composition.

The resist composition of the present embodiment may be a positive-type resist composition, or may be a negative-type resist composition.

Further, the resist composition of the present embodiment may be used for an alkali developing process in which an alkali developing solution is used for a developing treatment at the time of forming a resist pattern, or may be used for a solvent developing process in which a developing solution (an organic developing solution) containing an organic solvent is used for the developing treatment.

The resist composition of the present embodiment has an acid generating ability to generate an acid upon exposure, and in addition to the (B) component, the (A) component also may generate an acid upon exposure.

In the case where the (A) component generates an acid upon exposure, the (A) component is "a base material component which generates an acid upon exposure and whose solubility in the developing solution changes under the action of the acid". In the case where the (A) component is the base material component which generates an acid upon exposure and whose solubility in the developing solution changes under the action of the acid, a (A1) component described below is preferably a polymer compound which generates an acid upon exposure and changes the solubility in a developing solution under the action of the acid. Examples of such a polymer compound include a resin having a structural unit which generates an acid upon exposure. As a monomer deriving the structural unit which generates an acid upon exposure, well-known structural units can be used.

Component (A)

The (A) component is a base material component whose solubility in a developing solution changes under the action of an acid.

The "base material component" in the present invention is an organic compound having film-forming ability, and is preferably an organic compound having a molecular weight of 500 or more. When the molecular weight of the organic compound is 500 or more, the film-forming ability is improved, and a resist pattern at a nano level is easily formed.

The organic compound used as a base material component is generally classified into a non-polymer and a polymer.

Generally, a non-polymer having a molecular weight of 500 or more and less than 4,000 is used as the non-polymer. Hereinafter, a non-polymer having a molecular weight of 500 or more and less than 4,000 is referred to as "low molecule compound".

Generally, a polymer having a molecular weight of 1,000 or more is used. Hereinafter, a polymer having a molecular weight of 1,000 or more is referred to as "resin", "polymer compound", or "polymer".

As the molecular weight of the polymer, the mass average molecular weight expressed in terms of polystyrene by gel permeation chromatography (GPC) is used.

As the (A) component used for the resist composition of the present embodiment, at least a (A1) component is used, and the (A1) component and other polymer compounds and/or a low molecule compound are may be used in combination.

In the resist composition of the present embodiment, the (A) component contains the resin component (A1) having structural unit (a0) represented by general formula (a0-1).

In the case where the resist film formed by using the resist composition containing the (A1) component is exposed, the structural unit (a0) is exposed to the light, at least a portion of bonds of the structural unit (a0) is cleaved under the action of the acid, and thus the polarity is increased in the resist film. For this reason, the resist composition of the present embodiment becomes a negative-type in the case where the developing solution is an organic developing solution (solvent developing process), negative-type developing process, and becomes a positive-type in the case where the developing solution is an alkaline developing solution (alkali developing process). As such, the polarity of the (A1) component is changed before and after the exposure, and thus when the (A1) component is used, it is possible to obtain satisfactory development contrast not only in the alkali developing process, but also in the solvent developing process. Therefore, the resist composition of the present aspect is the positive-type in the alkali developing process, and is the negative-type in the solvent developing process.

That is, in the case of the alkali developing process, the (A1) component has the sparing solubility in the alkali developing solution before exposure, and for example, when an acid is generated from the (B) component upon exposure, the polarity is increased under the action of the acid and thus the solubility in the alkali developing solution is increased. For this reason, in the forming of the resist pattern, when the resist film obtained by coating the support with the resist composition is selectively exposed to the light, the sparing solubility of the exposed area of the resist film is changed to be soluble in the alkali developing solution; on the other hand, the solubility of the unexposed area of the resist film remains to be alkali sparing solubility without being changed, and thus the positive-type resist pattern is formed by the alkali developing the resist film.

On the other hand, in the case of the solvent developing process, the (A1) component has the solubility increased in the organic developing solution before exposure, and when the acid is generated from the (B) component upon exposure, the polarity is increased under the action of the acid, and thus the solubility in the organic developing solution is decreased. For this reason, in the forming of the resist pattern, when the resist film obtained by coating the support with the resist composition is selectively exposed to the light, the solubility of the exposed area of the resist film is changed to the sparing solubility in the organic developing solution; on the other hand, the solubility of the unexposed area of the resist film is not changed, and thus it is possible to impart contrast between the exposed area and unexposed area by developing the resist film with the organic developing solution, thereby forming the negative-type resist pattern.

Regarding (A1) Component

The (A1) component is a resin component having a structural unit (a0).

In addition to the structural unit (a0), a resin component having a structural unit (a2) containing a lactone-containing cyclic group, a —$SO_2$— containing cyclic group or a carbonate-containing cyclic group is preferable as the (A1) component.

Further, in addition to the structural unit (a0), or the structural unit (a0) and the structural unit (a2), a resin component having a structural unit (a9) represented by general formula (a9-1) is also preferable as the (A1) component.

Further, in addition to the structural unit (a0), a resin component having a structural unit which contains a hydroxystyrene skeleton is also preferable as the (A1) component.

Further, the (A1) component may have any structural unit other than the structural units (a0), (a2), and (a9), and the structural unit containing the hydroxystyrene skeleton.

Structural Unit (a0)

The structural unit (a0) is a structural unit represented by general formula (a0-1).

The structural unit (a0) contains an acid-decomposable group in which the polarity is increased under the action of the acid. The "acid-decomposable group" is a group having the acid decomposability with which at least a portion of the bonds in the structure of the acid-decomposable group can be cleaved under the action of the acid. In the structural unit (a0), a bond between the acid dissociable group (—C(Ra'$^{12}$) (Ra'$^{13}$) (Ra'$^{14}$)) and an oxygen atom adjacent to the acid dissociable group is cleaved under the action of the acid, and a polar group (carboxy group) having high polarity is generated so as to increase the polarity.

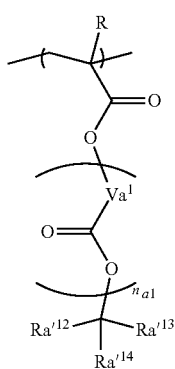

(a0-1)

In the formula, R represents a hydrogen atom, an alkyl group having 1 to 5 carbon atoms, or a halogenated alkyl group having 1 to 5 carbon atoms. Va$^1$ represents a divalent hydrocarbon group which may have an ether bond. $n_{a1}$ represents an integer of 0 to 2. Ra'$^{12}$ and Ra'$^{13}$ each independently represent a monovalent chain saturated hydrocarbon group having 1 to 10 carbon atoms or a hydrogen atom. At least one hydrogen atom of the chain saturated hydrocarbon group may be substituted. Ra'$^{14}$ represents a phenyl group which may have a substituent, a naphthyl group which may have a substituent, or an anthryl group which may have a substituent.

In general formula (a0-1), R represents a hydrogen atom, an alkyl group having 1 to 5 carbon atoms, or a halogenated alkyl group having 1 to 5 carbon atoms.

The alkyl group having 1 to 5 carbon atoms for R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group obtained by substituting at least one hydrogen atom of an alkyl group having 1 to 5 carbon atoms with a halogen atom. Examples of the halogen atom include a fluorine atom, a chlorine atom, a bromine atom, and an iodine atom, and particularly, a fluorine atom is preferable.

R is preferably a hydrogen atom, an alkyl group having 1 to 5 carbon atoms, or a fluorinated alkyl group having 1 to 5 carbon atoms, and a hydrogen atom or a methyl group is particularly preferable in terms of industrial availability.

In general formula (a0-1), Va$^1$ is a divalent hydrocarbon group which may have an ether bond.

A divalent hydrocarbon group for Va$^1$ may be an aliphatic hydrocarbon group, or may be an aromatic hydrocarbon group.

An aliphatic hydrocarbon group as the divalent hydrocarbon group Va$^1$ may be saturated or unsaturated, and is usually preferably saturated.

More specifically, examples of the aliphatic hydrocarbon group include a linear or branched aliphatic hydrocarbon group, or an aliphatic hydrocarbon group containing a ring in the structure.

The number of carbon atoms of the linear aliphatic hydrocarbon group is preferably 1 to 10, is further preferably 1 to 6, is further still preferably 1 to 4, and is most preferably 1 to 3.

As the linear aliphatic hydrocarbon group, the linear alkylene group is preferable, and specifically, a methylene group [—CH$_2$—], an ethylene group [—(CH$_2$)$_2$—], a trimethylene group [—(CH$_2$)$_3$—], a tetramethylene group [—(CH$_2$)$_4$—], and a pentamethylene group [—(CH$_2$)$_5$—].

The number of carbon atoms of the branched aliphatic hydrocarbon group is preferably 3 to 10, is still preferably 3 to 6, is still further preferably 3 or 4, and is most preferably 3.

As the branched aliphatic hydrocarbon group, a branched alkylene group is preferable. Specifically, examples thereof include an alkyl alkylene group such as an alkyl methylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; an alkyl ethylene group such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; an alkyl trimethylene group such as —CH(CH$_3$)CH$_2$CH$_2$— and —CH$_2$CH(CH$_3$)CH$_2$—; an alkyl tetramethylene group such as —CH(CH$_3$)CH$_2$CH$_2$CH$_2$— and —CH$_2$CH(CH$_3$)CH$_2$CH$_2$—. The alkyl group in the alkyl alkylene group is preferably a linear alkyl group having 1 to 5 carbon atoms.

As the aliphatic hydrocarbon group containing a ring in the structure, an alicyclic hydrocarbon group (a group obtained by removing two hydrogen atoms from an aliphatic hydrocarbon ring), a group in which the alicyclic hydrocarbon group is bonded to a terminal of the linear or branched aliphatic hydrocarbon group, and a group in which the alicyclic hydrocarbon group is present in the middle of the linear or branched aliphatic hydrocarbon group. Examples of the linear or branched aliphatic hydrocarbon group include the same group as the linear aliphatic hydrocarbon group or the branched aliphatic hydrocarbon group the described above.

The number of carbon atoms of the alicyclic hydrocarbon group is preferably 3 to 20, and is further preferably 3 to 12.

The alicyclic hydrocarbon group may be a polycyclic group, and may be a monocyclic group. The monocyclic alicyclic hydrocarbon group is preferably a group obtained by removing two hydrogen atoms from the monocycloalkane. The number of the carbon atoms of the monocycloalkane is preferably 3 to 6, and specific examples thereof include cyclopentane and cyclohexane.

The polycyclic alicyclic hydrocarbon group is preferably a group obtained by removing two hydrogen atoms from the polycycloalkane, and the number of the carbon atoms of the polycycloalkane is preferably 7 to 12. Specific examples thereof include adamantane, norbornane, isobornane, tricyclodecane, and tetracyclododecane.

The aromatic hydrocarbon group as a divalent hydrocarbon group for Va$^1$ is a hydrocarbon group having an aromatic ring.

The number of carbon atoms of the aromatic hydrocarbon group is preferably 3 to 30, is further preferably 5 to 30, is still further preferable 5 to 20, is particularly, preferably 6 to 15, and is most preferably 6 to the steel pipe 10. Here, it is assumed that the number of carbon atoms does not include the number of carbon atoms in the substituent.

Specific examples of the aromatic ring having an aromatic hydrocarbon group include an aromatic hydrocarbon ring such as benzene, biphenyl, fluorene, naphthalene, anthracene, and phenanthrene; and aromatic heterocycle in which a portion of the carbon atoms which constitute the aromatic hydrocarbon ring is substituted with a heteroatom. Examples of the heteroatom in the aromatic heterocycle include an oxygen atom, a sulfur atom, and a nitrogen atom.

Specific examples of the aromatic hydrocarbon group include a group (an arylene group) obtained by removing two hydrogen atoms from the above-mentioned aromatic hydrocarbon ring; and a group in which one hydrogen atom of a group (an aryl group) obtained by removing one hydrogen atom from the above-mentioned aromatic hydrocarbon ring is substituted with an alkylene group (for example, a group obtained by removing one hydrogen atom from an aryl group in an aryl alkyl group, such as a benzyl group, a phenethyl group, a 1-naphthyl methyl group, a 2-naphthyl methyl group, a 1-naphthyl ethyl group, and a 2-naphthyl ethyl group). The number of carbon atoms of the alkylene group (an alkyl chain in the aryl alkyl group) is preferably 1 to 4, is further preferably 1 and 2, and is particularly preferably 1.

In general formula (a0-1), $n_{a1}$ is an integer 0 to 2, is preferably 0 or 1, and is further preferably 0.

In general formula (a0-1), $Ra'^{12}$ and $Ra'^{13}$ each independently represent a monovalent chain saturated hydrocarbon group having 1 to 10 carbon atoms or a hydrogen atom.

In $Ra'^{12}$ and $Ra'^{13}$, examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group. At least one hydrogen atom of the chain saturated hydrocarbon group may be substituted.

Among them, each of $Ra'^{12}$ and $Ra'^{13}$ is preferably a hydrogen atom and an alkyl group having 1 to 5 carbon atoms, is further preferably an alkyl group having 1 to 5 carbon atoms, is still further preferably a methyl group and an ethyl group, and is particularly preferably a methyl group.

In the case where a hydrogen atom of the chain saturated hydrocarbon group represented by $Ra'^{12}$ or $Ra'^{13}$ is substituted, examples of a substituent thereof include —$R^{P1}$, —$R^{P2}$—O—$R^{P1}$, —$R^{P2}$—CO—$R^{P1}$, —$R^{P2}$—CO—O$R^{P1}$, —$R^{P2}$—O—CO—$R^{P1}$, —$R^{P2}$—OH, —$R^{P2}$—CN or —$R^{P2}$—COOH (hereinafter, these substituents are collectively referred to "$Ra^{05}$")

Here, $R^{P1}$ is a monovalent chain saturated hydrocarbon group having 1 to 10 carbon atoms, monovalent aliphatic cyclic saturated hydrocarbon group having 3 to 20 carbon atoms, or monovalent aromatic hydrocarbon group having 6 to 30 carbon atoms.

In addition, $R^{P2}$ is a single bond, a divalent chain saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms. Here, at least one hydrogen atom of the chain saturated hydrocarbon group, the aliphatic cyclic saturated hydrocarbon group, or the aromatic hydrocarbon group of $R^{P1}$ and $R^{P2}$ may be substituted with a fluorine atom.

The above-described aliphatic cyclic saturated hydrocarbon group may have one or more same kinds of substituents described above, or may have one or more different kinds of substituents described above.

Examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; polycyclic aliphatic saturated hydrocarbon group such as a bicyclo [2.2.2]octanyl group, a tricyclo [5.2.1.02,6] decanyl group, a tricyclo [3.3.1.13,7] decanyl group, a tetracyclo [6.2.1.13, 6.02,7]dodecanyl group, and an adamantyl group.

Examples of the monovalent aromatic hydrocarbon group having 6 to 30 carbon atoms include a group obtained by removing one hydrogen atom from the aromatic hydrocarbon ring benzene, biphenyl, fluorene, naphthalene, anthracene, and phenanthrene.

In general formula (a0-1), $Ra'^{14}$ represents a phenyl group which may have a substituent, a naphthyl group which may have a substituent, or an anthryl group which may have a substituent. Among them, $Ra'^{14}$ is preferably a naphthyl group may have a substituent from the aspect that the effects of the present invention are further improved.

Examples of the substituent that $Ra'^{14}$ include a methyl group, an ethyl group, a propyl group, a hydroxyl group, a carboxyl group, and a halogen atom (a fluorine atom, a chlorine atom, and a bromine atom), an alkoxy group (such as a methoxy group, an ethoxy group, a propoxy group, and a butoxy group), and an alkyloxycarbonyl group.

In the case where $Ra'^{14}$ in general formula (a0-1) is a naphthyl group, in the acid dissociable group (—$C(Ra'^{12})$ $(Ra'^{13})$ $(Ra'^{14})$) in general formula (a0-1), a position which is bonded to a tertiary carbon atom may be 1-position and 2-position of a naphthyl group.

In the case where $Ra'^{14}$ in general formula (a0-1) is an anthryl group, in the acid dissociable group (—$C(Ra'^{12})$ $(Ra'^{13})$ $(Ra'^{14})$) in general formula (a0-1), a position which is bonded to a tertiary carbon atom may be 1-position, 2-position, or 9-position of an anthryl group.

Specific examples of the structural unit represented by general formula (a0-1) will be described below. In the respective formulae, $R^{\alpha}$ represents a hydrogen atom, a methyl group, or a trifluoromethyl group.

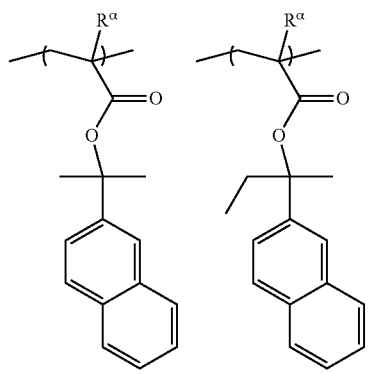

-continued

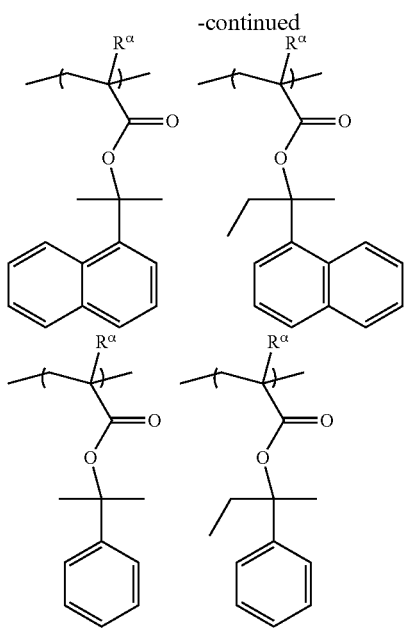

The structural unit (a0) of the (A1) component may be used alone, or two or more kinds thereof may be used in combination.

The ratio of the structural unit (a0) in the (A1) component is preferably 20 to 70 mol %, is further preferably 25 to 65 mol %, and is still further preferably 30 to 60 mol % with respect to the total (100 mol %) structural units for constituting the (A1) component.

When the ratio of the structural unit (a0) is set to be equal to or greater than the lower limit, it is possible to easily obtain a resist pattern, and thereby the lithography properties such as the sensitivity, the resolution, and the reduced roughness are also improved. On the other hand, when the ratio of the structural unit (a0) is set to be equal to or less than the upper limit value, it is possible to take balance with other structural units.

Structural Unit (a2)

The (A1) component preferably has a structural unit (a2) containing a lactone-containing cyclic group, a —SO$_2$— containing cyclic group or a carbonate-containing cyclic group in addition to the structural unit (a0).

In the case where the (A1) component is used for forming a resist film, the lactone-containing cyclic group, the —SO$_2$— containing cyclic group, or the carbonate-containing cyclic group of the structural unit (a2) is effective in improving the adhesiveness with respect to the substrate of the resist film. In addition, when the (A1) component has the structural unit (a2), the solubility of the resist film in alkali developing solution is increased at the time of developing in the alkali developing process.

The "lactone-containing cyclic group" means a cyclic group containing a ring (lactone ring) including —O—C(=O)— in the cyclic skeleton. When the lactone ring is counted as the first ring, if there is only the lactone ring, the cyclic group is referred to as a monocyclic group, and if there are other ring structures in addition to the lactone ring, the cyclic group is referred to as a polycyclic group regardless of its structure. The lactone-containing cyclic group may be a monocyclic group, or may be a polycyclic group.

The lactone-containing cyclic group in the structural unit (a2) is not particularly limited, and any lactone-containing cyclic group can be used. Specific examples thereof include groups respectively represented by general formulae (a2-r-1) to (a2-r-7).

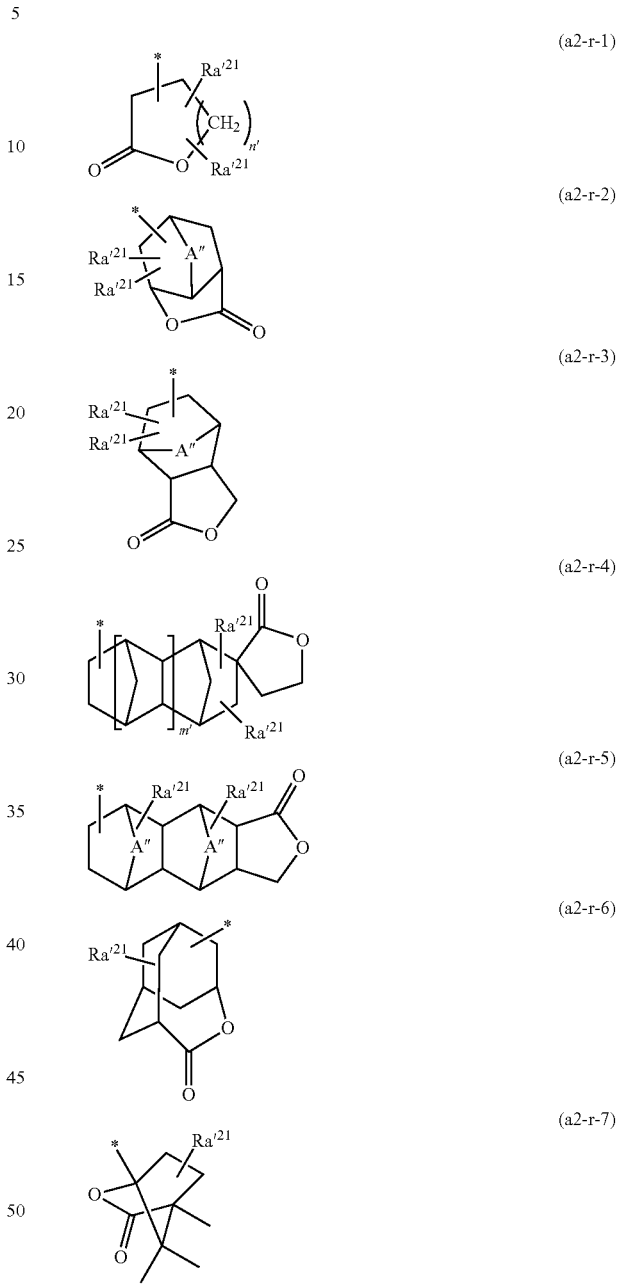

In the formula, Ra′$^{21}$'s each independently represent a hydrogen atom, an alkyl group, an alkoxy group, a halogen atom, a halogenated alkyl group, a hydroxyl group, —COOR″, —OC(=O)R″, a hydroxyalkyl group, or a cyano group; R″ is a hydrogen atom, an alkyl group, a lactone-containing cyclic group, a carbonate-containing cyclic group, or a —SO$_2$— containing cyclic group; A″ is an alkylene group having 1 to 5 carbon atoms, which may have an oxygen atom (—O—) or a sulfur atom (—S—), an oxygen atom, or a sulfur atom; n′ is an integer of 0 to 2; and m′ is an integer of 0 or 1.

In general formulae (a2-r-1) to (a2-r-7), the alkyl group for Ra′$^{21}$ is preferably an alkyl group having 1 to 6 carbon atoms. The alkyl group is preferably a linear or branched alkyl group. Specifically, examples thereof include a methyl group, an ethyl group, a propyl group, an isopropyl group, an n-butyl group, an isobutyl group, a tert-butyl group, a pentyl group, an isopentyl group, a neopentyl group, and a hexyl group. Among them, the methyl group or the ethyl group is preferable, and the methyl group is particularly preferable.

The alkoxy group for $Ra'^{21}$ is preferably an alkoxy group having 1 to 6 carbon atoms.

The alkoxy group is preferably a linear or branched alkoxy group. Specifically, examples thereof include a group in which the alkyl group exemplified as the alkyl group for $Ra'^{21}$ and an oxygen atom (—O—) are linked with each other.

Examples of the halogen atom for $Ra'^{21}$ include a fluorine atom, a chlorine atom, a bromine atom, and an iodine atom, and among them, the fluorine atom is preferable.

Examples of the halogenated alkyl group for $Ra'^{21}$ include a group obtained by substituting at least one hydrogen atom of the alkyl group for $Ra'^{21}$ with a halogen atom. The halogenated alkyl group is preferably a fluorinated alkyl group, and is particularly preferably a perfluoroalkyl group.

In —COOR" and —OC(=O)R" for $Ra'^{21}$, R"'s are a hydrogen atom, an alkyl group, a lactone-containing cyclic group, carbonate-containing cyclic group, or a —SO$_2$— containing cyclic group.

The alkyl group for R" may be a linear, branched, or cyclic alkyl group, and the number of carbon atoms thereof is preferably 1 to 15.

In the case where R" is a linear or branched alkyl group, the number of carbon atoms is preferably 1 to 10, and is further preferably 1 to 5. Particularly, a methyl group or an ethyl group is preferable.

In the case where R" is a cyclic alkyl group, the number of carbon atoms is preferably 3 to 15, is further preferably 4 to 12, and is most preferably 5 to 10. Specifically, examples of the cyclic alkyl group include a group obtained by removing one or more hydrogen atoms from monocycloalkane which may be or may be not substituted with a fluorine atom or a fluorinated alkyl group; and a group obtained by removing one or more hydrogen atoms from polycycloalkane such as bicycloalkane, tricycloalkane, and tetracycloalkane. More specifically, examples of the cyclic alkyl group include a group obtained by removing one or more hydrogen atoms from monocycloalkane such as cyclopentane and cyclohexane; and a group obtained by removing one or more hydrogen atoms from polycycloalkane such as adamantane, norbornane, isobornane, tricyclodecane, and tetracyclododecane.

Examples of the lactone-containing cyclic group for R" include the same groups which are represented by general formulae (a2-r-1) to (a2-r-7).

The carbonate-containing cyclic group for R" is the same as a carbonate-containing cyclic group described below, and specific examples thereof include the same groups which are represented by general formulae (ax3-r-1) to (ax3-r-3).

The —SO$_2$— containing cyclic group for R" is the same as a —SO$_2$— containing cyclic group described below, and specific examples thereof include the same groups which are represented by general formulae (a5-r-1) to (a5-r-4).

The hydroxyalkyl group for $Ra'^{21}$ is preferably a hydroxyalkyl group having 1 to 6 carbon atoms, and specific examples thereof include a group obtained by substituting at least one hydrogen atom of the alkyl group for $Ra'^{21}$ with a hydroxyl group.

In general formulae (a2-r-2), (a2-r-3), and (a2-r-5), the alkylene group having 1 to 5 carbon atoms for A" is preferably a linear or branched alkylene group, and examples thereof include a methylene group, an ethylene group, an n-propylene group, and an isopropylene group. In the case where the alkylene group contains an oxygen atom or a sulfur atom, specific examples thereof include a group in which —O— or —S— is present at a terminal of the alkylene group or between carbon atoms, and examples of the aforementioned group include —O—CH$_2$—, —CH$_2$—O—CH$_2$—, —S—CH$_2$—, and —CH$_2$—S—CH$_2$—. The A" is preferably an alkylene group having 1 to 5 carbon atoms or —O—, is further preferably an alkylene group having 1 to 5 carbon atoms, and is most preferably a methylene group.

Specific examples of the groups represented by general formulae (a2-r-1) to (a2-r-7) are described as follows.

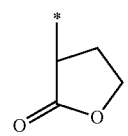

(r-lc-1-1)

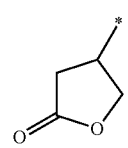

(r-lc-1-2)

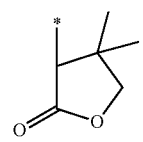

(r-lc-1-3)

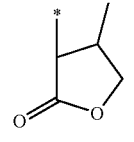

(r-lc-1-4)

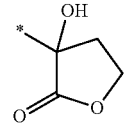

(r-lc-1-5)

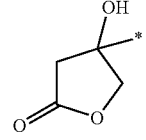

(r-lc-1-6)

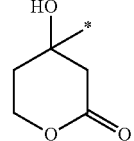

(r-lc-1-7)

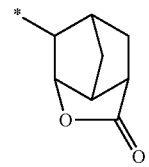

(r-lc-2-1)

-continued
(r-1c-2-2)
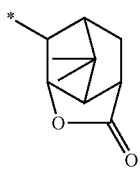
(r-1c-2-3)
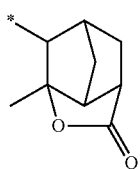
(r-1c-2-4)
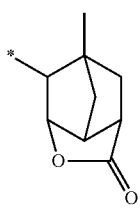
(r-1c-2-5)
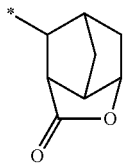
(r-1c-2-6)
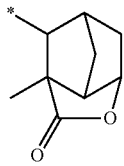
(r-1c-2-7)
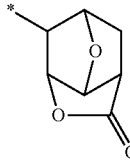
(r-1c-2-8)
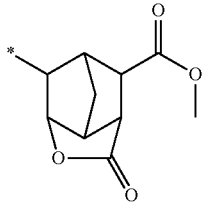
(r-1c-2-9)
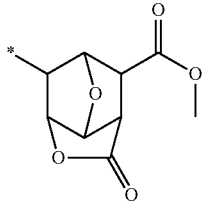
-continued
(r-lc-2-10)
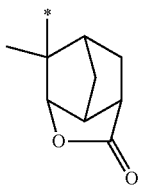
(r-lc-2-11)
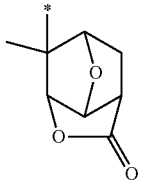
(r-lc-2-12)
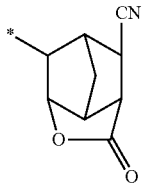
(r-lc-2-13)
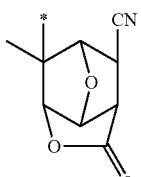
(r-lc-2-14)
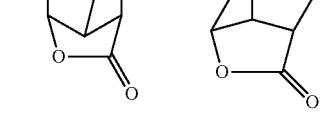
(r-lc-2-15)
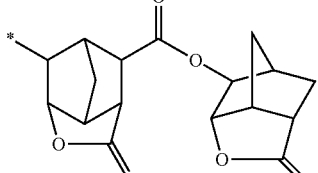
(r-lc-2-16)
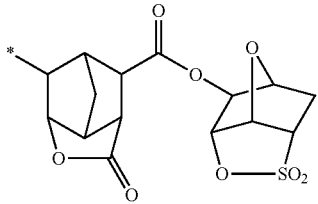

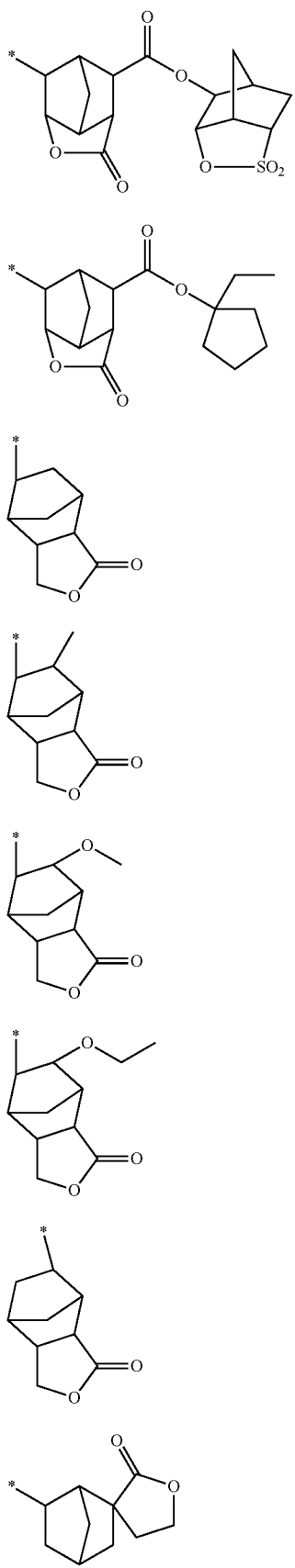
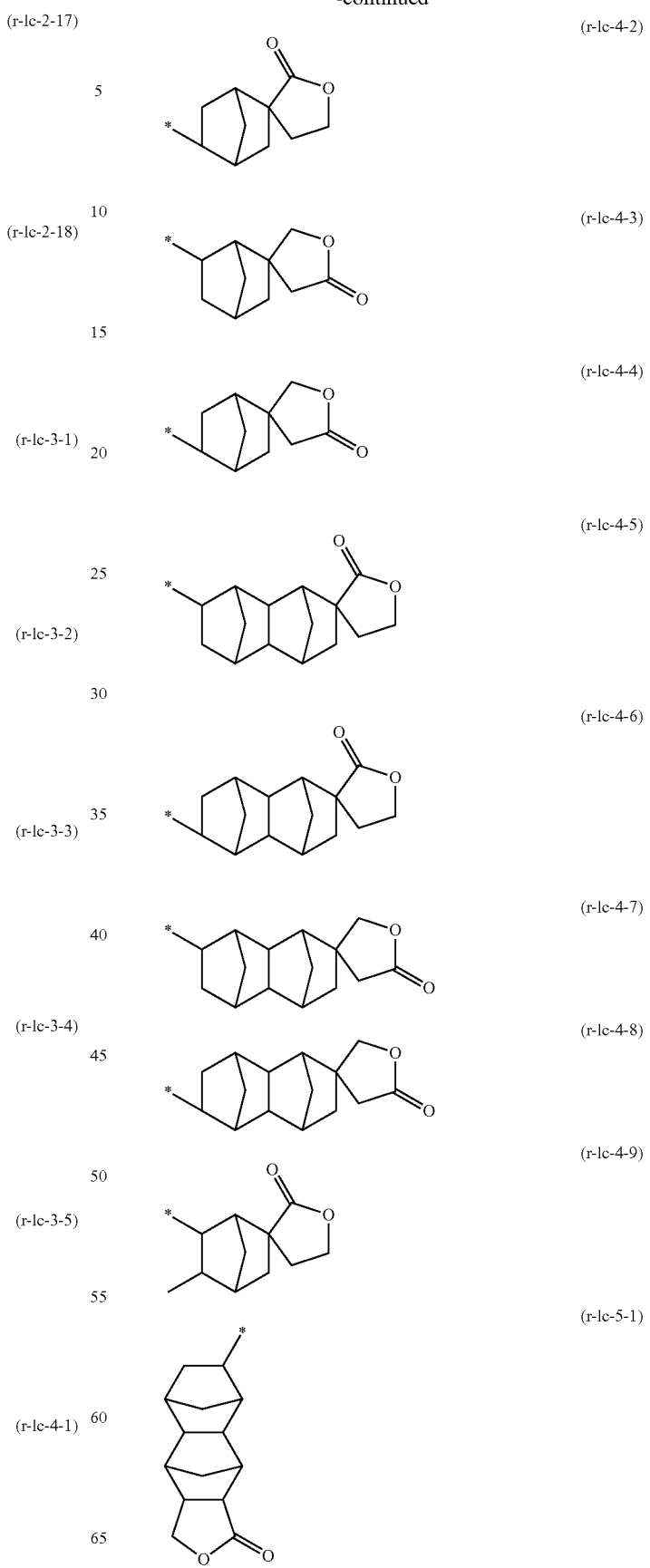

(r-lc-5-2)
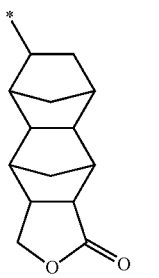

(r-lc-5-3)
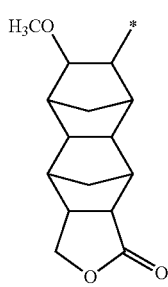

(r-lc-5-4)
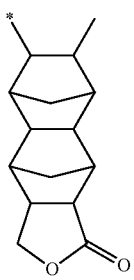

(r-lc-6-1)
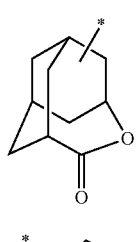

(r-lc-7-1)
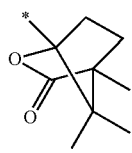

The "—$SO_2$— containing cyclic group" means a cyclic group which contains a ring having —$SO_2$— in the cyclic skeleton, and specifically, the sulfur atom (S) in —$SO_2$— is a cyclic group which forms a portion of the cyclic skeleton of the cyclic group. When the ring containing —$SO_2$— in the cyclic skeleton is counted as the first ring, if there is only the aforementioned ring, the cyclic group is referred to as a monocyclic group, and if there are other ring structures in addition to the ring, the cyclic group is referred to as a polycyclic group regardless of its structure. The —$SO_2$— containing cyclic group may be a monocyclic group or may be a polycyclic group.

The —$SO_2$— containing cyclic group is particularly preferably a cyclic group containing —O—$SO_2$— in the cyclic skeleton, that is, —O—S— in —O—$SO_2$— is preferably a cyclic group containing a sultone ring which forms a portion of the cyclic skeleton.

More specifically, examples of the —$SO_2$— containing cyclic group include the same groups which are represented by general formulae (a5-r-1) to (a5-r-4).

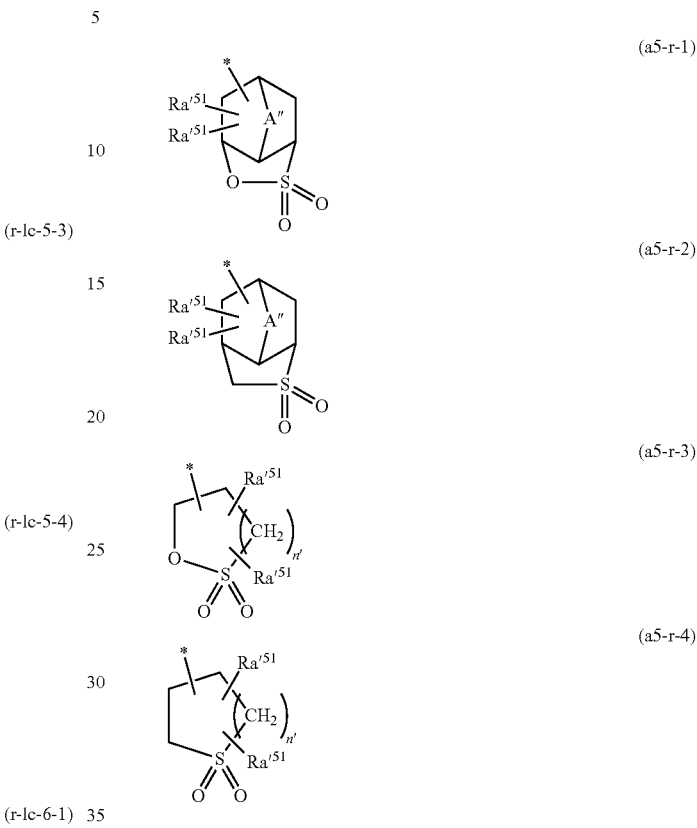

In the formula, $Ra'^{51}$'s each independently represent a hydrogen atom, an alkyl group, an alkoxy group, a halogen atom, a halogenated alkyl group, a hydroxyl group, —COOR", —OC(=O)R", a hydroxyalkyl group, or a cyano group; R" is a hydrogen atom, an alkyl group, a lactone-containing cyclic group, a carbonate-containing cyclic group, or a —$SO_2$— containing cyclic group; A" is an alkylene group having 1 to 5 carbon atoms, which may have an oxygen atom or a sulfur atom, an oxygen atom, or a sulfur atom; and n' is an integer of 0 to 2.

In general formulae (a5-r-1) and (a5-r-2), A" is the same as A" in general formulae (a2-r-2), (a2-r-3), and (a2-r-5).

An alkyl group, an alkoxy group, a halogen atom, a halogenated alkyl group, —COOR", —OC(=O)R", and a hydroxyalkyl group for $Ra'^{51}$ are the same as those exemplified in the description for $Ra'^{21}$ in general formulae (a2-r-1) to (a2-r-7).

Specific examples of the groups represented by general formulae (a5-r-1) to (a5-r-4) are described as follows. "Ac" in the formulae represents an acetyl group.

(r-sl-1-1)

(r-sl-1-2)
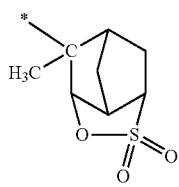
(r-sl-1-3)
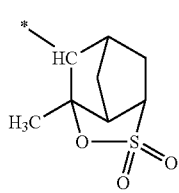
(r-sl-1-4)
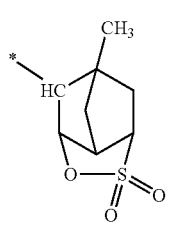
(r-sl-1-5)
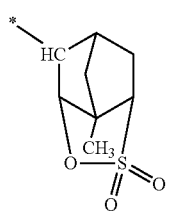
(r-sl-1-6)
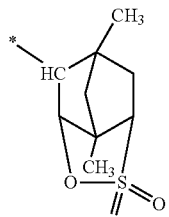
(r-sl-1-7)
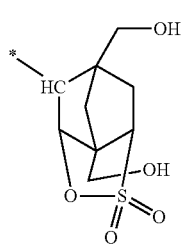
(r-sl-1-8)
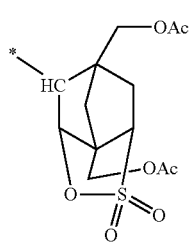
(r-sl-1-9)
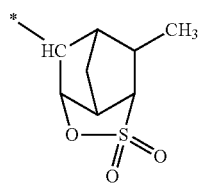
(r-sl-1-10)
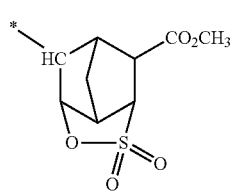
(r-sl-1-11)
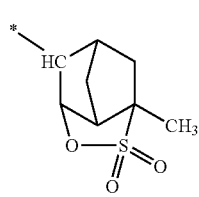
(r-sl-1-12)
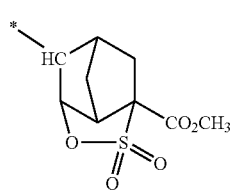
(r-sl-1-13)
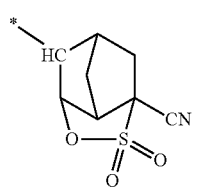
(r-sl-1-14)
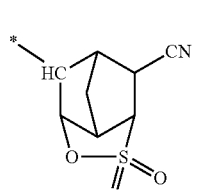
(r-sl-1-15)
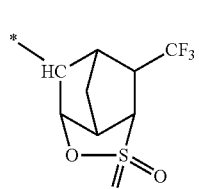
(r-sl-1-16)

(r-sl-1-17)
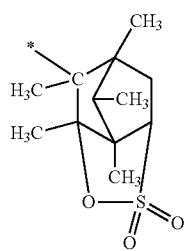
(r-sl-1-18)
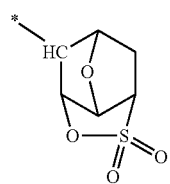
(r-sl-1-19)
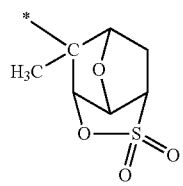
(r-sl-1-20)
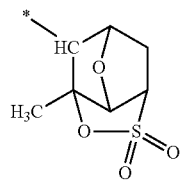
(r-sl-1-21)
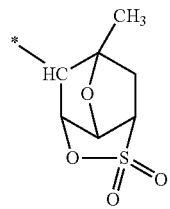
(r-sl-1-22)
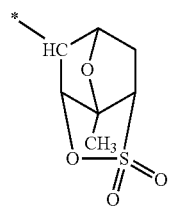
(r-sl-1-23)
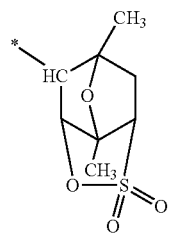
(r-sl-1-24)
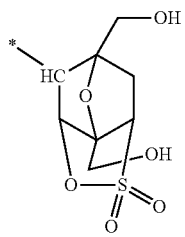
(r-sl-1-25)
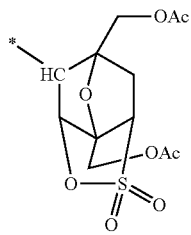
(r-sl-1-26)
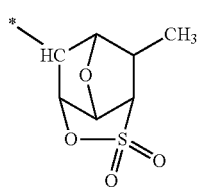
(r-sl-1-27)
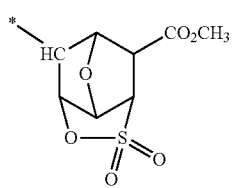
(r-sl-1-28)
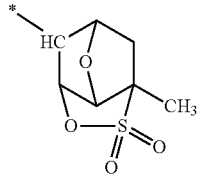
(r-sl-1-29)
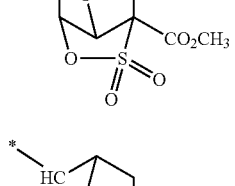
(r-sl-1-30)
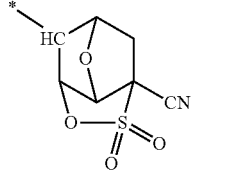
(r-sl-1-31)
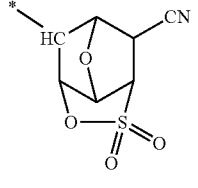

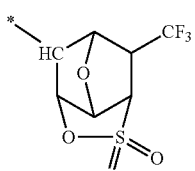
(r-sl-1-32)

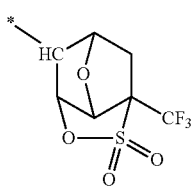
(r-sl-1-33)

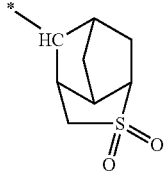
(r-sl-2-1)

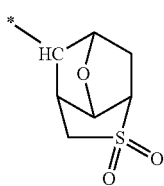
(r-sl-2-2)

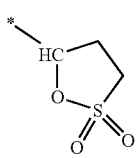
(r-sl-3-1)

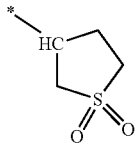
(r-sl-4-1)

The "carbonate-containing cyclic group" means a cyclic group containing a ring (carbonate ring) including —O—C(=O)—O— in the cyclic skeleton. When the carbonate ring is counted as the first ring, if there is only the carbonate ring, the cyclic group is referred to as a monocyclic group, and if there are other ring structures in addition to the carbonate ring, the cyclic group is referred to as a polycyclic group regardless of its structure. The carbonate-containing cyclic group may be a monocyclic group, or may be a polycyclic group.

The carbonate ring-containing cyclic group is not particularly limited, and any carbonate ring-containing cyclic group can be used. Specific examples thereof include the same groups which are represented by general formulae (ax3-r-1) to (ax3-r-3).

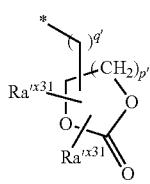
(ax3-r-1)

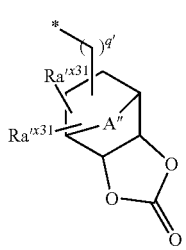
(ax3-r-2)

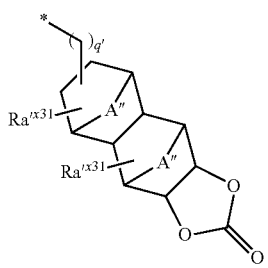
(ax3-r-3)

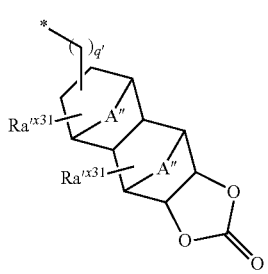

In the formulae, $Ra'^{x31}$'s each independently represent a hydrogen atom, an alkyl group, an alkoxy group, a halogen atom, a halogenated alkyl group, a hydroxyl group, —COOR″, —OC(=O)R″, a hydroxyalkyl group, or a cyano group; R″ is a hydrogen atom, an alkyl group, a lactone-containing cyclic group, a carbonate-containing cyclic group, or a —SO₂— containing cyclic group; A″ is an alkylene group having 1 to 5 carbon atoms, which may have an oxygen atom or a sulfur atom, an oxygen atom, or a sulfur atom; p' is an integer of 0 to 3; and q' is 0 or 1.

In general formulae (ax3-r-2) and (ax3-r-3), A″ is the same as A″ in general formulae (a2-r-2), (a2-r-3), and (a2-r-5).

An alkyl group, an alkoxy group, a halogen atom, a halogenated alkyl group, —COOR″, —OC(=O)R″, and a hydroxyalkyl group for $Ra'^{31}$ are the same as those exemplified in the description for $Ra'^{21}$ in general formulae (a2-r-1) to (a2-r-7).

Specific examples of the groups represented by general formulae (ax3-r-1) to (ax3-r-3) are described as follows.

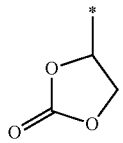
(r-cr-1-1)

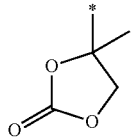
(r-cr-1-2)

(r-cr-1-3)
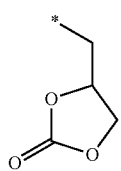
(r-cr-1-4)
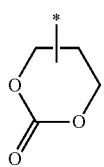
(r-cr-1-5)
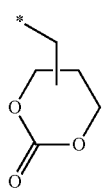
(r-cr-1-6)
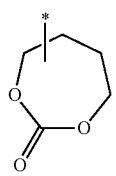
(r-cr-1-7)
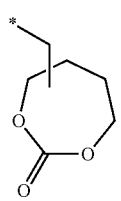
(r-cr-2-1)
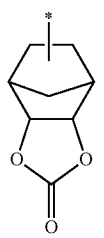
(r-cr-2-2)
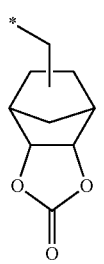
(r-cr-2-3)
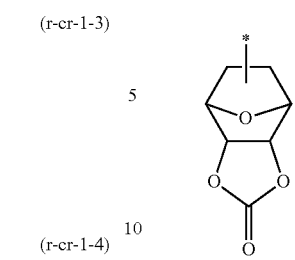
(r-cr-2-4)
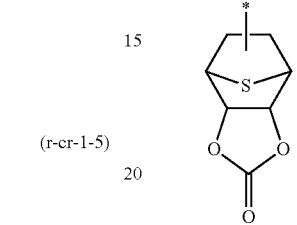
(r-cr-3-1)
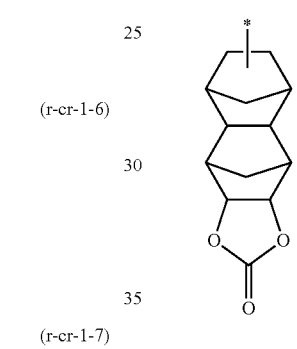
(r-cr-3-2)
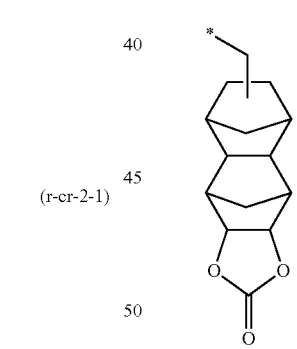
(r-cr-3-3)
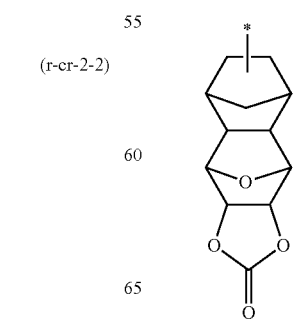

-continued (r-cr-3-4)

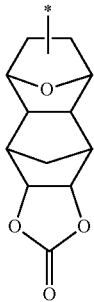

(r-cr-3-5)

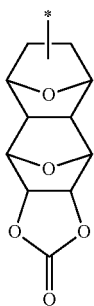

Among the structural units (a2), it is preferably a structural unit derived from acrylic ester which may be obtained by substituting a hydrogen atom bonded to an α-position carbon atom with a substituent.

The structural unit (a2) is preferably a structural unit represented by general formula (a2-1).

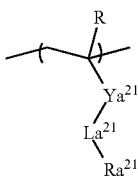

(a2-1)

In the formula, R is a hydrogen atom, an alkyl group having 1 to 5 carbon atoms, or a halogenated alkyl group having 1 to 5 carbon atoms. $Ya^{21}$ is a single bond or a divalent linking group. $La^{21}$ is —O—, —COO—, —CON (R')—, —OCO—, —CONHCO—, or —CONHCS—, and R' represents a hydrogen atom or a methyl group. Here, in the case where $La^{21}$ is —O—, $Ya^{21}$ is not —CO—. $Ra^{21}$ is a lactone-containing cyclic group, a carbonate-containing cyclic group, or a —$SO_2$— containing cyclic group.

In general formula (a2-1), R is the same as described above.

The divalent linking group of $Ya^{21}$ is not particularly limited, and preferred examples thereof include a divalent hydrocarbon group which may have a substituent and a divalent linking group containing a heteroatom.

Divalent Hydrocarbon Group which May have a Substituent:

In the case where $Ya^{21}$ is a divalent hydrocarbon group which may have a substituent, the hydrocarbon group may be an aliphatic hydrocarbon group, or may be an aromatic hydrocarbon group.

Aliphatic Hydrocarbon Group for $Ya^{21}$

The aliphatic hydrocarbon group means a hydrocarbon group having no aromaticity. The aliphatic hydrocarbon group may be saturated or unsaturated, and is preferably saturated in general.

Examples of the aliphatic hydrocarbon group include a linear or branched aliphatic hydrocarbon group, or an aliphatic hydrocarbon group containing a ring in the structure.

Linear or Branched Aliphatic Hydrocarbon Group

The number of carbon atoms of the linear aliphatic hydrocarbon group is preferably 1 to 10, is further preferably 1 to 6, is further still preferably 1 to 4, and is most preferably 1 to 3.

As a linear aliphatic hydrocarbon group, a linear alkylene group is preferable, and specific examples include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The number of carbon atoms of the branched aliphatic hydrocarbon group is preferably 3 to 10, is further preferably 3 to 6, is still further preferably 3 or 4, and is most preferably 3.

As a branched aliphatic hydrocarbon group, a branched alkylene group is preferable, and specific examples thereof include an alkyl alkylene group such as an alkyl methylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; an alkyl ethylene group such as —$CH(CH_3)CH_2$—, —$CH(CH_3)CH(CH_3)$—, —$C(CH_3)_2CH_2$—, —$CH(CH_2CH_3)CH_2$—, —$C(CH_2CH_3)_2$—$CH_2$—; an alkyl trimethylene group such as —$CH(CH_3)CH_2CH_2$— and —$CH_2CH(CH_3)CH_2$—; and an alkyl tetramethylene group such as —$CH(CH_3)CH_2CH_2CH_2$— and —$CH_2CH(CH_3)CH_2CH_2$—. As an alkyl group in an alkyl alkylene group, a linear alkyl group having 1 to 5 carbon atoms is preferable.

The linear or branched aliphatic hydrocarbon group may or may not have a substituent. Examples of the substituent include a fluorine atom, a fluorinated alkyl group having 1 to 5 carbon atoms which is substituted with a fluorine atom, and a carbonyl group.

Aliphatic Hydrocarbon Group Containing Ring in Structure

Examples of the aliphatic hydrocarbon group containing a ring in the structure include a cyclic aliphatic hydrocarbon group (a group obtained by removing two hydrogen atoms from an aliphatic hydrocarbon ring) which may contain a substituent containing a heteroatom in the ring structure, a group in which the cyclic aliphatic hydrocarbon group is bonded to a terminal of the linear or branched aliphatic hydrocarbon group, and a group in which the cyclic aliphatic hydrocarbon group is present in the middle of the linear or branched aliphatic hydrocarbon group. Examples of the linear or branched cyclic aliphatic hydrocarbon group include the same groups as described above.

The number of carbon atoms of the aliphatic hydrocarbon group is preferably 3 to 20, and is further preferably 3 to 12.

The cyclic aliphatic hydrocarbon group may be a polycyclic group, or may be a monocyclic group. As the monocyclic alicyclic hydrocarbon group, a group obtained by removing two hydrogen atoms from a monocycloalkane is preferable. The number of carbon atoms of the monocycloalkane is preferably 3 to 6. Specifically, examples thereof include cyclopentane and cyclohexane. As the polycyclic alicyclic hydrocarbon group, a group obtained by removing two hydrogen atoms from polycycloalkane is preferable, and the number of carbon atoms of polycycloalkane is preferably 7 to 12. Specifically, examples thereof include adamantane, norbornane, isobornane, tricyclodecane, and tetracyclododecane.

The cyclic aliphatic hydrocarbon group may or may not have a substituent. Examples of the substituent include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and is most preferably a methyl group, an ethyl group, a propyl group, an n-butyl group, and a tert-butyl group.

The alkoxy group as the substituent is preferably an alkoxy group having 1 to 5 carbon atoms, is further preferably a methoxy group, an ethoxy group, an n-propoxy group, an iso-propoxy group, an n-butoxy group, and a tert-butoxy group, and is most preferably a methoxy group, and an ethoxy group.

Examples of the halogen atom as the substituent include a fluorine atom, a chlorine atom, a bromine atom, and an iodine atom, and the fluorine atom is preferable.

Examples of the halogenated alkyl group as the substituent include a group obtained by substituting at least one hydrogen atom of an alkyl group with a halogen atom.

The cyclic aliphatic hydrocarbon group may be substituted with a substituent in which a portion of the carbon atoms for constituting the ring structure contains a heteroatom. The substituent containing the heteroatom is preferably —O—, —C(=O)—O—, —S—, —S(=O)$_2$—, and —S(=O)$_2$—O—.

Aromatic Hydrocarbon Group for Ya$^{21}$

The aromatic hydrocarbon group is a hydrocarbon group having at least one aromatic ring.

The aromatic ring is not particularly limited as long as it is a cyclic conjugated system having (4n+2) π-electrons, and it may be monocyclic or polycyclic. The number of the carbon atoms of the aromatic ring is preferably 5 to 30, is further preferably 5 to 20, is still further preferably 6 to 15, and is particularly preferably 6 to 12. In this regard, the number of the carbon atoms does not include the number of the carbon atoms in the substituent. Specific examples of the aromatic ring include an aromatic hydrocarbon ring such as benzene, naphthalene, anthracene, and phenanthrene; and aromatic heterocycle in which a portion of the carbon atoms which constitute the aromatic hydrocarbon ring is substituted with a heteroatom. Examples of the heteroatom in the aromatic heterocycle include an oxygen atom, a sulfur atom, and a nitrogen atom.

Specific examples of the aromatic heterocycle include a pyridine ring and a thiophene ring.

Specific examples of the aromatic hydrocarbon group include a group (an arylene group or a heteroarylene group) obtained by removing two hydrogen atoms from the aromatic hydrocarbon ring or the aromatic heterocycle; a group obtained by removing two hydrogen atoms from an aromatic compound (for example, biphenyl and fluorene) containing two or more aromatic rings; and a group (for example, a group obtained by further removing one hydrogen atom from the aryl group in the aryl alkyl group such as a benzyl group, a phenethyl group, a 1-naphtyl methyl group, a 2-naphtyl methyl group, a 1-naphtyl ethyl group, and a 2-naphtyl ethyl group) in which one hydrogen atom of the group (an aryl group or a heteroaryl group) obtained by removing one hydrogen atom from the aromatic hydrocarbon ring or the aromatic heterocycle is substituted with an alkylene group. The number of carbon atoms of the alkylene group which is bonded to the aryl group or the heteroaryl group is preferably 1 to 4, is further preferably 1 to 2, and particularly preferably 1.

In the aromatic hydrocarbon group, the hydrogen atom contained in the aromatic hydrocarbon group may be substituted with a substituent. For example, a hydrogen atom bonded to the aromatic ring in the aromatic hydrocarbon group may be substituted with a substituent. Examples of the substituent include an alkyl group, an alkoxy group, a halogen atom, a halogenated alkyl group, and a hydroxyl group.

The alkyl group as the substituent is preferably an alkyl group having 1 to 5 carbon atoms, and is most preferably a methyl group, an ethyl group, a propyl group, an n-butyl group, and a tert-butyl group.

Examples of an alkoxy group, a halogen atom, and a halogenated alkyl group as the substituent include those exemplified as a substituent which substitutes a hydrogen atom contained in the cyclic aliphatic hydrocarbon group.

Divalent Linking Group Containing a Heteroatom:

In the case where Ya$^{21}$ is a divalent linking group containing hetero atom, preferred examples of the divalent linking group containing a heteroatom include —O—, —C(=O)—O—, —O—C(=O)—, —O—C(=O)—O—, —C(=O)—NH—, —NH—, —NH—C(=NH)— (H may be substituted with a substituent such as an alkyl group and an acyl group), —S—, —S(=O)$_2$—, —S(=O)$_2$—O—, and a group represented by general formulae —Y$^{21}$—O—Y$^{22}$—, —Y$^{21}$—O—, —Y$^{21}$—C(=O)—O—, —C(=O)—O—Y$^{21}$—, —[Y$^{21}$C(=O)—O]$_{m'''}$—Y$^{22}$—, —Y$^{21}$—O—C(=O)—Y$^{22}$— and —Y$^{21}$—S(=O)$_2$—O—Y$^{22}$— (In the formulae, Y$^{21}$ and Y$^{22}$ each independently represent a divalent hydrocarbon group which may have a substituent, O represents an oxygen atom, and m" represents an integer of 0 to 3).

In the case where the divalent linking group containing the heteroatom is —C(=O)—NH—, —C(=O)—NH—C(=O)—, —NH—, or —NH—C(=NH)—, H may be substituted with a substituent such as an alkyl group and an acyl group. The substituent (an alkyl group, an acyl group, or the like) preferably has 1 to 10 carbon atoms, further preferably has 1 to 8 carbon atoms, and particularly preferably has 1 to 5 carbon atoms.

In general formulae —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m'''}$—Y$^{22}$—, —Y$^{21}$—O—C(=O)—Y$^{22}$—, and —Y$^{21}$—S(=O)$_2$—O—Y$^{22}$—, Y$^{21}$ and Y$^{22}$ each independently represent a divalent hydrocarbon group which may have a substituent. Examples of the divalent hydrocarbon group include the same group as that (divalent hydrocarbon group which may have a substituent) exemplified as the divalent linking group.

Y$^{21}$ is preferably a linear aliphatic hydrocarbon group, is further preferably a linear alkylene group, is still further preferably a linear alkylene group having 1 to 5 carbon atoms, and is particularly preferably a methylene group or an ethylene group.

Y$^{22}$ is preferably a linear or branched aliphatic hydrocarbon group, and is further preferably a methylene group, an ethylene group, or an alkyl methylene group. An alkyl group in the alkyl methylene group is preferably a linear alkyl group having 1 to 5 carbon atoms, is further preferably a linear alkyl group having 1 to 3 carbon atoms, and is most preferably a methyl group.

In the group represented by general formula —[Y$^{21}$—C(=O)—O]$_{m'''}$—Y$^{22}$—, m" is an integer of 0 to 3, is preferably an integer of 0 to 2, is further preferably 0 or 1, and is particularly preferably 1. That is, as a group represented by general formula —[$Y^{21}$—C(=O)—O]$_{m''}$—$Y^{22}$—, a group represented by general formula —$Y^{21}$—C(=O)—O—$Y^{22}$— is particularly preferable. Among them, a group represented by general formula —(CH$_2$)$_{a'}$—C(=O)—O—(CH$_2$)$_{b'}$— is preferable. In the formula, a' is an integer of 1 to 10, is preferably an integer of 1 to 8, is further preferably an integer of 1 to 5, is still further preferably 1 or 2, and is most preferably 1. b' is an integer of 1 to 10, is preferably an integer of 1 to 8, is further preferably an integer of 1 to 5, is still further preferably 1 or 2, and is most preferably 1.

$Ya^{21}$ is preferably a single bond, an ester bond [—C(=O)—O—], an ether bond (—O—), a linear or branched alkylene group, or a combination thereof.

In general formula (a2-1), $Ra^{21}$ is a lactone-containing cyclic group, a —SO$_2$— containing cyclic group, or a carbonate-containing cyclic group.

Preferred examples of the lactone-containing cyclic group, the —SO$_2$— containing cyclic group, and the carbonate-containing cyclic group for $Ra^{21}$ include groups represented by general formulae (a2-r-1) to (a2-r-7), groups represented by general formulae (a5-r-1) to (a5-r-4), and groups represented by general formulae (ax3-r-1) to (ax3-r-3).

Among them, the lactone-containing cyclic group or the —SO$_2$— containing cyclic group are preferable, the group represented by general formula (a2-r-1), (a2-r-2), (a2-r-6), or (a5-r-1) is further preferable. Specifically, any one of the groups represented by each of chemical formulae (r-lc-1-1) to (r-lc-1-7), (r-lc-2-1) to (r-lc-2-18), (r-lc-6-1), (r-sl-1-1), and (r-sl-1-18) is further preferable.

The structural unit (a2) in the (A1) component may be used alone, or two or more kinds thereof may be used in combination.

In the case where the (A1) component contains the structural unit (a2), the ratio of the structural unit (a2) is preferably 1 to 80 mol %, is further preferably 10 to 70 mol %, is still further preferably 10 to 65 mol %, and is particularly preferably 10 to 60 mol %, with respect to the total (100 mol %) of the entire structural units for constituting the (A1) component.

When the ratio of the structural unit (a2) is set to be equal to or greater than the preferred lower limit, it is possible to obtain sufficient effects by containing the structural unit (a2); on the other hand, when the ratio of the structural unit (a2) is set to be equal to or lower than the preferred upper limit, it is possible to make balance with other structural units, and thus various lithography properties and the pattern shape are improved.

Structural Unit (a9)

The (A1) component preferably has a structural unit (a9) represented by general formula (a9-1) in addition to the structural unit (a0) or, the structural unit (a0) and the structural unit (a2).

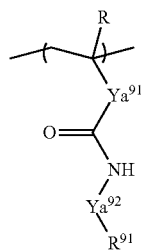

(a9-1)

In the formula, R represents a hydrogen atom, an alkyl group having 1 to 5 carbon atoms, or a halogenated alkyl group having 1 to 5 carbon atoms. $Ya^{91}$ represents a single bond or a divalent linking group. $Ya^{92}$ is a divalent linking group. $R^{91}$ is a hydrocarbon group which may have a substituent.

In general formula (a9-1), R is the same as described above.

R is preferably a hydrogen atom, an alkyl group having 1 to 5 carbon atoms, or a fluorinated alkyl group having 1 to 5 carbon atoms, and a hydrogen atom or a methyl group is particularly preferable in terms of industrial availability.

In general formula (a9-1), examples of the divalent linking group for $Ya^{91}$ include the same divalent linking group as that of $Ya^{21}$ in general formula (a2-1). $Ya^{91}$ is preferably a single bond.

In general formula (a9-1), examples of the divalent linking group for $Ya^{92}$ include the same divalent linking group as that of $Ya^{21}$ in general formula (a2-1).

With respect to the divalent linking group for $Ya^{92}$, as a divalent hydrocarbon group which may have a substituent, a linear or branched aliphatic hydrocarbon group is preferable.

The number of carbon atoms of the linear aliphatic hydrocarbon group is preferably 1 to 10, is further preferably 1 to 6, is further still preferably 1 to 4, and is most preferably 1 to 3. As the linear aliphatic hydrocarbon group, the linear alkylene group is preferable, and specifically, examples thereof include a methylene group [—CH$_2$—], an ethylene group [—(CH$_2$)$_2$—], a trimethylene group [—(CH$_2$)$_3$—], a tetramethylene group [—(CH$_2$)$_4$—], and a pentamethylene group [—(CH$_2$)$_5$—].

The number of carbon atoms of the branched aliphatic hydrocarbon group is preferably 3 to 10, is further preferably 3 to 6, is still further preferably 3 or 4, and is most preferably 3. As the branched aliphatic hydrocarbon group, a branched chain alkylene group is preferable, and specifically, examples thereof include an alkylalkylene group such as an alkyl methylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; an alkyl ethylene group such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; an alkyl trimethylene group such as —CH(CH$_3$)CH$_2$CH$_2$—, and —CH$_2$CH(CH$_3$)CH$_2$—; and an alkyl tetramethylene group such as —CH(CH$_3$)CH$_2$CH$_2$CH$_2$— and —CH$_2$CH(CH$_3$)CH$_2$CH$_2$—. As an alkyl group in the alkylalkylene group, a linear alkyl group having 1 to 5 carbon atoms is preferable.

In addition, with respect to the divalent linking group for $Ya^{92}$, examples of the divalent linking group which may have a heteroatom include —O—, —C(=O)—O—, —C(=O)—, —O—C(=O)—O—, —C(=O)—NH—, —NH—, —NH—C(=NH)— (H may be substituted with a substituent such as an alkyl group and an acyl group), —S—, —S(=O)$_2$—, —S(=O)$_2$—O—, —C(=S)—, and a group represented by general formula —$Y^{21}$—O—$Y^{22}$—, —$Y^{21}$—O—, —$Y^{21}$—C(=O)—O—, —C(=O)—O—$Y^{21}$, [$Y^{21}$—C(=O)—O]$_{m'}$—$Y^{22}$— or —$Y^{21}$—O—C(=O)—$Y^{22}$— (where $Y^{21}$ and $Y^{22}$ each independently represent a divalent hydrocarbon group which may a substituent, O is an oxygen atom, and m' is an integer 0 to 3). Among them, —C(=O)— and —C(=S)— are preferable.

In general formula (a9-1), examples of the hydrocarbon group for $R^{91}$ include an alkyl group, a monovalent alicyclic hydrocarbon group, an aryl group, and an aralkyl group.

The number of carbon atoms of the alkyl group for $R^{91}$ is preferably 1 to 8, is further preferably 1 to 6, and is further still preferably 1 to 4, and the alkyl group may be a linear or branched group. Specifically, preferred examples thereof include a methyl group, an ethyl group, a propyl group, a butyl group, a hexyl group, and an octyl group.

The number of carbon atoms of the monovalent alicyclic hydrocarbon group for $R^{91}$ is preferably 3 to 20, and is further preferably 3 to 12, and the monovalent alicyclic hydrocarbon group may be polycyclic group, and may be a monocyclic group. The monocyclic alicyclic hydrocarbon group is preferably a group obtained by removing one or more hydrogen atoms from monocycloalkane. The number of carbon atoms of the monocycloalkane is preferably 3 to 6, and specifically, is preferably cyclobutane, cyclopentane, cyclohexane, or the like. The polycyclic alicyclic hydrocarbon group is preferably a group obtained by removing one or more hydrogen atoms from polycycloalkane, and the number of carbon atoms of the polycycloalkane is preferably 7 to 12. Specifically, examples thereof include adamantane, norbornane, isobornane, tricyclodecane, and tetracyclododecane.

The number of carbon atoms of the aryl group $R^{91}$ is preferably 6 to 18, and is further preferably 6 to 10, and specifically, a phenyl group is particularly preferable.

As the aralkyl group for $R^{91}$, an aralkyl group in which an alkylene group having 1 to 8 carbon atoms and "the aryl group for $R^{91}$" are bonded to each other is preferable, an aralkyl group in which an alkylene group having 1 to 6 carbon atoms and "the aryl group for $R^{91}$" are bonded to each other is further preferable, and an aralkyl group in which an alkylene group having 1 to 4 carbon atoms and "the aryl group for $R^{91}$" are bonded to each other is particularly preferable.

Regarding the hydrocarbon group for $R^{91}$, at least one hydrogen atom of the hydrocarbon group are preferably substituted with a fluorine atom, 30% to 100% of the hydrogen atoms contained in the hydrocarbon group is preferably substituted with a fluorine atom. Among them, a perfluoroalkyl group in which all of the hydrogen atoms of the alkyl group are substituted with a fluorine atom is particularly preferable.

The hydrocarbon group $R^{91}$ may have a substituent. Examples of the substituent include a halogen atom, an oxy group ($=O$), a hydroxyl group ($-OH$), an amino group ($-NH_2$), and $-SO_2-NH_2$. In addition, a portion of a carbon atom forming a hydrocarbon group may be substituted with a substituent containing a heteroatom. Examples of the substituent containing the heteroatom include $-O-$, $-NH-$, $-N=$, $-C(=O)-O-$, $-S-$, $-S(=O)_2-$, and $-S(=O)_2-O-$.

In $R^{91}$, examples of the hydrocarbon group having a substituent include a lactone-containing cyclic group represented by general formulae (a2-r-1) to (a2-r-7).

In addition, with respect to $R^{91}$, examples of a hydrocarbon group having a substituent include an $-SO_2-$ containing cyclic group represented by general formula (a5-r-1) to (a5-r-4); and a substituted aryl group and a monovalent heterocyclic group represented by the following chemical formula.

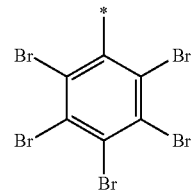
(r-ar-1)

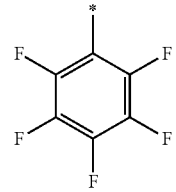
(r-ar-2)

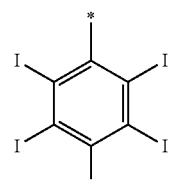
(r-ar-3)

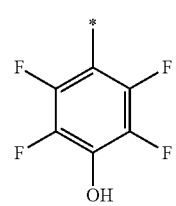
(r-ar-4)

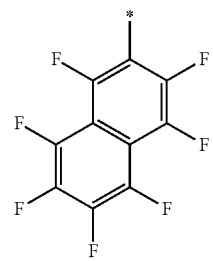
(r-ar-5)

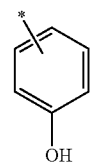
(r-ar-6)

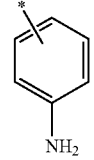
(r-ar-7)

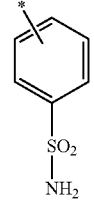
(r-ar-8)

(r-hr-1) 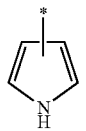

(r-hr-2) 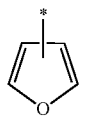

(r-hr-3) 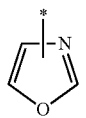

(r-hr-4) 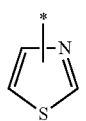

(r-hr-5) 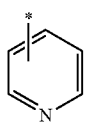

(r-hr-6) 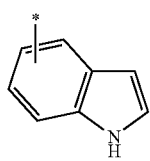

(r-hr-7) 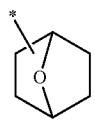

(r-hr-8) 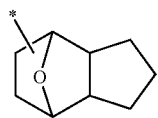

(r-hr-9) 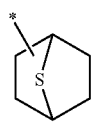

(r-hr-10) 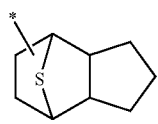

(r-hr-11) 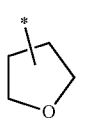

(r-hr-12) 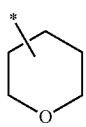

(r-hr-13) 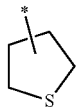

(r-hr-14) 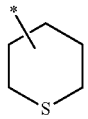

(r-hr-15) 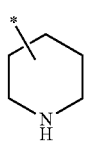

(r-hr-16) 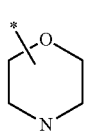

In the structural unit (a9), a structural unit represented by general formula (a9-1-1) is preferable.

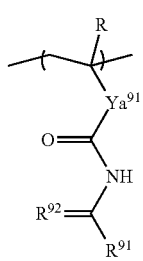

(a9-1-1)

In the formula, R is the same as described above, $Ya^{91}$ is a single bond or a divalent linking group, $R^{91}$ is a hydrocarbon group which may have a substituent, and $R^{92}$ is an oxygen atom or a sulfur atom.

In general formula (a9-1-1), the description of $Ya^{91}$, $R^{91}$, and R is the same as described above.

In addition, $R^{92}$ is an oxygen atom or a sulfur atom.

Specific examples of the structural unit represented by general formula (a9-1) or general formula (a9-1-1) will be described. In the following formula, $R^{\alpha}$ represents a hydrogen atom, a methyl group, or a trifluoromethyl group.

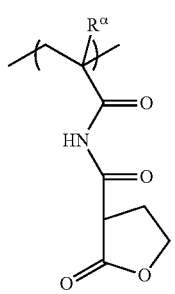 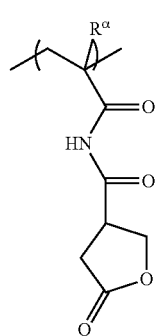

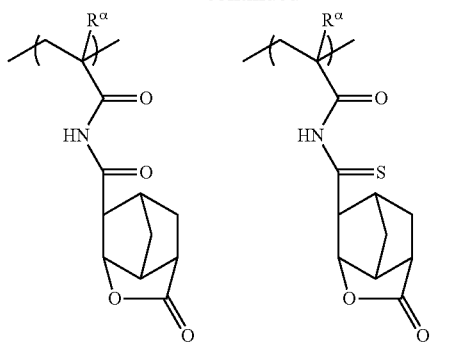
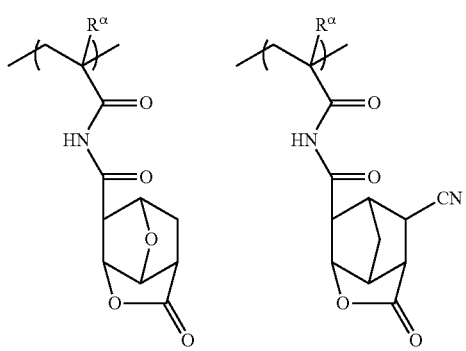
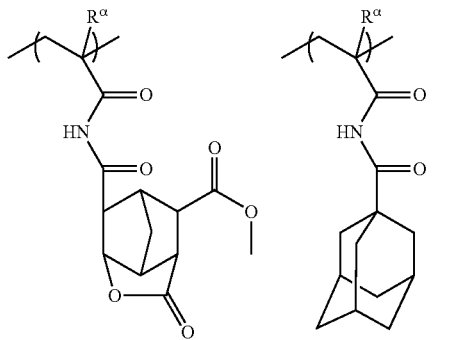
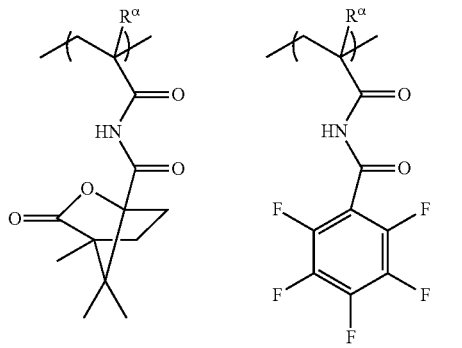
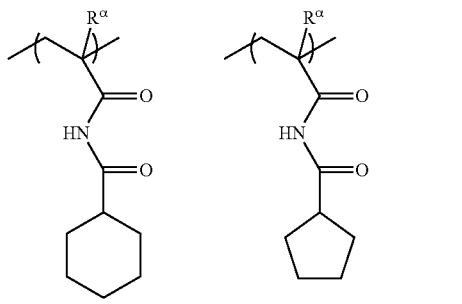
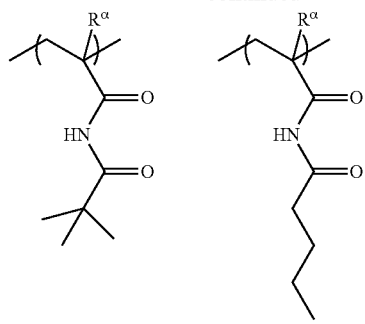
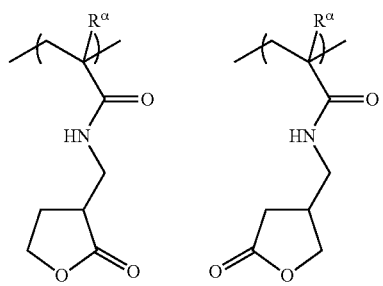
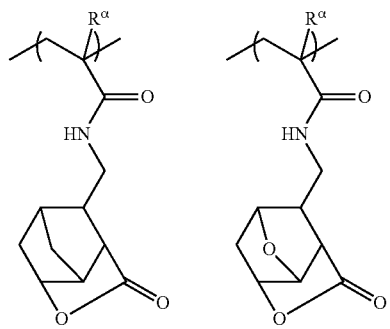
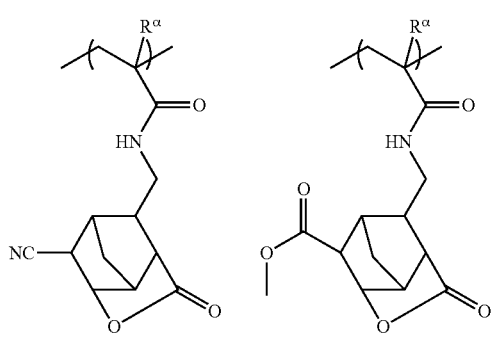
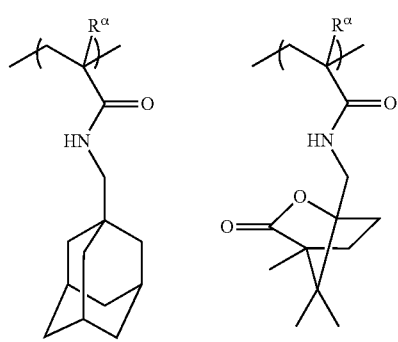

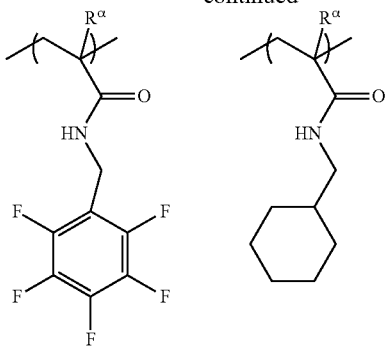
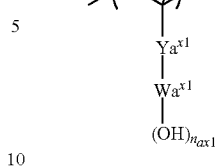

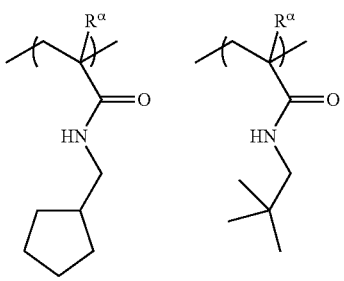

The structural unit (a9) contained in the (A1) component may be used alone or two or more kinds of thereof may be used in combination.

In the case where the (A1) component contains the structural unit (a9), the ratio of the structural unit (a9) is preferably 1 to 40 mol %, is further preferably 3 to 30 mol %, and is particularly preferably 10 to 30 mol %, with respect to the total (100 mol %) of the structural units for constituting the (A1) component.

When the ratio of the structural unit (a9) is set to be equal to or greater than the lower limit value, the lithography properties such as the developing properties and EL margin are improved, on the other hand, when the ratio of the structural unit (a9) is set to be equal to or lower than the upper limit, it becomes easier to take balance with other structural units.

Structural Unit Represented by General Formula (a10-1)

The (A1) component preferably has a structural unit (a10) represented by general formula (a10-1) in addition to the structural unit (a0).

(a10-1)

In the formula, R represents a hydrogen atom, an alkyl group having 1 to 5 carbon atoms, or a halogenated alkyl group having 1 to 5 carbon atoms. $Ya^{x1}$ represents a single bond or a divalent linking group. $Wa^{x1}$ is a $(n_{ax1}+1)$ valent aromatic hydrocarbon group. $n_{ax1}$ is an integer 1 to 3.

In general formula (a10-1), R is the same as described above.

R is preferably a hydrogen atom, an alkyl group having 1 to 5 carbon atoms, or a fluorinated alkyl group having 1 to 5 carbon atoms, and a hydrogen atom or a methyl group is particularly preferable in terms of industrial availability.

In general formula (a10-1), examples of the divalent linking group for $Ya^{x1}$ include the same divalent linking group of $Ya^{21}$ in general formula (a2-1). $Ya^{x1}$ is preferably a single bond.

Examples of the aromatic hydrocarbon group for $Wa^{x1}$ include a group obtained by removing $(n_{ax1}+1)$ hydrogen atoms from the aromatic ring. Here, the aromatic ring is not particularly limited as long as it is a cyclic conjugated system having $(4n+2)$ π-electrons, and it may be monocyclic or polycyclic. The number of carbon atoms of the aromatic ring is preferably 5 to 30, is further preferably 5 to 20, is still further preferably 6 to 15, and is particularly preferably 6 to 12. Specific examples of the aromatic ring include an aromatic hydrocarbon ring such as benzene, naphthalene, anthracene, and phenanthrene; and aromatic heterocycle in which a portion of carbon atoms forming the aromatic hydrocarbon ring is substituted with a heteroatom. Examples of the heteroatom in the aromatic heterocycle include an oxygen atom, a sulfur atom, and a nitrogen atom. Specific examples of the aromatic heterocycle include a pyridine ring and a thiophene ring.

In general formula (a10-1), $n_{ax1}$ is an integer 1 to 3, is preferably 1 or 2, and is further preferably 1.

Specific examples of the structural unit represented by general formula (a10-1) will be described below. In the following formula, $R^{\alpha}$ represents a hydrogen atom, a methyl group, or a trifluoromethyl group.

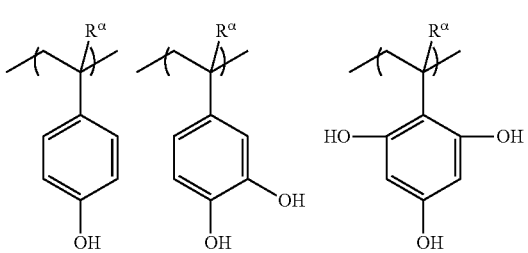

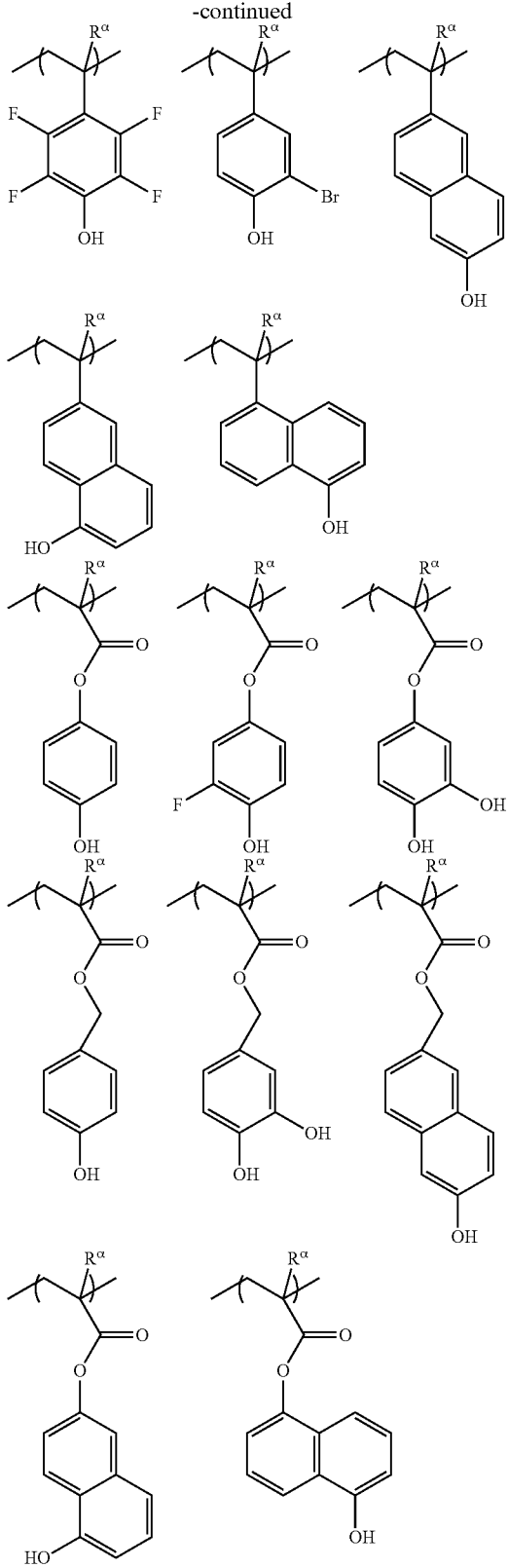

The structural unit (a10) contained in the (A1) component may be used alone or two or more kinds thereof may be used in combination.

Among them, the structural unit (a10) is preferably a structural unit containing a hydroxystyrene skeleton, and for example, a structural unit represented by general formula (a10-1-1) is particularly preferable.

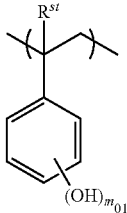

(a10-1-1)

In the formula, $R^{st}$ represents a hydrogen atom or a methyl group. $m_{01}$ represents an integer 1 to 3.

In the case where the (A1) component contains the structural unit (a10), the ratio of the structural unit (a10) is preferably 10 to 70 mol %, is further preferably 15 to 65 mol %, and is particularly preferably 20 to 60 mol %, with respect to the total (100 mol %) of the structural units for constituting the (A1) component.

When the ratio of the structural unit (a10) is set to be equal to or greater than the lower limit value, the lithography properties such as the developing properties and EL margin are improved, on the other hand, when the ratio of the structural unit (a10) is set to be equal to or lower than the upper limit, it becomes easier to take balance with other structural units.

Other Structural Units

The (A1) component may have other structural units in addition to the structural unit (a0), the structural unit (a2), the structural unit (a9), and the structural unit (a10).

Examples of other structural units include a structural unit (a1) containing an acid-decomposable group in which the polarity is increased under the action of the acid (here, except for a structural unit corresponding to the structural unit (a0)), a structural unit derived from hydroxystyrene, a structural unit derived from a hydroxystyrene derivative (here, except for a structural unit corresponding to the structural unit (a10)) a structural unit containing a polar group-containing aliphatic hydrocarbon group (here, except for a structural unit corresponding to the structural unit (a0), the structural unit (a2) or the structural unit (a9)), and a structural unit containing an acid non-dissociable aliphatic cyclic group.

Structural Unit (a1):

The structural unit (a1) is a structural unit containing an acid-decomposable group in which the polarity is increased under the action of the acid (here, except for a structural unit corresponding to the structural unit (a0)).

Examples of the acid-decomposable group in which the polarity is increased under the action of the acid include a group which is decomposed by the action of an acid to generate a polar group.

Examples of the polar group include a carboxy group, a hydroxyl group, an amino group, and a sulfo group (—SO$_3$H). Among them, a polar group containing —OH in the structure (hereinafter, referred to as "OH-containing polar group") is preferable, a carboxy group or a hydroxyl group is further preferable, and a carboxy group is particularly preferable.

More specifically, examples of the acid-decomposable group include a group in which the polar group is protected by an acid dissociable group (for example, a group in which a hydrogen atom of an OH-containing polar group is protected by the acid dissociable group).

Here, the "acid dissociable group" means both (i) a group having the acid decomposability with which the bond between the acid dissociable group and the atom adjacent to the acid dissociable group can be cleaved under the action of the acid, and (ii) a group in which the bond between the acid dissociable group and the atom adjacent to the acid dissociable group can be cleaved due to decarboxylation after a portion of the bond is cleaved under the action of the acid.

The acid dissociable group for constituting an acid-decomposable group is required to be a group having the lower polarity than that of the polar group generated by dissociation of the acid dissociable group, and with this, when the acid dissociable group is dissociated under the action of the acid, a polar group having the higher polarity than that of the acid dissociable group is generated, and thereby the polarity is increased. As a result, the polarity of the entire components (A1) is increased. As the polarity is increased, the solubility in the developing solution is relatively changed, and in the case where the developing solution is an alkali developing solution, the solubility is increased; whereas, in the case where the developing solution is an organic developing solution, the solubility is decreased.

Examples of the acid dissociable group include a group which has been proposed as an acid dissociable group for a base resin for chemically amplified resist composition.

Specific examples of the group which has been proposed as an acid dissociable group of a base resin chemically amplified resist composition include an "acetal-type acid dissociable group", a "tertiary alkyl ester-type acid dissociable group", and a "tertiary alkyloxycarbonyl acid dissociable group" which will be described as follows.

Acetal-Type Acid Dissociable Group:

Among the above-described polar groups, examples of the acid dissociable group which protects a carboxy group or a hydroxyl group include an acid dissociable group (hereinafter, referred to as the "acetal-type acid dissociable group" in some cases) represented by general formula (a1-r-1).

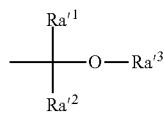
(a1-r-1)

In the formula, $Ra'^1$ and $Ra'^2$ are a hydrogen atom or an alkyl group, $Ra'^3$ is a hydrocarbon group, and $Ra'^3$ may form a ring by bonding to any of $Ra'^1$ and $Ra'^2$.

In general formula (a1-r-1), it is preferable that at least one of $Ra'^1$ and $Ra'^2$ is a hydrogen atom, and it is further preferable that both of them are a hydrogen atom.

In the case where $Ra'^1$ or $Ra'^2$ is an alkyl group, examples of the alkyl group include the same alkyl group as that exemplified as a substituent which may be bonded to the α-position carbon atom in the description of the α-substituted acrylic ester, and an alkyl group having 1 to 5 carbon atoms is preferable. Specifically, a linear or branched alkyl group is preferable. More specifically, examples thereof include a methyl group, an ethyl group, a propyl group, an isopropyl group, an n-butyl group, an isobutyl group, a tert-butyl group, a pentyl group, an isopentyl group, and a neopentyl group, and among them, the methyl group or the ethyl group is further preferable, and the methyl group is particularly preferable.

In general formula (a1-r-1), examples of the hydrocarbon group of $Ra'^3$ include a linear or branched alkyl group, and a cyclic hydrocarbon group.

The number of the carbon atoms of the linear alkyl group is preferably 1 to 5, is further preferably 1 to 4, and is still further preferably 1 or 2. Specific examples thereof include a methyl group, an ethyl group, an n-propyl group, an n-butyl group, and an n-pentyl group. Among them, the methyl group, the ethyl group, or the n-butyl group is preferable, and the methyl group or the ethyl group is further preferable.

The number of the carbon atoms of the branched alkyl group is preferably 3 to 10, and is further preferably 3 to 5. Specific examples thereof include an isopropyl group, an isobutyl group, a tert-butyl group, an isopentyl group, a neopentyl group, a 1,1-diethyl propyl group, and a 2,2-dimethyl butyl group, and among them, the isopropyl group is preferable.

In the case where $Ra'^3$ is a cyclic hydrocarbon group, the hydrocarbon group may be an aliphatic hydrocarbon group or an aromatic hydrocarbon group, and may be a polycyclic group or a monocyclic group.

The aliphatic hydrocarbon group which is a monocyclic group is preferably a group obtained by removing one hydrogen atom from monocycloalkane. The number of carbon atoms of the monocycloalkane is preferably 3 to 6, and specific examples thereof include cyclopentane and cyclohexane.

Examples of the aliphatic hydrocarbon group which is the polycyclic group include a group obtained by removing one hydrogen atom from polycycloalkane. The number of the carbon atoms of polycycloalkane is preferably 7 to 12, and specific examples thereof include adamantane, norbornane, isobornane, tricyclodecane, and tetracyclododecane.

In the case where the cyclic hydrocarbon group of $Ra'^3$ is an aromatic hydrocarbon group, the aromatic hydrocarbon group is a hydrocarbon group having at least one aromatic ring.

The aromatic ring is not particularly limited as long as it is a cyclic conjugated system having (4n+2) π-electrons, and it may be monocyclic or polycyclic. The number of carbon atoms of the aromatic ring is preferably 5 to 30, is further preferably 5 to 20, is still further preferably 6 to 15, and is particularly preferably 6 to 12. Specific examples of the aromatic ring include an aromatic hydrocarbon ring such as benzene, naphthalene, anthracene, and phenanthrene; and aromatic heterocycle in which a portion of carbon atoms forming the aromatic hydrocarbon ring is substituted with a heteroatom. Examples of the heteroatom in the aromatic heterocycle include an oxygen atom, a sulfur atom, and a nitrogen atom. Specific examples of the aromatic heterocycle include a pyridine ring and a thiophene ring.

Specific examples of the aromatic hydrocarbon group for $Ra'^3$ include a group (an aryl group or a heteroaryl group) obtained by removing one hydrogen atom from an aromatic hydrocarbon ring or an aromatic heterocycle; a group obtained by removing one hydrogen atom from an aromatic compound (for example, biphenyl and fluorene) containing two or more aromatic rings; and a group (for example, an aryl alkyl group such as a benzyl group, a phenethyl group, a 1-naphtyl methyl group, a 2-naphtyl methyl group, a 1-naphtyl ethyl group, and a 2-naphtyl ethyl group) obtained by substituting one hydrogen atom of the aromatic hydrocarbon ring or the aromatic heterocycle with an alkylene group. The number of the carbon atoms of the alkylene group which is bonded to the aromatic hydrocarbon ring or the aromatic heterocycle is preferably 1 to 4, is further preferably 1 to 2, and is particularly preferably 1.

The cyclic hydrocarbon group for $Ra'^3$ may have a substituent. Examples of the substituent include the same group as described $Ra^{05}$.

In the case where $Ra'^3$ forms a ring by bonding to any one of $Ra'^1$ and $Ra'^2$, the cyclic group is preferably a group of 4- to 7-membered rings, and is further preferably a group of 4- to 6-membered rings. Specific examples of the cyclic group include a tetrahydropyranyl group and a tetrahydrofuranyl group.

Tertiary Alkyl Ester-Type Acid Dissociable Group:

Among the above-described polar groups, examples of the acid dissociable group which protects a carboxy group include an acid dissociable group represented by general formula (a1-r-2).

Note that, among acid dissociable groups represented by the following formula (a1-r-2), an acid dissociable group which is composed of an alkyl group is referred to as "tertiary alkyl ester-type acid dissociable group" in some cases for the sake of convenience.

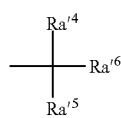

(a1-r-2)

In the formula, $Ra'^4$ to $Ra'^6$ each independently represent a hydrocarbon group, and $Ra'^5$ and $Ra'^6$ may be bonded to each other so as to form a ring.

Examples of the hydrocarbon group for $Ra'^{14}$ include a linear or branched alkyl group, a chain or cyclic alkenyl group, and a cyclic hydrocarbon group.

Examples of the linear or branched alkyl group, and the cyclic hydrocarbon group (an aliphatic hydrocarbon group which is a monocyclic group, an aliphatic hydrocarbon group which is a polycyclic group, and an aromatic hydrocarbon group) for $Ra'^4$ are the same as those for $Ra'^3$.

The chain or cyclic alkenyl group for $Ra'^4$ is preferably an alkenyl group having 2 to 10 carbon atoms.

Examples of the hydrocarbon group for $Ra'^5$ and $Ra'^6$ are the same as those for $Ra'^3$.

In the case where $Ra'^5$ and $Ra'^6$ are bonded to each other so as to form a ring, a group represented by general formula (a1-r2-1), a group represented by general formula (a1-r2-2), and a group represented by general formula (a1-r2-3).

On the other hand, in the case where $Ra'^4$ to $Ra'^6$ are not bonded to each other, and are each independently a hydrocarbon group, a group represented by general formula (a1-r2-4) can be exemplified.

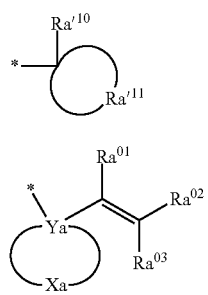

(a1-r2-1)

(a1-r2-2)

(a1-r2-3)

(a1-r2-4)

In general formula (a1-r2-1), $Ra'^{10}$ represents an alkyl group having 1 to 10 carbon atoms, and $Ra'^{11}$ represents a group which forms an aliphatic cyclic group together with a carbon atom to which $Ra'^{10}$ is bonded. In general formula (a1-r2-2), Ya is a carbon atom. Xa is a group forming a cyclic hydrocarbon group together with Ya. At least one hydrogen atom contained in the cyclic hydrocarbon group may be substituted. $Ra^{01}$ to $Ra^{03}$ each independently represent, a hydrogen atom, a monovalent chain saturated hydrocarbon group having 1 to 10 carbon atoms, or a monovalent aliphatic cyclic saturated hydrocarbon group having 3 to 20 carbon atoms. At least one hydrogen atom contained in the chain saturated hydrocarbon group and the aliphatic cyclic saturated hydrocarbon group may be substituted. Two or more of $Ra^{01}$ to $Ra^{03}$ may be bonded to each other to form a cyclic structure. A symbol of * represents a bond.

In general formula (a1-r2-3), Yaa is a carbon atom. Xaa is a group forming an aliphatic cyclic group together with Yaa. $Ra^{04}$ is an aromatic hydrocarbon group which may have a substituent. A symbol of * represents a bond.

In general formula (a1-r2-4), $Ra'^{12}$ and $Ra'^{13}$ each independently represent a monovalent chain saturated hydrocarbon group having 1 to 10 carbon atoms or a hydrogen atom. At least one hydrogen atom of the chain saturated hydrocarbon group may be substituted. $Ra''^{14}$ is a hydrocarbon group (here, except for a phenyl group, a naphthyl group, and an anthryl group) which may have a substituent. *''' represents a bond (the same applies to the present specification).

In general formula (a1-r2-1), the alkyl group having 1 to 10 carbon atoms in $Ra'^{10}$ is preferably a group exemplified by a linear or branched alkyl group of $Ra'^3$ in general formula (a1-r-1).

$Ra'^{10}$ is preferably an alkyl group having 1 to 5 carbon atoms. In general formula (a1-r2-1), an aliphatic cyclic group which is formed of $Ra'^{11}$ together with the carbon atom to which $Ra'^{10}$ is bonded is preferably a group exemplified as an aliphatic hydrocarbon group which is a monocyclic group or a polycyclic group of $Ra'^3$ in general formula (a1-r-1).

In general formula (a1-r2-2), as a cyclic hydrocarbon group which is formed of Xa together with Ya, a group obtained by removing one or more hydrogen atoms from the cyclic monovalent hydrocarbon group (an aliphatic hydrocarbon group and an aromatic hydrocarbon group) in $Ra'^3$ in general formula (a1-r-1).

The cyclic hydrocarbon group which is formed of Xa together with Ya may have a substituent. Examples of the substituent include same groups as the substituents that the cyclic hydrocarbon group for $Ra'^3$ may have.

In general formula (a1-r2-2), with respect to $Ra^{01}$ to $Ra^{03}$, examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

In $Ra^{o1}$ to $Ra^{o3}$, examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; a polycyclic aliphatic saturated hydrocarbon group such as a bicyclo [2.2.2] octanyl group, a tricyclo [5.2.1.02, 6] decanyl group, a tricyclo [3.3.1.13,7] decanyl group, a tetracyclo [6.2.1.13,6.02,7] dodecanyl group, and an adamantyl group.

Among them, from the viewpoint of the ease of synthesis of the monomer compound which derives the structural unit (a1), $Ra^{o1}$ to $Ra^{o3}$ is preferably a hydrogen atom and a monovalent chain saturated hydrocarbon group having 1 to 10 carbon atoms, and among them, a hydrogen atom, a methyl group, and an ethyl group are still preferable, and a hydrogen atom is particularly preferable.

Examples of the chain saturated hydrocarbon group represented by $Ra^{o1}$ to $Ra^{o3}$, or the substituent having an aliphatic cyclic saturated hydrocarbon group include a group which is the same as $Ra^{o5}$.

Examples of the group containing a carbon-carbon double bond which is generated by forming a cyclic structure in which two or more of $Ra^{o1}$ to $Ra^{o3}$ are bonded to each other include a cyclopentenyl group, a cyclohexenyl group, a methyl cyclopentenyl group, a methyl cyclohexenyl group, a cyclopentylideneethenyl group, and a cyclohexylideneethenyl group. Among them, from the viewpoint of the ease of synthesis of the monomer compound which derives the structural unit (a1), a cyclopentenyl group, a cyclohexenyl group, and a cyclopentylideneethenyl group are preferable.

In general formula (a1-r2-3), an aliphatic cyclic group which is formed of Xaa together with Yaa is preferably a group exemplified as an aliphatic hydrocarbon group which is a monocyclic group or a polycyclic group of $Ra^{t3}$ in general formula (a1-r-1).

In general formula (a1-r2-3), examples of the aromatic hydrocarbon group for $Ra^{o4}$ include a group obtained by removing one or more hydrogen atoms from an aromatic hydrocarbon ring having carbon atoms 5 to 30. Among them, $Ra^{o4}$ is preferably a group obtained by removing one or more hydrogen atoms from an aromatic hydrocarbon ring having carbon atoms 6 to 15, a group obtained by removing one or more hydrogen atoms from benzene, naphthalene, anthracene, or phenanthrene is further preferable, a group obtained by removing one or more hydrogen atoms from benzene, naphthalene, or anthracene is still further preferable, a group obtained by removing one or more hydrogen atoms from benzene and naphthalene is particularly preferable, and a group obtained by removing one or more hydrogen atoms from benzene is most preferable.

Examples of the substituent that $Ra^{o4}$ in general formula (a1-r2-3) may have include a methyl group, an ethyl group, a propyl group, a hydroxyl group, a carboxyl group, a halogen atom (a fluorine atom, a chlorine atom, a bromine atom, or the like), an alkoxy group (a methoxy group, an ethoxy group, a propoxy group, a butoxy group, or the like), and an alkyloxycarbonyl group.

In general formula (a1-r2-4), $Ra^{t12}$ and $Ra^{t13}$ each independently represent a monovalent chain saturated hydrocarbon group having 1 to 10 carbon atoms or a hydrogen atom. With respect to $Ra^{t12}$ and $Ra^{t13}$, examples of the monovalent chain saturated hydrocarbon group having 1 to 10 carbon atoms include the same monovalent chain saturated hydrocarbon group having 1 to 10 carbon atoms as that for $Ra^{o1}$ to $Ra^{o3}$. At least one hydrogen atom of the chain saturated hydrocarbon group may be substituted.

Among them, as $Ra^{t12}$ and $Ra^{t13}$, a hydrogen atom and an alkyl group having 1 to 5 carbon atoms are preferable, an alkyl group having 1 to 5 carbon atoms is further preferable, a methyl group and an ethyl group are still further preferable, and a methyl group is particularly preferable.

In the case where the chain saturated hydrocarbon group represented by $Ra^{t12}$ and $Ra^{t13}$ is substituted, examples of the substituent include the same group as that of $Ra^{o5}$.

In general formula (a1-r2-4), $Ra''^{14}$ is a hydrocarbon group (here, except for a phenyl group, a naphthyl group, and an anthryl group) which may have a substituent. Examples of the hydrocarbon group for $Ra''^{14}$ include the same groups (here, except for a phenyl group, a naphthyl group, and an anthryl group) as those exemplified in the description for $Ra^{t3}$ hydrocarbon group.

Examples of the substituent that $Ra''^{14}$ include the same group as the substituent that $Ra^{o4}$ may have.

Specific examples of the group represented by general formula (a1-r2-1) include as follows.

(r-pr-m1)

(r-pr-m2)

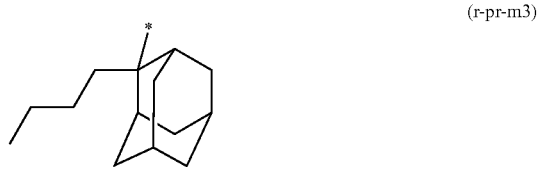

(r-pr-m3)

(r-pr-m4)

(r-pr-m5)

(r-pr-m6)

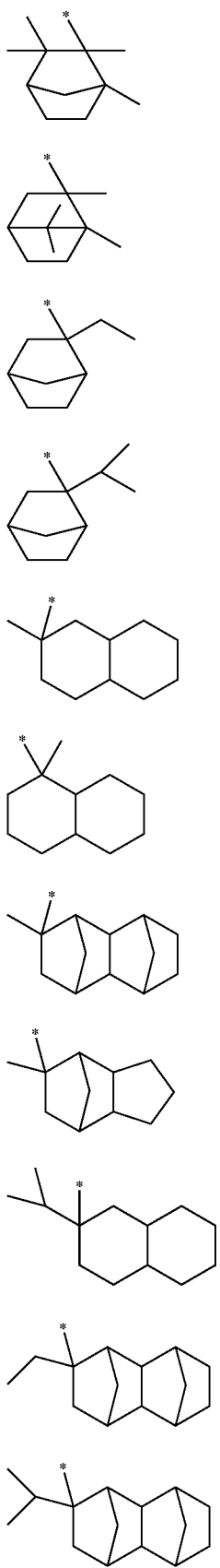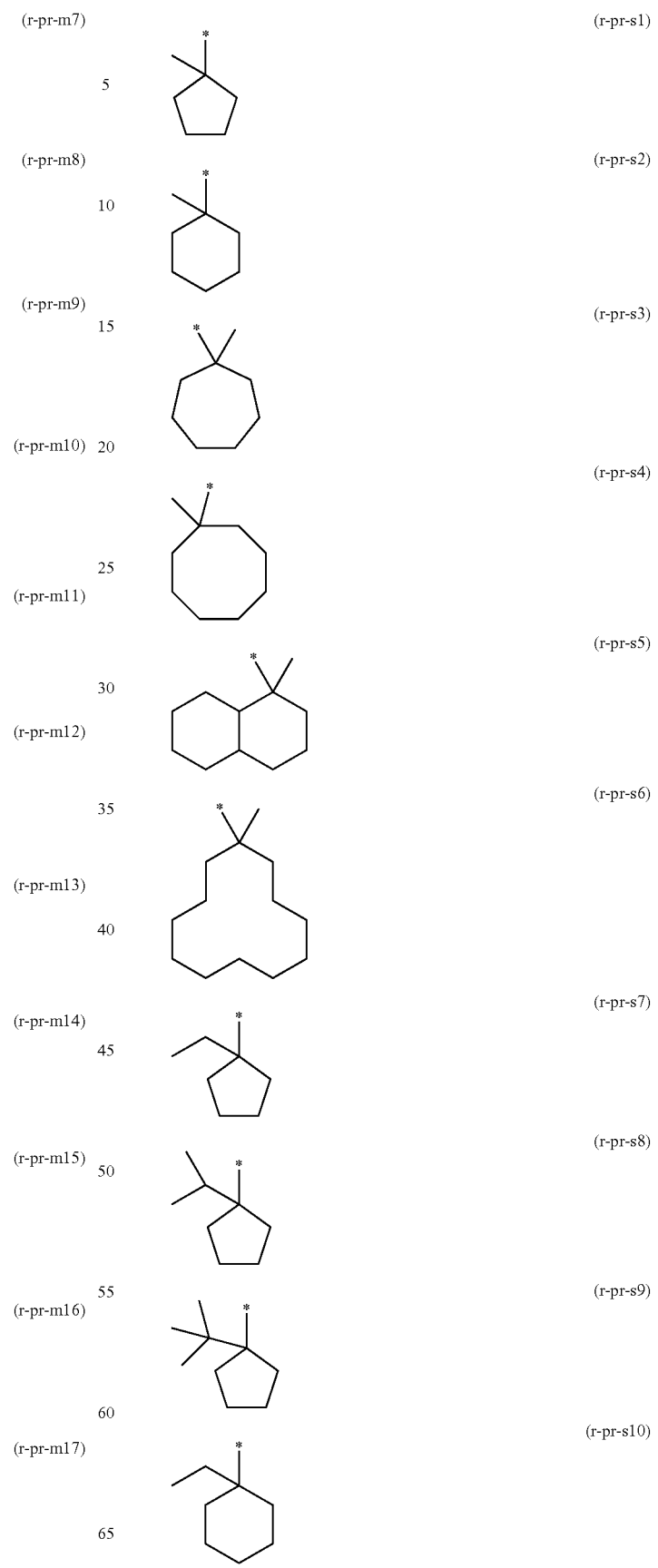

-continued
(r-pr-s11)
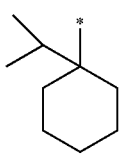
(r-pr-s12)
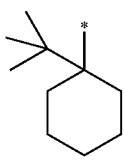
(r-pr-s13)
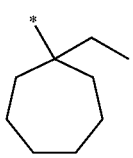
(r-pr-s14)
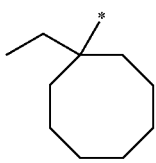
(r-pr-s15)
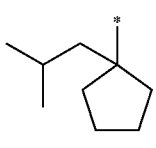
(r-pr-s16)
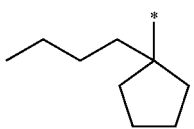
(r-pr-s17)
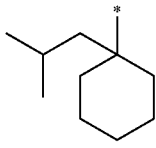
(r-pr-s18)
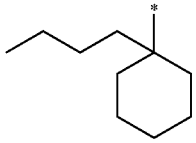
Specific examples of the group represented by general formula (a1-r2-2) include as follows.
(r-pr-sv1)
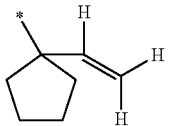
-continued
(r-pr-sv2)
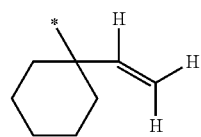
(r-pr-sv3)
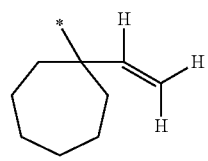
(r-pr-sv4)
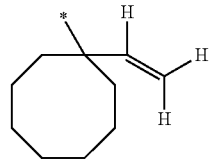
(r-pr-sv5)
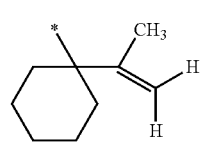
(r-pr-sv6)
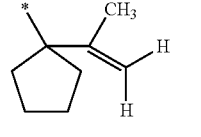
(r-pr-sv7)
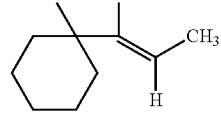
(r-pr-sv8)
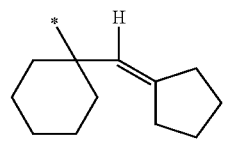
(r-pr-sv9)
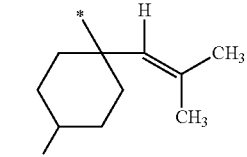
(r-pr-sv10)
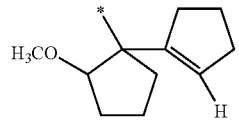
(r-pr-sv11)
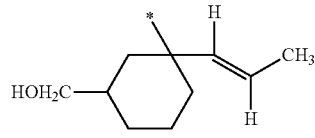

-continued
(r-pr-sv12)
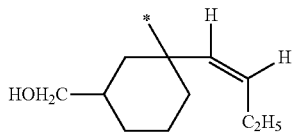
(r-pr-mv1)
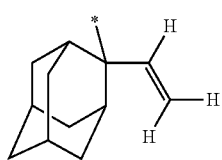
(r-pr-mv2)
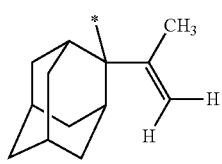
(r-pr-mv3)
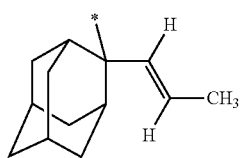
(r-pr-mv4)
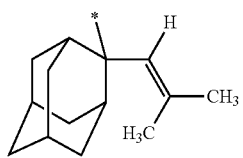
(r-pr-mv5)
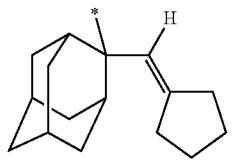
(r-pr-mv6)
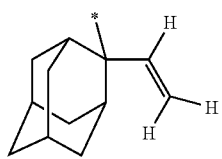
(r-pr-mv7)
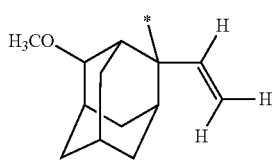
(r-pr-mv8)
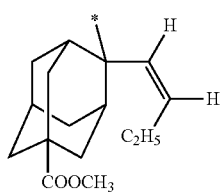
-continued
(r-pr-mv9)
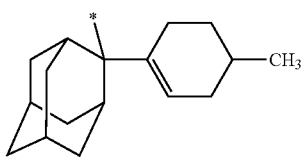
(r-pr-mv10)
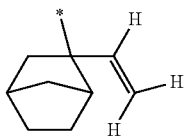
(r-pr-mv11)
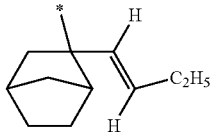
(r-pr-mv12)
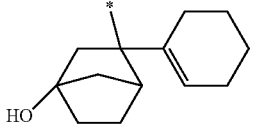
(r-p-mv-13)
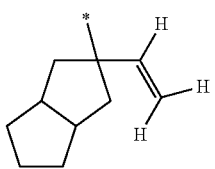
(r-pr-mv14)
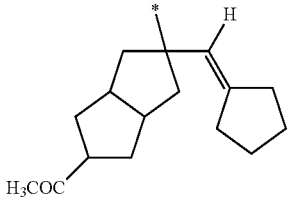
(r-pr-mv15)
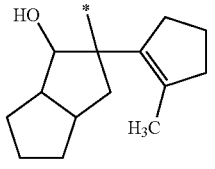
(r-pr-mv16)
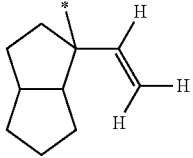
(r-pr-mv17)
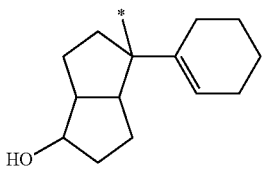

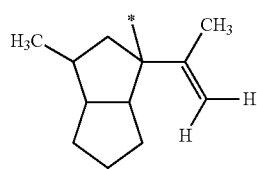 (r-pr-mv18)
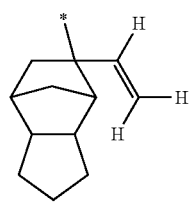 (r-pr-mv19)
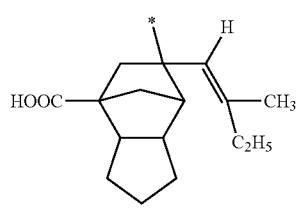 (r-pr-mv20)
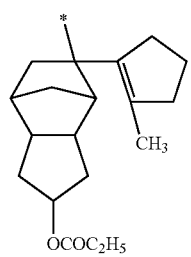 (r-pr-mv21)
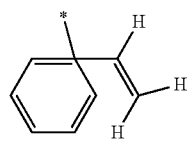 (r-pr-av1)
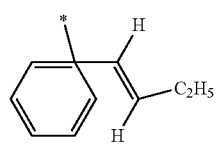 (r-pr-av2)
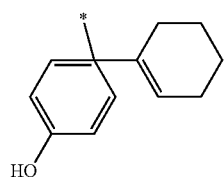 (r-pr-av3)
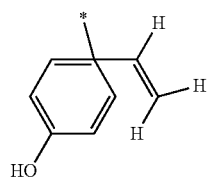 (r-pr-av4)
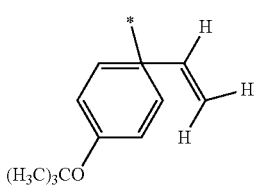 (r-pr-av5)
Specific examples of the group represented by general formula (a1-r2-3) include as follows.
 (r-pr-sa1)
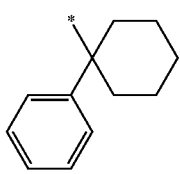 (r-pr-sa2)
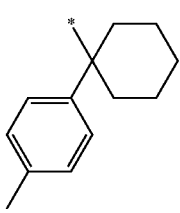 (r-pr-sa3)
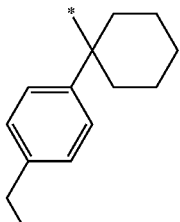 (r-pr-sa4)
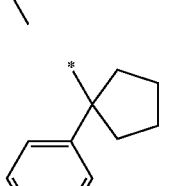 (r-pr-sa5)
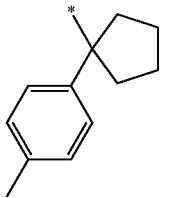 
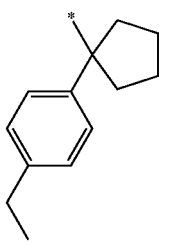 (r-pr-sa6)

-continued (r-pr-sa7)
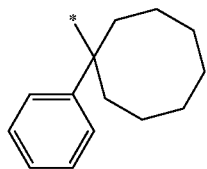

(r-pr-sa8)
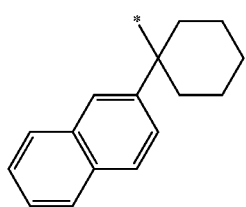

(r-pr-sa9)
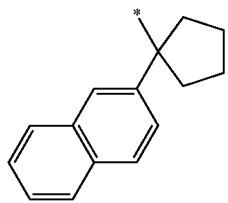

(r-pr-ma1)
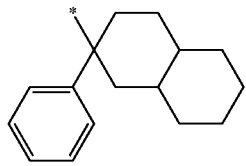

(r-pr-ma2)
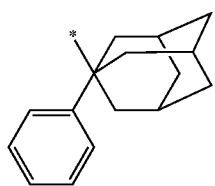

Specific examples of the group represented by general formula (a1-r2-4) include as follows.

(r-pr-cm1)
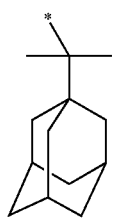

(r-pr-cm2)
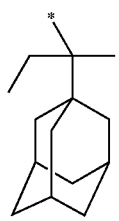

-continued (r-pr-cm3)
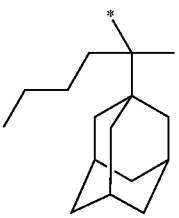

(r-pr-cm4)
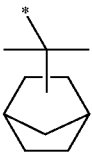

(r-pr-cs1)
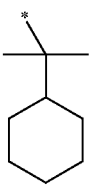

(r-pr-cs2)
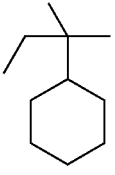

(r-pr-cs3)
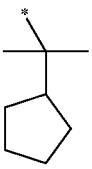

(r-pr-c1)

(r-pr-c2)

(r-pr-c3)

Tertiary Alkyloxycarbonyl Acid Dissociable Group:

Among the above-described polar groups, examples of the acid dissociable group which protects a hydroxyl group include an acid dissociable group (hereinafter, referred to as "tertiary alkyloxycarbonyl acid dissociable group" for convenience) represented by general formula (a1-r-3)

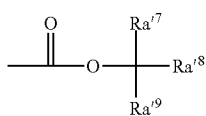
(a1-r-3)

In the formula, $Ra'^7$ to $Ra'^9$ each represent an alkyl group.

In general formula (a1-r-3), $Ra'^7$ to $Ra'^9$ each preferably represent an alkyl group having 1 to 5 carbon atoms, and further preferably 1 to 3.

In addition, a total number of carbon atoms of the respective alkyl groups is preferably 3 to 7, is further preferably 3 to 5, and is most preferably 3 and 4.

Examples of the structural unit (a1) include a structural unit derived from acrylic ester which may be obtained by substituting a hydrogen atom bonded to an α-position carbon atom with a substituent, a structural unit derived from acrylamide, a structural unit in which at least a portion of the hydrogen atoms of a hydroxyl group in the structural unit derived from a hydroxystyrene derivative or a hydroxystyrene derivative is protected by a substituent containing the acid-decomposable group, and a structural unit in which at least a portion of the hydrogen atoms in —C(=O)—OH in the structural unit derived from a vinylbenzoic acid or a vinylbenzoic acid derivative is protected by a substituent containing the acid-decomposable group.

Among them, the structural unit (a1) is preferably the structural unit derived from acrylic ester which may be obtained by substituting a hydrogen atom bonded to an α-position carbon atom with a substituent.

Specific examples of the preferred structural unit (a1) include a structural unit represented by general formula (a1-1) or (a1-2).

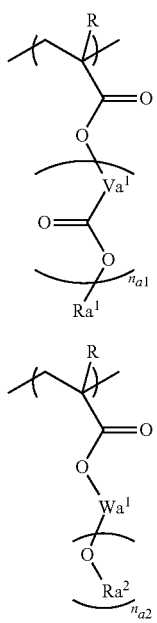

In the formula, R is a hydrogen atom, an alkyl group having 1 to 5 carbon atoms, or a halogenated alkyl group having 1 to 5 carbon atoms. $Va^1$ is a divalent hydrocarbon group which may have an ether bond, $n_{a1}$ is an integer of 0 to 2, and $Ra^1$ is an acid dissociable group represented by general formula (a1-r-1) or (a1-r-2). $Wa^1$ is ($n_{a2}$+1) valent hydrocarbon group, $n_{a2}$ is integer of 1 to 3, $Ra^2$ is an acid dissociable group represented by general formula (a1-r-1) or (a1-r-3).

In general formula (a1-1), an alkyl group having 1 to 5 carbon atoms of R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. A halogenated alkyl group having 1 to 5 carbon atoms is a group obtained by substituting at least one hydrogen atom of an alkyl group having 1 to 5 carbon atoms with a halogen atom. Examples of the halogen atom include a fluorine atom, a chlorine atom, a bromine atom, and an iodine atom, and the fluorine atom is particularly preferable.

R is preferably a hydrogen atom, an alkyl group having 1 to 5 carbon atoms, or a fluorinated alkyl group having 1 to 5 carbon atoms, and a hydrogen atom or a methyl group is most preferable in terms of industrial availability.

In general formula (a1-1), the divalent hydrocarbon group for $Va^1$ may be an aliphatic hydrocarbon group, and may be an aromatic hydrocarbon group.

The aliphatic hydrocarbon group for $Va^1$ as the divalent hydrocarbon group may be saturated or unsaturated, and is usually preferably saturated.

Specific examples of the aliphatic hydrocarbon group include a linear or branched aliphatic hydrocarbon group, or an aliphatic hydrocarbon group including a ring in the structure.

The number of carbon atoms of the linear aliphatic hydrocarbon group is preferably 1 to 10, is further preferably 1 to 6, is further still preferably 1 to 4, and is most preferably 1 to 3.

As the linear aliphatic hydrocarbon group, a linear alkylene group is preferable, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The number of carbon atoms of the branched aliphatic hydrocarbon group is preferably 3 to 10, is further preferably 3 to 6, is still further preferably 3 or 4, and is most preferably 3.

As the branched aliphatic hydrocarbon group, a branched chain alkylene group is preferable, and specific examples thereof include an alkylalkylene group such as an alkyl methylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; an alkyl ethylene group such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; an alkyl trimethylene group such as —$CH(CH_3)CH_2CH_2$— and —$CH_2CH(CH_3)CH_2$—; an alkyl tetramethylene group such as —$CH(CH_3)CH_2CH_2CH_2$— and —$CH_2CH(CH_3)CH_2CH_2$—. As an alkyl group in the alkylalkylene group, a linear alkyl group having 1 to 5 carbon atoms is preferable.

Examples of the aliphatic hydrocarbon group including a ring in the structure include an alicyclic hydrocarbon group (a group obtained by removing two hydrogen atoms from the aliphatic hydrocarbon ring), a group in which an alicyclic hydrocarbon group is bonded to the terminal of the linear or branched aliphatic hydrocarbon group, and a group in which an alicyclic hydrocarbon group is interposed in the middle of the linear or branched aliphatic hydrocarbon group. The examples of the linear or branched aliphatic hydrocarbon group include the same group as the linear aliphatic hydrocarbon group or the branched aliphatic hydrocarbon group.

The number of carbon atoms of the alicyclic hydrocarbon group is preferably 3 to 20, and is further preferably 3 to 12.

The alicyclic hydrocarbon group may be polycyclic or monocyclic. As the monocyclic alicyclic hydrocarbon group, a group obtained by removing two hydrogen atoms from monocycloalkane is preferable. The number of carbon atoms of the monocycloalkane is preferably 3 to 6, and specifically, examples of the monocycloalkane include cyclopentane and cyclohexane. As the polycyclic alicyclic hydrocarbon group, a group obtained by removing two hydrogen atoms from polycycloalkane is preferable, and a group having 7 to 12 carbon atoms is preferably as the polycycloalkane. Specifically, examples thereof include adamantane, norbornane, isobornane, tricyclodecane, and tetracyclododecane.

The aromatic hydrocarbon group as the divalent hydrocarbon group for $Va^1$ is a hydrocarbon group having an aromatic ring.

The number of carbon atoms of the aromatic hydrocarbon group is preferably 3 to 30, is further preferably 5 to 30, is still further preferably 5 to 20, is particularly preferably 6 to 15, and is most preferably 6 to 10. Here, it is assumed that the number of carbon atoms does not include the number of carbon atoms in the substituent.

Specific examples of the aromatic ring having an aromatic hydrocarbon group include an aromatic hydrocarbon ring such as benzene, biphenyl, fluorene, naphthalene, anthracene, and phenanthrene; and aromatic heterocycle in which a portion of the carbon atoms which constitute the aromatic hydrocarbon ring is substituted with a heteroatom. Examples of the heteroatom in the aromatic heterocycle include an oxygen atom, a sulfur atom, and a nitrogen atom.

Specific examples of the aromatic hydrocarbon group include a group (an arylene group) obtained by removing two hydrogen atoms from the above-mentioned aromatic hydrocarbon ring; and a group in which one hydrogen atom of a group (an aryl group) obtained by removing one hydrogen atom from the above-mentioned aromatic hydrocarbon ring is substituted with an alkylene group (for example, a group obtained by in which one hydrogen atom is removed from an aryl group in an aryl alkyl group such as a benzyl group, a phenethyl group, a 1-naphthyl methyl group, a 2-naphthyl methyl group, a 1-naphthyl ethyl group, and a 2-naphthyl ethyl group). The number of carbon atoms of the alkylene group (an alkyl chain in the aryl alkyl group) is preferably 1 to 4, is further preferably 1 and 2, and is particularly preferably 1.

In general formula (a1-1), $Ra^1$ is an acid dissociable group represented by general formula (a1-r-1) or (a1-r-2).

In general formula (a1-2), the $(n_{a2}+1)$ valent hydrocarbon group for $Wa^1$ may be an aliphatic hydrocarbon group, or may be an aromatic hydrocarbon group. The aliphatic hydrocarbon group means a hydrocarbon group having no aromaticity, and may be saturated or unsaturated, and generally it is preferably saturated. Examples of the aliphatic hydrocarbon group include a linear or branched aliphatic hydrocarbon group, an aliphatic hydrocarbon group containing a ring in the structure, and a group in which a linear or branched aliphatic hydrocarbon group and the aliphatic hydrocarbon group containing the ring in the structure is combined with each other.

The $(n_{a2}+1)$ valent is preferably to be divalent to tetravalent, and is further preferably to be divalent or trivalent.

Hereinafter, specific examples of the structural unit represented by general formula (a1-1) will be described. In the following formulae, $R^\alpha$ represents a hydrogen atom, a methyl group, or a trifluoromethyl group.

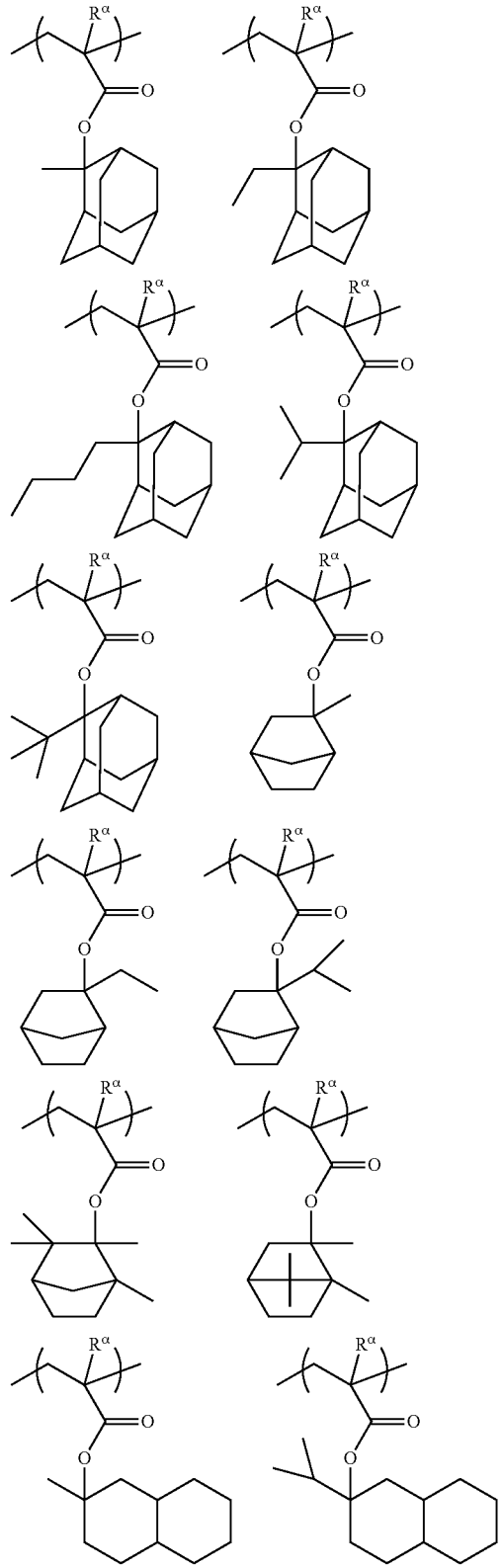

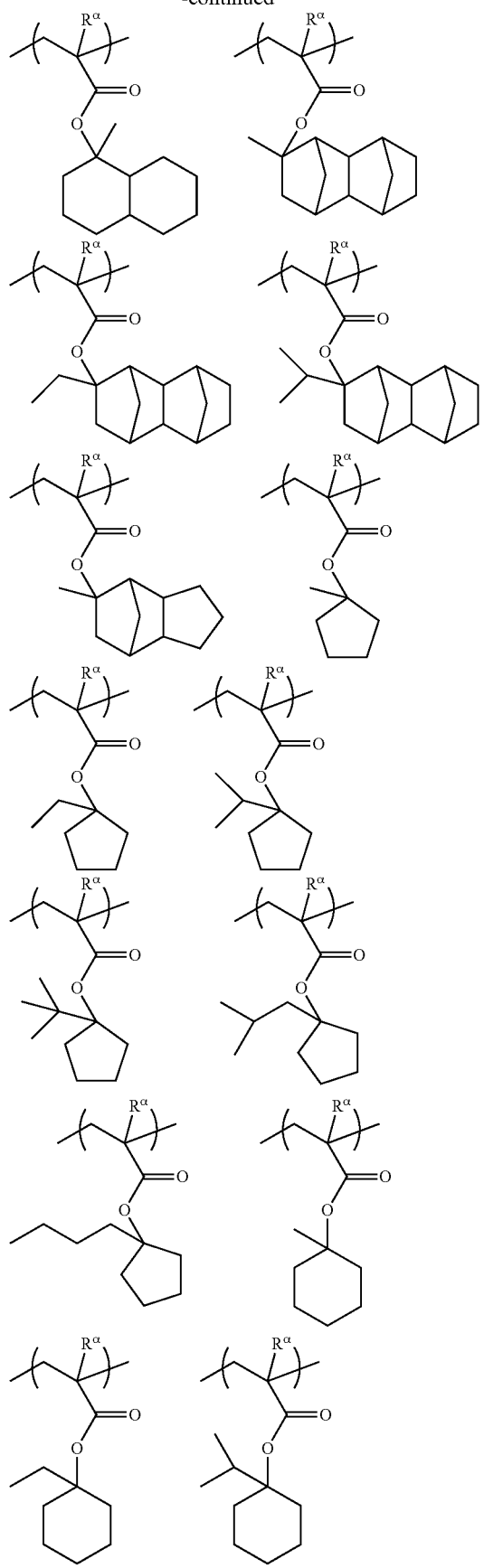
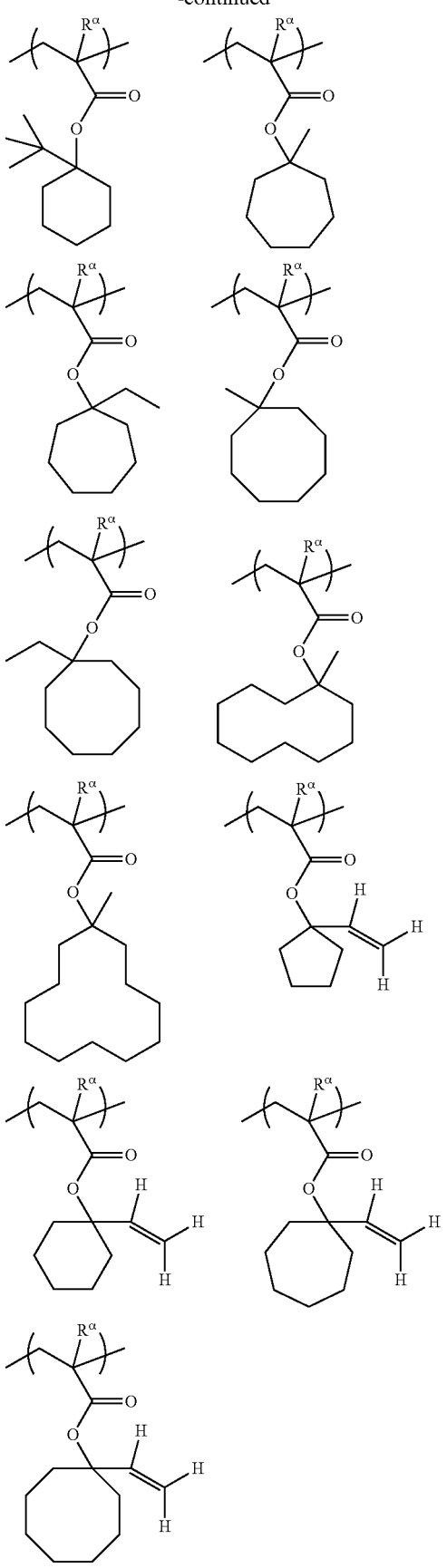

-continued
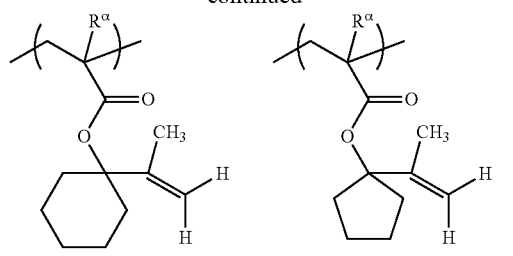
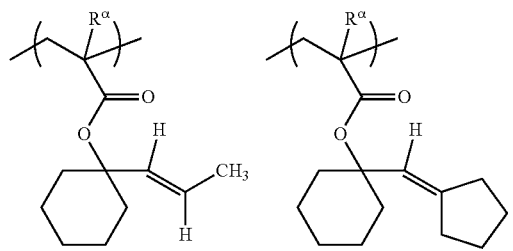
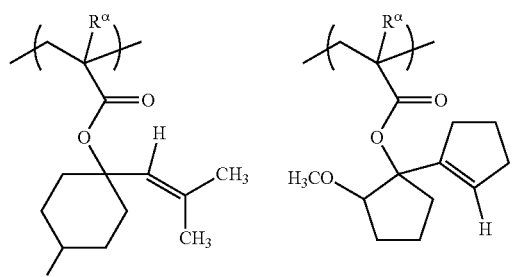
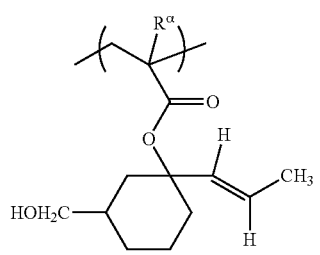
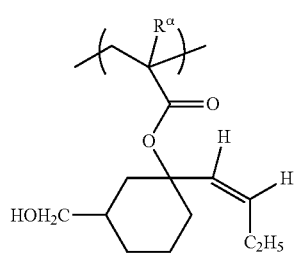
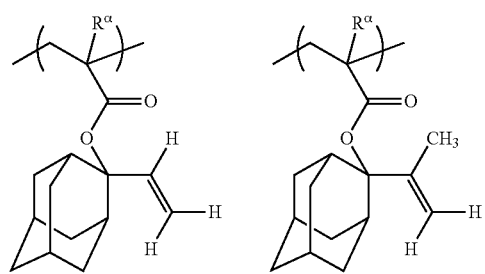
-continued
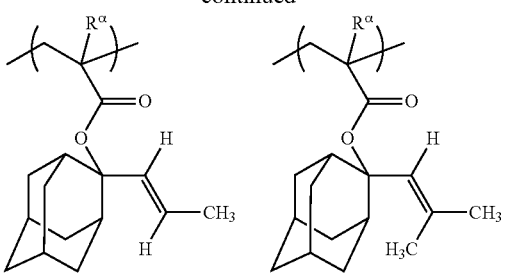
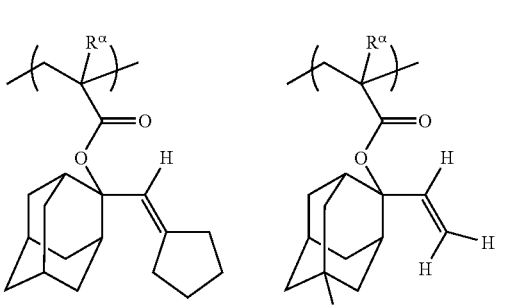
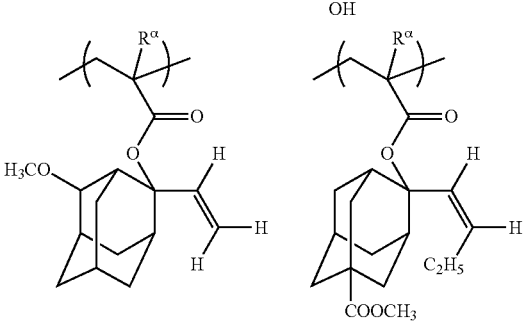
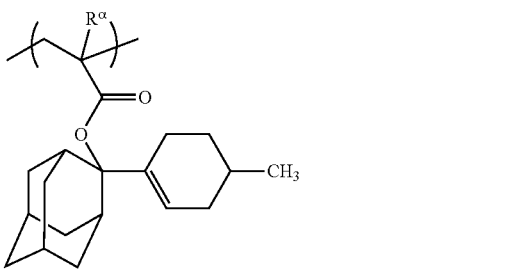
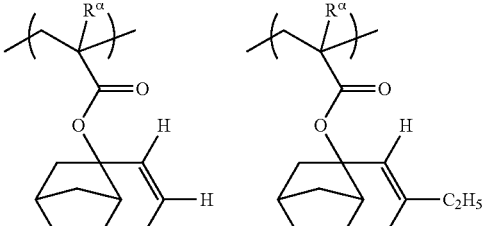
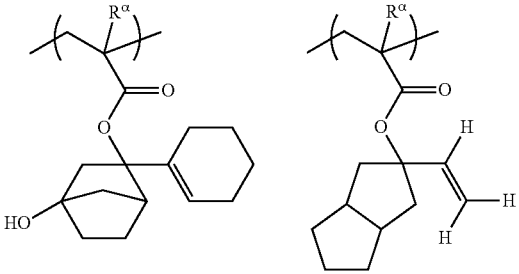

-continued
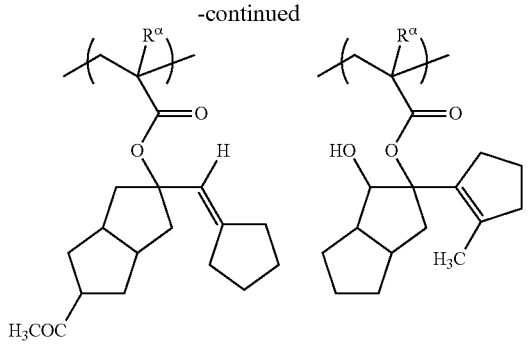 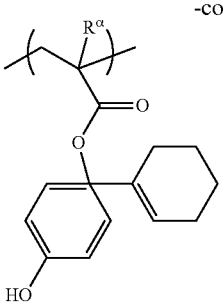 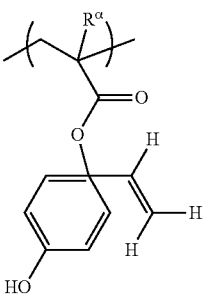
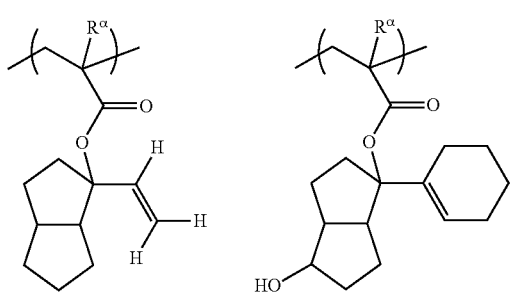 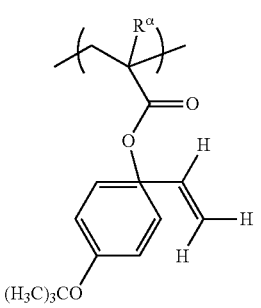
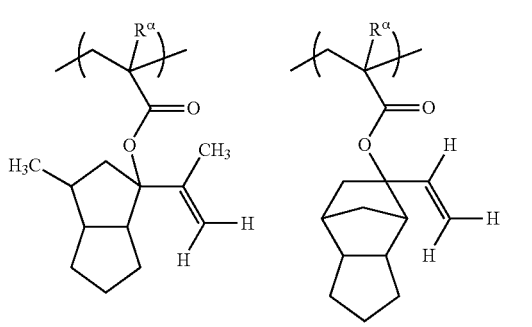 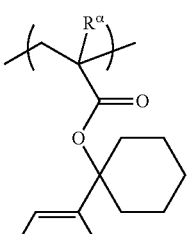 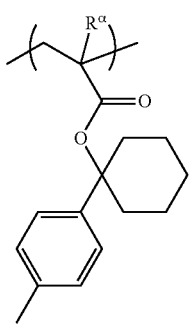
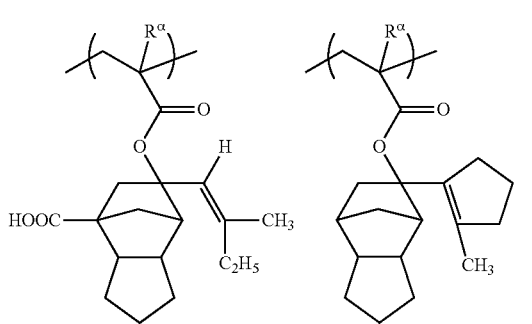 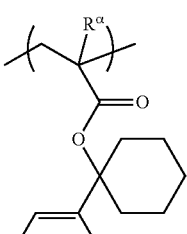
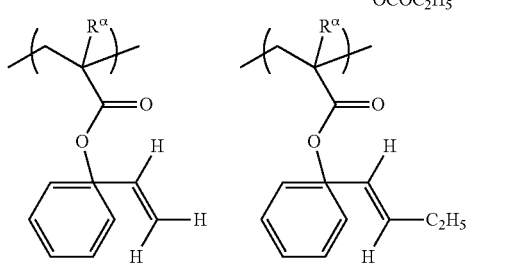 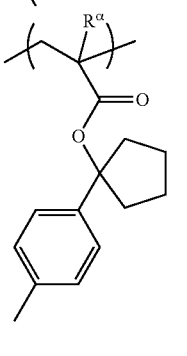 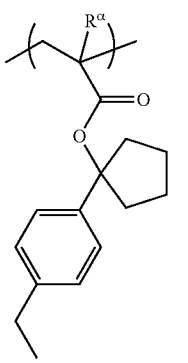

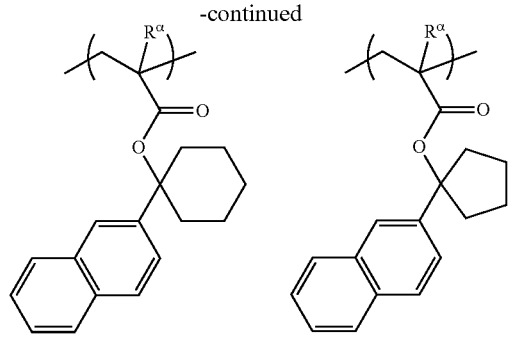
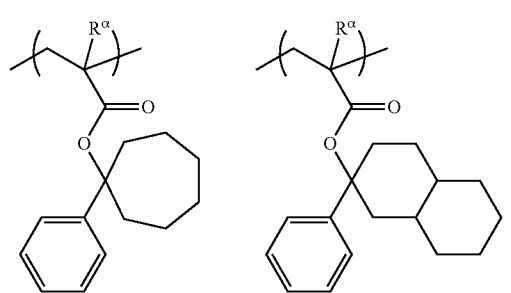
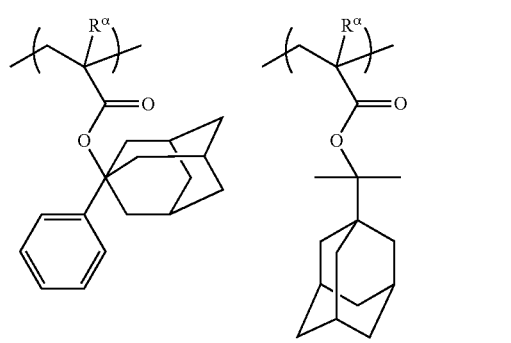
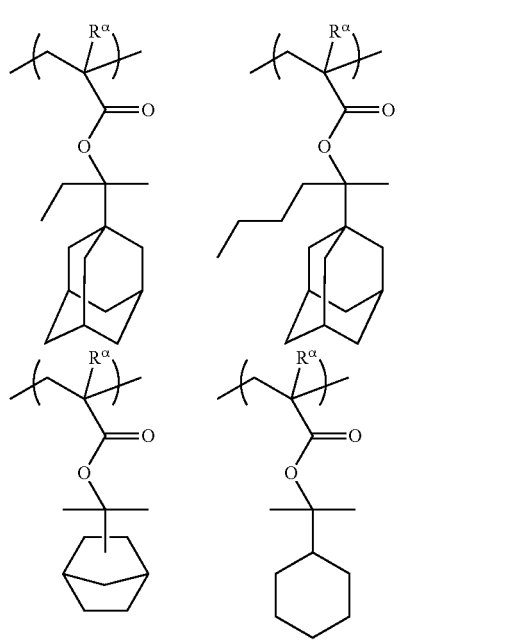
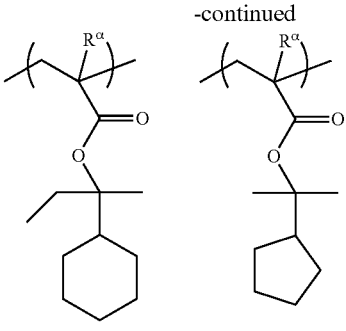
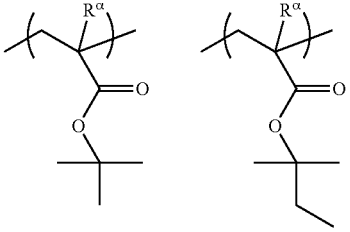
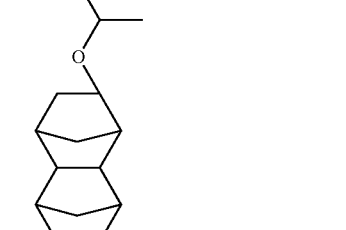
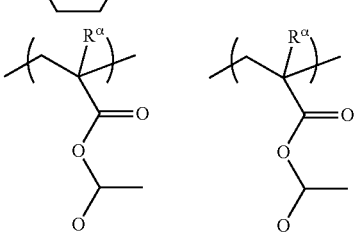
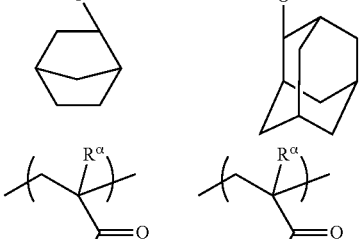
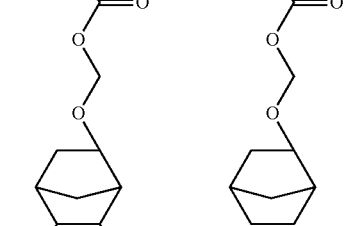

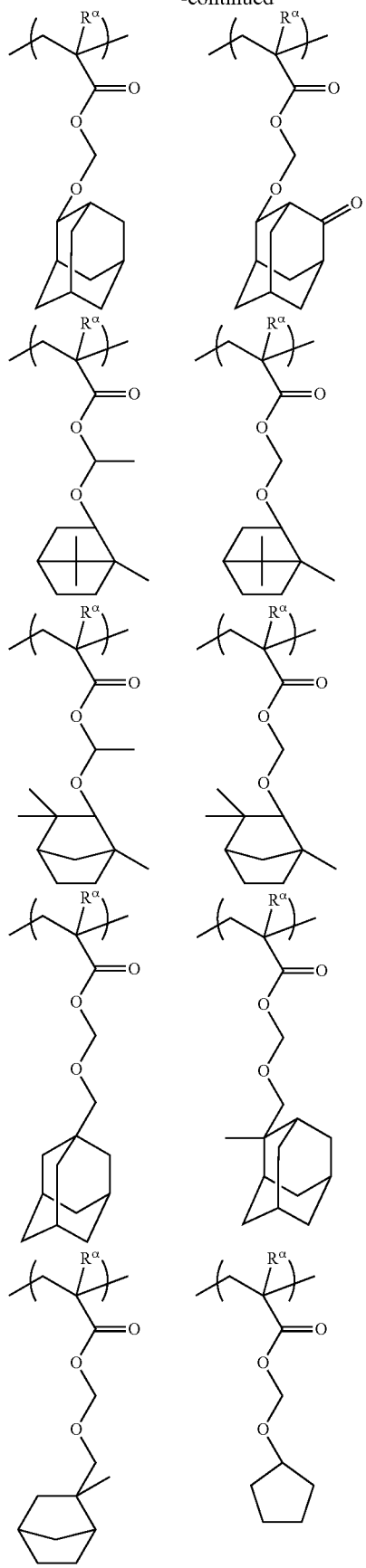
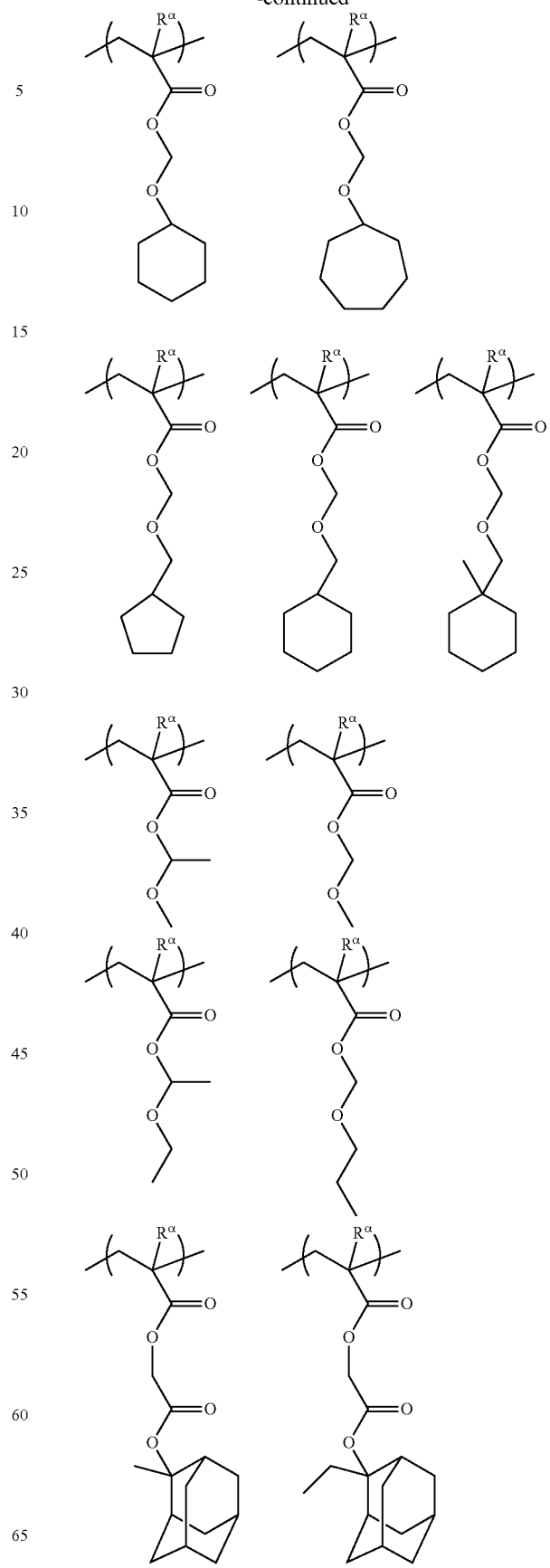

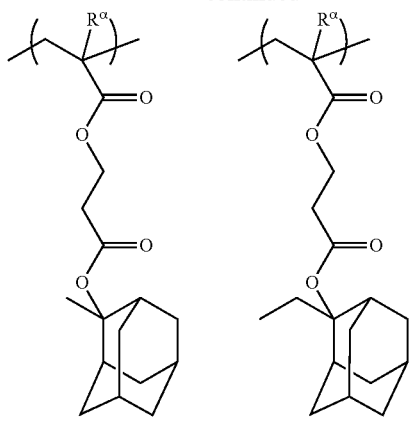
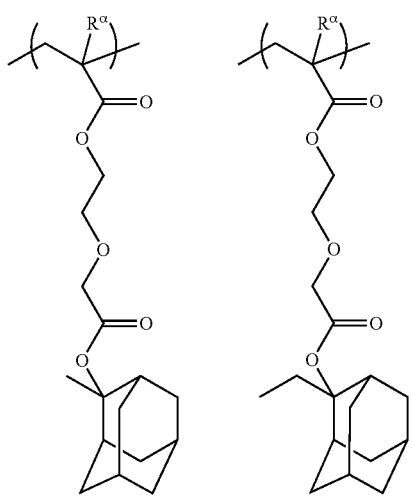
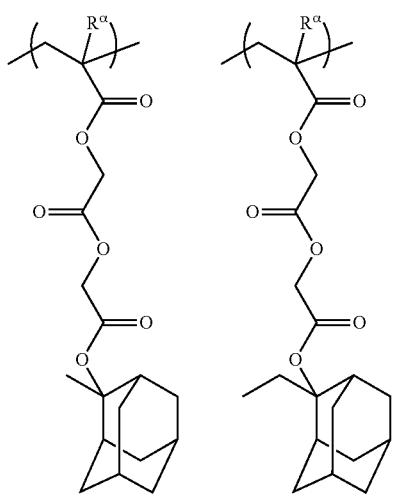
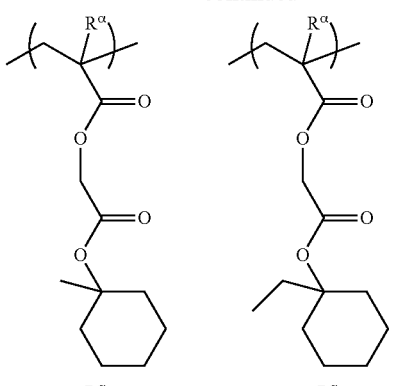
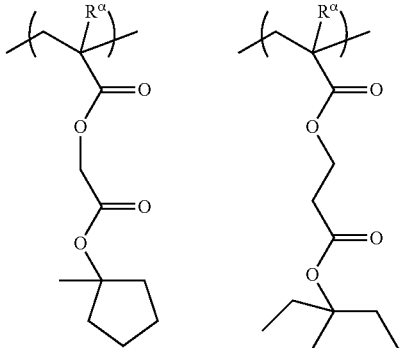
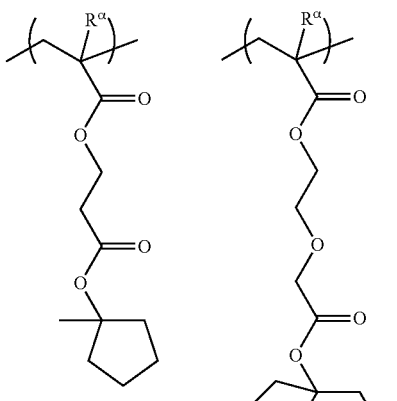
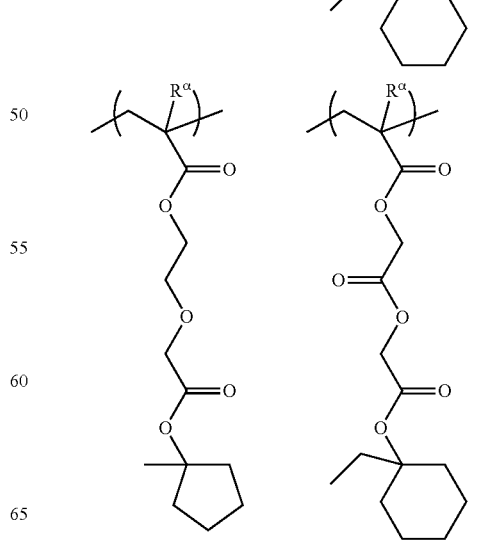

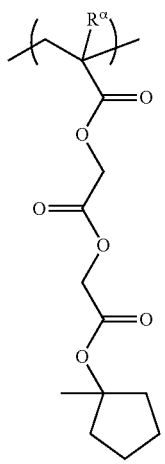

Specific examples of the structural unit represented by general formula (a1-2) will be described.

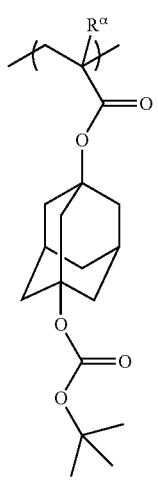 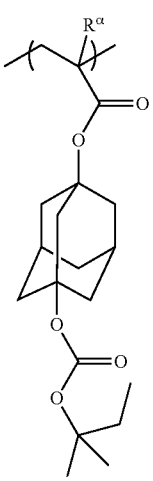 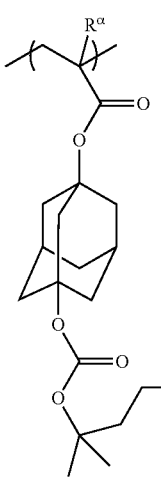

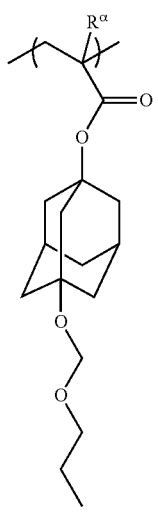 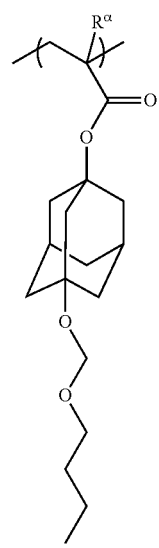

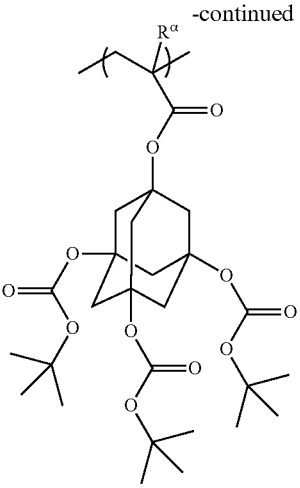

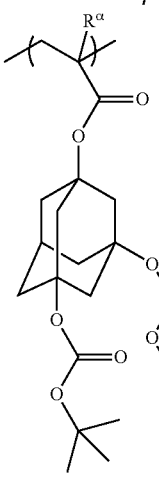 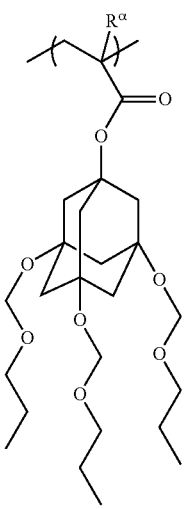

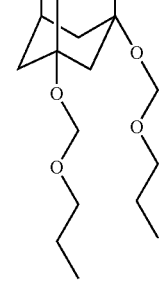

The structural unit (a1) of the (A1) component may be used alone, or two or more kinds thereof may be used in combination.

From the viewpoint that the properties of the lithography (sensitivity, shape, and the like) by electron beam and EUV are more likely to be enhanced, the structural unit (a1) is further preferably a structural unit represented by general formula (a1-1).

The ratio of the structural unit (a1) in the (A1) component is preferably 20 to 70 mol %, is further preferably 25 to 65 mol %, and is still further preferably 30 to 60 mol %, with respect to the total (100 mol %) of the entire structural units for constituting the (A1) component.

When the ratio of the structural unit (a1) is set to be equal to or greater than the lower limit value, it is possible to easily obtain a resist pattern, and the lithography properties such as sensitivity, resolution, and roughness improvement are also improved. In addition, when the ratio of the structural unit (a1) is set to be equal to or lower the upper limit, it is possible to take balance with other structural units.

In the resist composition of the present embodiment, the (A) component contains a polymer compound (A1-1) having the structural unit (a0) (hereinafter, also referred to as "(A1-1) component").

The (A1) component contained in the resist composition may be used alone or two or more kinds thereof may be used in combination.

Preferred examples of the (A1-1) component include a polymer compound having a repeated structure of the structural unit (a0) and the structural unit (a2); a polymer compound having a repeated structure of the structural unit (a0), the structural unit (a2), and the structural unit (a9) (hereinafter, also referred to as "(A1-1-1) component"); and a polymer compound having a repeated structure of the structural unit (a0) and the structural unit (a10) (hereinafter, also referred to as "(A1-1-2) component").

In the resist composition of the present embodiment, as the (A) component, the (A1-1-1) component and the (A1-1-2) component are preferably used be used in combination.

In the (A1-1-1) component, the ratio of the structural unit (a0) is preferably with respect to 20 to 70 mol %, is further preferably 25 to 65 mol %, and is still further preferably 30 to 60 mol %, with respect to the entire structural units (100 mol %) forming the (A1-1-1) component.

The ratio of the structural unit (a2) is preferably 20 to 70 mol %, is further preferably 25 to 65 mol %, and is still further preferably 30 to 60 mol %, with respect to the total ratio (100 mol %) of the entire structural units for constituting the (A1-1-1) component.

The ratio of the structural unit (a9) is preferably 1 to 40 mol %, is further preferably 3 to 30 mol %, and is still further preferably 5 to 25 mol %, with respect to the total ratio (100 mol %) of the entire structural units for constituting the (A1-1-1) component.

In the (A1-1-2) component, the ratio of the structural unit (a0) is preferably 25 to 75 mol %, is further preferably 30 to 70 mol %, and is still further preferably 35 to 65 mol %, with respect to the total ratio (100 mol %) of the entire structural units for constituting the (A1-1-2) component.

The ratio of the structural unit (a10) is preferably 25 to 75 mol %, is further preferably 30 to 70 mol %, and is still further preferably 35 to 65 mol %, with respect to the total ratio (100 mol %) of the entire structural units for constituting the (A1-1-2) component.

Regarding the ratio (mass ratio) of the (A1-1-1) component to the (A1-1-2) component, (A1-1-1) component/(A1-1-2) component is preferably 1/9 to 9/1, is further preferably 3/7 to 7/3, and still further preferably 5/5.

The mass average molecular weight (Mw) (in terms of the standard polystyrene by gel permeation chromatography (GPC)) of the component (A1-1) is not particularly limited, and is preferably about 1,000 to 50,000, is and is further preferably about 2,000 to 30,000, and is still further preferably about 3,000 to 20,000.

When the Mw of the component (A1-1) is equal to or less than the preferred upper limit, the solubility with respect to a resist solvent is sufficient in the case where the component (A1-1) is used as a resist, and when the Mw of the component (A1-1) is equal to or greater than the preferred lower limit, dry etching resistance and a resist pattern cross-sectional shape are improved.

The dispersivity (Mw/Mn) of the component (A1-1) is not particularly limited, and is preferably about 1.0 to 4.0, is further preferably about 1.0 to 3.0, and is particularly preferably about 1.5 to 2.5. Note that, Mn represents a number average molecular weight.

The ratio of the component (A1-1) in the component (A) is preferably 25% by mass or more, is further preferably 50% by mass or more, is still further preferably 75% by mass or more, and may be 100% by mass, with respect to the total mass of the component (A). When the aforementioned ratio is 25% by mass or more, it is easy to form a resist pattern which is excellent in other lithography properties such as high sensitivity and the improved roughness. Such effects are particularly remarkable in the lithography by electron beams and EUV.

Method for Preparing (A1) Component:

The (A1) component can be prepared by dissolving a monomer which derives each structural unit into a polymerization solvent, and adding a radical polymerization initiator such as azobisisobutyronitrile (AIBN), and dimethyl 2,2'-azobisisobutyrate (for example, V-601) to the solvent so as to perform polymerization. At the time of the polymerization, a —C(CF$_3$)$_2$—OH group may be introduced to a terminal by using a chain transfer agent such as HS—CH$_2$—CH$_2$—CH$_2$—C(CF$_3$)$_2$—OH in combination. As such, a copolymer to which a hydroxyalkyl group in which a portion of the hydrogen atoms of an alkyl group is substituted with a fluorine atom is introduced is effective in decreasing development defects and line edge roughness (LER: non-uniform irregularities of the line side walls).

In the resist composition of the present embodiment, the (A) component may be used alone, or two or more kinds thereof may be used in combination.

In the resist composition of the present embodiment, the content of the (A) component may be adjusted in accordance with a film thickness of a resist film to be formed.

(B) Component

A (B) component is an acid generator component which generates an acid upon exposure.

(B1) Component

In the resist composition of the present embodiment, the (B) component includes compound (B1) (hereinafter, also referred to as "(B) component") represented by general formula (b1).

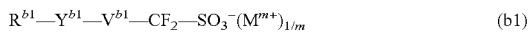

$$R^{b1}-Y^{b1}-V^{b1}-CF_2-SO_3^-(M^{m+})_{1/m} \quad (b1)$$

In general formula (b1), $R^{b1}$ represents a cyclic hydrocarbon group which may have a substituent. $Y^{b1}$ represents a divalent linking group containing an ester bond (—C(=O)—O— or —O—C(=O)—). $V^{b1}$ represents an alkylene group, a fluorinated alkylene group, or a single bond. m is an integer of 1 or more, and $M^{m+}$ is an m-valent organic cation.

Anion Part ($R^{b1}$—$Y^{b1}$—$V^{b1}$—$SO_3^-$)

In general formula (b1), $R^{b1}$ represents a cyclic hydrocarbon group which may have a substituent.

The cyclic hydrocarbon group for $R^{b1}$ may be an aromatic hydrocarbon group, or may be an aliphatic hydrocarbon group. The aliphatic hydrocarbon group means a hydrocarbon group having no aromaticity.

Further, the aliphatic hydrocarbon group may be saturated or unsaturated, and is usually preferably saturated.

The aromatic hydrocarbon group for $R^{b1}$ is a hydrocarbon group having an aromatic ring. The number of carbon atoms of the aromatic hydrocarbon group is preferably 3 to 30, is further preferably 5 to 30, is still further preferably 5 to 20, is particularly preferably 6 to 15, and is most preferably 6 to 10. Here, it is assumed that the number of carbon atoms does not include the number of carbon atoms in the substituent.

Specific examples of an aromatic ring having an aromatic hydrocarbon group for $R^{b1}$ include benzene, fluorene, naphthalene, anthracene, phenanthrene, biphenyl, or an aromatic heterocycle in which a portion of carbon atoms constituting these aromatic rings is substituted with heteroatoms. Examples of the heteroatom in the aromatic heterocycle include an oxygen atom, a sulfur atom, and a nitrogen atom.

Specific examples of the aromatic hydrocarbon group for $R^{b1}$ include a group obtained by removing one hydrogen atom from the aromatic ring (aryl group: for example, a phenyl group and a naphthyl group), a group in which one hydrogen atom of the aromatic ring is substituted with an alkylene group (for example, an aryl alkyl group such as a benzyl group, a phenethyl group, a 1-naphtyl methyl group, a 2-naphtyl methyl group, a 1-naphtyl ethyl group, and a 2-naphtyl ethyl group). The number of carbon atoms of the alkylene group (an alkyl chain in an aryl alkyl group) is preferably 1 to 4, is more preferably 1 to 2, and is particularly preferably 1.

Examples of the cyclic aliphatic hydrocarbon group for $R^{b1}$ include an aliphatic hydrocarbon group including a ring in a structure.

Examples of the aliphatic hydrocarbon group including a ring in this structure include an alicyclic hydrocarbon group (a group obtained by removing one hydrogen atom from an aliphatic hydrocarbon ring), a group in which an alicyclic hydrocarbon group is bonded to a terminal of a linear or branched aliphatic hydrocarbon group, and a group in which an alicyclic hydrocarbon group is present in the middle of the linear or branched aliphatic hydrocarbon group.

The number of carbon atoms of the alicyclic hydrocarbon group is preferably 3 to 20, and is further preferably 3 to 18.

The alicyclic hydrocarbon group may be a polycyclic group, or may be a monocyclic group. As the monocyclic alicyclic hydrocarbon group, a group obtained by removing one or more hydrogen atoms from the monocycloalkane is preferable. As the monocycloalkane, a group having 3 to 6 carbon atoms is preferable, and specific examples thereof include cyclopentane and cyclohexane. As the polycyclic alicyclic hydrocarbon group, a group obtained by removing one or more hydrogen atoms from the polycycloalkane is preferable, and as the polycycloalkane, a group having 7 to 30 carbon atoms is preferable. Among them, as polycycloalkane, polycycloalkane having a bridged ring polycyclic skeleton such as adamantane, norbornane, isobornane, tricyclodecane, and tetracyclododecene; and polycycloalkane having a condensed ring-based polycyclic skeleton such as a cyclic group having a steroid skeleton is further preferable.

Among them, as the cyclic aliphatic hydrocarbon group for $R^{b1}$, a group obtained by removing one or more hydrogen atom from monocycloalkane or polycycloalkane is preferable, and a group obtained by excluding one hydrogen atom from polycycloalkane is further preferable.

The number of carbon atoms of a linear aliphatic hydrocarbon group that may be bonded to an alicyclic hydrocarbon group is preferably 1 to 10, is further preferably 1 to 6, is further still preferably 1 to 4, and is most preferably 1 to 3. As a linear aliphatic hydrocarbon group, a linear alkylene group is preferable, and specific examples include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The number of carbon atoms of a branched aliphatic hydrocarbon group that may be bonded to an alicyclic hydrocarbon group is preferably 2 to 10, is further preferably 3 to 6, is further still preferably 3 or 4, and is most preferably 3. As a branched aliphatic hydrocarbon group, a branched alkylene group is preferable, and specific examples thereof include an alkyl alkylene group such as an alkyl methylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; an alkyl ethylene group such as —$CH(CH_3)CH_2$—, —$CH(CH_3)CH(CH_3)$—, —$C(CH_3)_2CH_2$—, —$CH(CH_2CH_3)CH_2$—, —$C(CH_2CH_3)_2$—$CH_2$—; an alkyltrimethylene group such as —$CH(CH_3)CH_2CH_2$— and —$CH_2CH(CH_3)CH_2$—; and an alkyltetramethylene group such as —$CH(CH_3)CH_2CH_2CH_2$— and —$CH_2CH(CH_3)CH_2CH_2$—. As an alkyl group in an alkyl alkylene group, a linear alkyl group having 1 to 5 carbon atoms is preferable.

Examples of the substituents that the cyclic hydrocarbon group for $R^{b1}$ include an alkyl group, an alkoxy group, a halogen atom, a halogenated alkyl group, a hydroxyl group, a carbonyl group, and a nitro group.

The alkyl group as a substituent is preferably an alkyl group having 1 to 5 carbon atoms, and is most preferably a methyl group, an ethyl group, a propyl group, an n-butyl group, and a tert-butyl group.

The alkoxy group as a substituent is preferably an alkoxy group having 1 to 5 carbon atoms, is further preferably a methoxy group, an ethoxy group, an n-propoxy group, an iso-propoxy group, an n-butoxy group, and a tert-butoxy group, and is most preferably a methoxy group and an ethoxy group.

Examples of the halogen atom as a substituent include a fluorine atom, a chlorine atom, a bromine atom, and an iodine atom, and among them, the fluorine atom is preferable.

Examples of the halogenated alkyl group as a substituent include an alkyl group having 1 to 5 carbon atoms, for example, a group in which at least one hydrogen atom such as a methyl group, an ethyl group, a propyl group, an n-butyl group, and a tert-butyl group is substituted with a halogen atom.

A carbonyl group as a substituent is a group in which a methylene group (—$CH_2$—) constituting a cyclic hydrocarbon group is substituted.

Among them, $R^{b1}$ is preferably a cyclic aliphatic hydrocarbon group which may have a substituent. More specifically, a group obtained by removing one or more hydrogen atoms from polycycloalkane which may have a substituent is preferable.

Hereinafter, specific examples of $R^{b1}$ in general formula (b1) will be described. A symbol of * represents a bond.

($R^{b1}$-1)

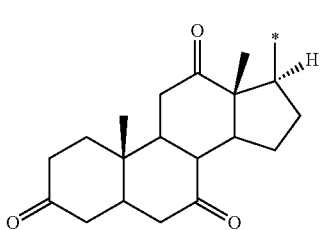

(R$^{b1}$-2)

In general formula (b1), Y$^{b1}$ represents a divalent linking group containing an ester bond (—C(=O)—O— or —O—C(=O)—).

Examples of the divalent linking group containing an ester bond include an ester bond (—C(=O)—O— or —O—C(=O)—), and a combination of an ester bond and an alkylene group.

In addition, Y$^{b1}$ may a non-hydrocarbon-based oxygen atom-containing linking group such as an oxygen atom (ether bond: —O—), an ester bond (—C(=O)—O—), an oxycarbonyl group (—O—C(=O)—), an amino bond (—C(=O)—NH—), a carbonyl group (—C(=O)—), a carbonate bond (—O—C(=O)—O—), and a sulfonyl group (—SO$_2$—) in addition to an ester bond.

Examples of the divalent linking group containing the ester bond include linking groups represented by general formulae (y-al-1) to (y-al-3), (y-al-5), and (y-al-7).

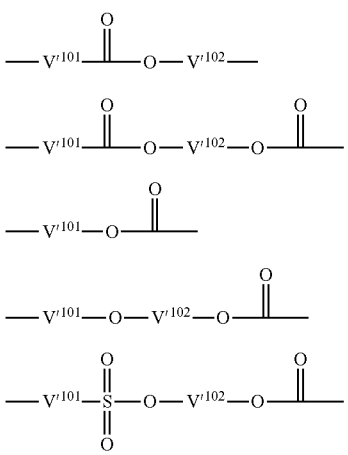

In the formula, V'$^{101}$ is a single bond or an alkylene group having 1 to 5 carbon atoms, and V'$^{102}$ is a divalent saturated hydrocarbon group having 1 to 30 carbon atoms.

The divalent saturated hydrocarbon group for V'$^{102}$ is preferably an alkylene group having 1 to 30 carbon atoms, is further preferably an alkylene group having 1 to 10 carbon atoms, and is still further preferably an alkylene group having 1 to 5 carbon atoms.

The alkylene group for V'101 and V'$^{102}$ may be a linear alkylene group or a branched alkylene group, and is preferably a linear alkylene group.

Specific examples of the alkylene group for V'$^{101}$ and V'$^{102}$ include a methylene group [—CH$_2$—]; an alkyl methylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; an ethylene group [—CH$_2$CH$_2$—]; an alkyl ethylene group such as —CH(CH$_3$)CH$_2$—, —CH(CH$_3$)CH(CH$_3$)—, —C(CH$_3$)$_2$CH$_2$—, and —CH(CH$_2$CH$_3$)CH$_2$—; a trimethylene group (an n-propylene group) [—CH$_2$CH$_2$CH$_2$—]; alkyl trimethylene group such as —CH(CH$_3$)CH$_2$CH$_2$—, and —CH$_2$CH(CH$_3$)CH$_2$—; a tetramethylene group [—CH$_2$CH$_2$CH$_2$CH$_2$—]; an alkyl tetramethylene group such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—].

Further, a portion of methylene groups in the alkylene group for V'$^{101}$ or V'$^{102}$ may be substituted with a divalent aliphatic cyclic group having 5 to 10 carbon atoms. The aliphatic cyclic group is preferably a divalent group obtained by further removing one hydrogen atom from a cyclic aliphatic hydrocarbon group (a monocyclic aliphatic hydrocarbon group and a polycyclic aliphatic hydrocarbon group) of Ra'$^3$ in formula (a1-r-1), and is further preferably a cyclohexylene group, a 1,5-adamantylene group, or a 2,6-adamantylene group.

Examples of Y$^{b1}$ include an ester bond (—C(=O)—O— or —O—C(=O)—), and a combination of an ester bond and an alkylene group.

In general formula (b1), V$^{b1}$ represents an alkylene group, a fluorinated alkylene group, or a single bond.

The number of carbon atoms of the alkylene group and the fluorinated alkylene group for V$^{b1}$ is preferably 1 to 4. Examples of the fluorinated alkylene group for V$^{b1}$ include a group in which at least one hydrogen atom of the alkylene group for V$^{b1}$ is substituted with a fluorine atom. Among them, V$^{b1}$ is preferably a single bond, or an alkylene group having 1 to 4 carbon atoms.

Specific examples of the anion part of the compound represented by general formula (b1) include an anion represented by general formula (an-0).

$$R^{b10}-(CH_2)_{v''}-\overset{O}{\underset{\|}{C}}-O-(CH_2)_{q''}-\left[O-\overset{O}{\underset{\|}{C}}\right]_{n''}-(CF_2)_{t''}-SO_3^-$$

(an-0)

In the formula, R$^{b10}$ represents a group obtained by removing one or more hydrogen atoms from polycycloalkane which may have a substituent. v" is an integer of 0 to 3. q" is an integer of 1 to 20. t" is an integer of 1 to 3. n" is 0 or 1.

In general formula (an-0), as the polycycloalkane for R$^{b10}$, polycycloalkane having a cross-linked polycyclic skeleton, or polycycloalkane having a condensed ring-based polycyclic skeleton such as a cyclic group having a steroid skeleton is preferable.

Examples of the substituents that the polycycloalkane for R$^{b10}$ include an alkyl group, an alkoxy group, a halogen atom, a halogenated alkyl group, a hydroxyl group, a carbonyl group, and a nitro group. The same groups as substituents that the cyclic hydrocarbon group for R$^{b1}$ in general formula (b1) may have.

Specifically, preferred examples of the anion represented by general formula (an-0) include anions represented by general formulae (an-1-1) to (an-1-3).

(an-1-1)

(an-1-2)

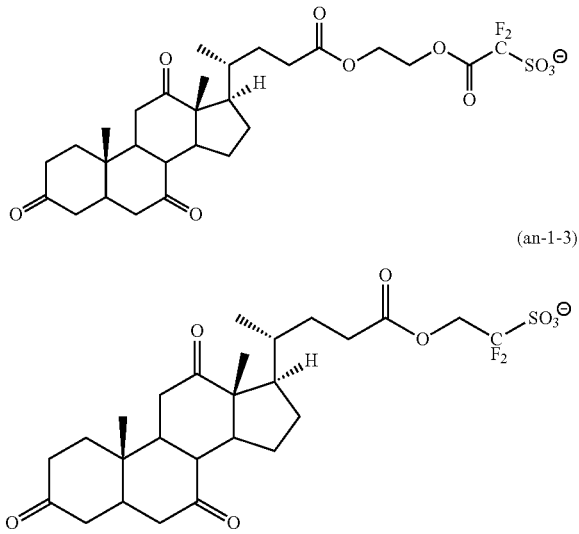

(an-1-3)

Cation Part $((M^{m+})_{1/m})$

In general formula (b1), $M^{m+}$ represents an m-valent organic cation. m is an integer of 1 or more.

As an organic cation of $M^{m+}$, a sulfonium cation and an iodonium cation are preferable.

Examples of preferred cation part $((M^{m+})_{1/m})$ include organic cations represented by general formulae (ca-1) to (ca-5).

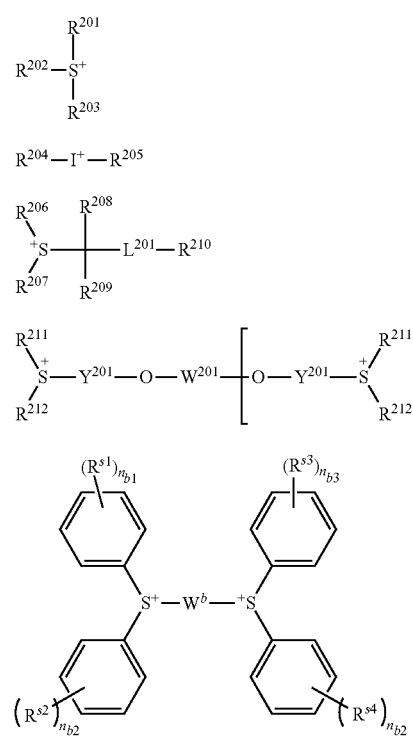

(ca-1)

(ca-2)

(ca-3)

(ca-4)

(ca-5)

In the formula, $R^{201}$ to $R^{207}$, and $R^{211}$ and $R^{212}$ each independently represent an aryl group which may have a substituent, an alkyl group, or an alkenyl group, and $R^{201}$ to $R^{203}$, $R^{206}$ and $R^{207}$, and $R^{211}$ and $R^{212}$ may be bonded to each other so as to form a ring together with a sulfur atom in the formula. $R^{208}$ and $R^{209}$ each independently represent a hydrogen atom or an alkyl group having 1 to 5 carbon atoms. $R^{210}$ represents an aryl group which may have a substituent, an alkyl group which may have a substituent, an alkenyl group which may have a substituent, or —$SO_2$—containing cyclic group may have a substituent. $L^{201}$ represents —C(=O)— or —C(=O)—O—. $Y^{201}$'s each independently represent an arylene group, an alkylene group, or an alkenylene group. x is 1 or 2. $W^{201}$ represents a (x+1) valent linking group. $W^b$ is a hydrocarbon group which may have a substituent. $R^{s1}$ to $R^{s4}$ are each independently a substituent. $n_{b1}$ to $n_{b4}$ are each independently an integer of 0 to 3.

Examples of the aryl group for $R^{201}$ to $R^{207}$ and $R^{211}$ and $R^{212}$ include an unsubstituted aryl group having 6 to 20 carbon atoms, and a phenyl group and a naphthyl group are preferable.

As the alkyl group for $R^{201}$ to $R^{207}$ and $R^{211}$ and $R^{212}$, a chain or cyclic alkyl group having 1 to 30 carbon atoms is preferable.

As the alkenyl group for $R^{201}$ to $R^{207}$ and $R^{211}$ and $R^{212}$, an alkenyl group having 2 to 10 carbon atoms is preferable.

Examples of the substituents that $R^{201}$ to $R^{207}$ and $R^{210}$ to $R^{212}$ which include an alkyl group, a halogen atom, a halogenated alkyl group, a carbonyl group, a cyano group, an amino group, an aryl group, and the groups which are represented by general formulae (ca-r-1) to (ca-r-7).

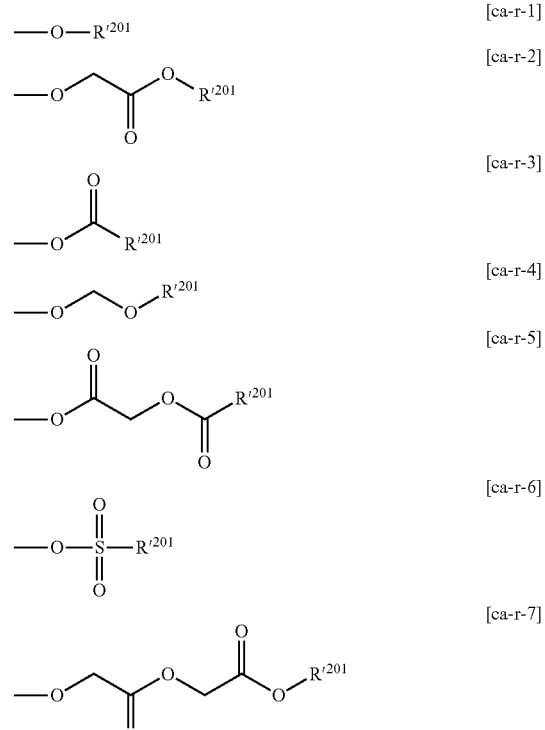

[ca-r-1]

[ca-r-2]

[ca-r-3]

[ca-r-4]

[ca-r-5]

[ca-r-6]

[ca-r-7]

In the formula, $R'^{201}$'s each independently represent a hydrogen atom, a cyclic group which may have a substituent, a chain alkyl group which may have a substituent, or a chain alkenyl group which may have a substituent.

Examples of the cyclic group which may have a substituent, the chain alkyl group which may have a substituent, or the chain alkenyl group which may have a substituent of $R'^{201}$ include the same groups of $R^{101}$ in general formula (b-1), and examples of the cyclic group which may have a substituent or the chain alkyl group which may have a substituent also include the same group as that of an acid dissociable group represented by formula (a1-r-2).

In the case where $R^{201}$ to $R^{203}$, $R^{206}$ and $R^{207}$, $R^{211}$ and $R^{212}$ are bonded to each other so as to form a ring together with a sulfur atom in the formula, the bonding may be performed via a heteroatom such as a sulfur atom, an oxygen atom, and a nitrogen atom, or a functional group such as a carbonyl group, —SO—, —SO$_2$—, —SO$_3$—, —COO—, —CONH— and —N($R_N$)— ($R_N$ is an alkyl group having 1 to 5 carbon atoms). As a ring to be formed, a ring including a sulfur atom in the formula in the ring skeleton is preferably 3- to 10-membered rings including a sulfur atom, and is particularly preferably 5- to 7-membered rings including a sulfur atom. Specific examples of rings to be formed include a thiophene ring, a thiazole ring, a benzothiophene ring, a thianthrene ring, a benzothiophene ring, a dibenzothiophene ring, a 9H-thioxanthene ring, athioxanthone ring, a thianthrene ring, a phenoxathiin ring, a tetrahydrothiophenium ring, and a tetrahydrothiopyranium ring.

$R^{208}$ and $R^{209}$ each independently represent a hydrogen atom or an alkyl group having 1 to 5 carbon atoms, and a hydrogen atom or an alkyl group having 1 to 3 carbon atoms is preferable, and in the case of the alkyl group, the alkyl groups may be bonded to each other so as to form a ring.

$R^{210}$ is an aryl group which may have a substituent, an alkyl group which may have a substituent, an alkenyl group which may have a substituent, or a —SO$_2$— containing cyclic group which may have a substituent.

Examples of the aryl group for $R^{210}$ include an unsubstituted aryl group having 6 to 20 carbon atoms, and a phenyl group and a naphthyl group are preferable.

The alkyl group for $R^{210}$ is a chain or cyclic alkyl group, and preferably has 1 to 30 carbon atoms.

The alkenyl group for $R^{210}$ preferably has 2 to 10 carbon atoms.

The —SO$_2$— containing cyclic group which may have a substituent for $R^{210}$ is preferably a "—SO$_2$— containing polycyclic group", and is further preferably a group represented by general formula (a5-r-1).

$Y^{201}$s each independently represent an arylene group, an alkylene group, and an alkenylene group.

Examples of the arylene group for $Y^{201}$ include a group obtained by removing one hydrogen atom from the aryl group exemplified as an aromatic hydrocarbon group for $R^{101}$ in general formula (b-1).

Examples of the alkylene group and the alkenylene group for $Y^{201}$ include a group obtained by removing one hydrogen atom a group exemplified as a chain alkyl group and a chain alkenyl group for $R^{101}$ in general formula (b-1).

In general formula (ca-4), x is 1 or 2.

$W^{201}$ is (x+1) valent, that is, a divalent or trivalent linking group.

The divalent linking group for $W^{201}$ is preferably a divalent hydrocarbon group which may have a substituent, and a divalent hydrocarbon group which may have a substituent, which is the same as that for $Ya^{21}$ in general formula (a2-1). The divalent linking group for $W^{201}$ may be linear, branched, or cyclic, and is preferably cyclic. Among them, a group in which two carbonyl groups are bonded at both ends of the arylene group is preferable. Examples of the arylene group include a phenylene group and a naphthylene group, and the phenylene group is particularly preferable.

Examples of the trivalent linking group for $W^{201}$ include a group obtained by removing one hydrogen atom from the divalent linking group for $W^{201}$ and a group to which the divalent linking group is further bonded to the divalent linking group. The trivalent linking group for $W^{201}$ is preferably a group in which two carbonyl groups are bonded to the arylene group.

In general formula (ca-5), $W^b$ is a hydrocarbon group which may have a substituent.

The hydrocarbon group for $W^b$ may be an aliphatic hydrocarbon group, or may be an aromatic hydrocarbon group.

Aliphatic Hydrocarbon Group

The aliphatic hydrocarbon group as a divalent hydrocarbon group for $W^b$ may be saturated or unsaturated, and is preferably saturated in general.

Examples of the aliphatic hydrocarbon group include a linear or branched aliphatic hydrocarbon group, or an aliphatic hydrocarbon group containing a ring in the structure.

Linear or Branched Aliphatic Hydrocarbon Group

The number of carbon atoms of the linear aliphatic hydrocarbon group is preferably 1 to 10, is further preferably 1 to 6, is further still preferably 1 to 4, and is most preferably 1 to 3.

As a linear aliphatic hydrocarbon group, a linear alkylene group is preferable, and specific examples include a methylene group [—CH$_2$—], an ethylene group [—(CH$_2$)$_2$—], a trimethylene group [—(CH$_2$)$_3$—], a tetramethylene group [—(CH$_2$)$_4$—], and a pentamethylene group [—(CH$_2$)$_5$—].

The number of carbon atoms of the branched aliphatic hydrocarbon group is preferably 3 to 10, is further preferably 3 to 6, is still further preferably 3 or 4, and is most preferably 3.

As a branched aliphatic hydrocarbon group, a branched alkylene group is preferable, and specific examples thereof include an alkyl alkylene group such as an alkyl methylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; an alkyl ethylene group such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, —C(CH$_2$CH$_3$)$_2$—CH$_2$—; an alkyl trimethylene group such as —CH(CH$_3$)CH$_2$CH$_2$— and —CH$_2$CH(CH$_3$)CH$_2$—; and an alkyl tetramethylene group such as —CH(CH$_3$)CH$_2$CH$_2$CH$_2$— and —CH$_2$CH(CH$_3$)CH$_2$CH$_2$—. As an alkyl group in an alkyl alkylene group, a linear alkyl group having 1 to 5 carbon atoms is preferable.

Aliphatic hydrocarbon group containing ring in structure

Examples of the aliphatic hydrocarbon group containing a ring in the structure include an alicyclic hydrocarbon group (a group obtained by removing two hydrogen atoms from an aliphatic hydrocarbon ring), a group in which the alicyclic hydrocarbon group is bonded to a terminal of the linear or branched aliphatic hydrocarbon group, and a group in which the alicyclic hydrocarbon group is present in the middle of the linear or branched aliphatic hydrocarbon group. Examples of the linear or branched aliphatic hydrocarbon group include the same groups as described above.

The number of carbon atoms of the alicyclic hydrocarbon group is preferably 3 to 20, and is further preferably 3 to 12.

The alicyclic hydrocarbon group may be a polycyclic group, or may be a monocyclic group. As the monoalicyclic hydrocarbon group, a group obtained by removing two hydrogen atoms from a monocycloalkane is preferable. The number of carbon atoms of the monocycloalkane is preferably 3 to 6. Specifically, examples thereof include cyclopentane and cyclohexane. As the polyalicyclic hydrocarbon group, a group obtained by removing two hydrogen atoms from polycycloalkane is preferable, and the number of carbon atoms of polycycloalkane is preferably 7 to 12. Specifically, examples thereof include adamantane, norbornane, isobornane, tricyclodecane, and tetracyclododecane.

Aromatic Hydrocarbon Group

An aromatic hydrocarbon group is a hydrocarbon group having an aromatic ring.

The number of carbon atoms of the aromatic hydrocarbon group as a divalent hydrocarbon group for the $W^b$ is preferably 3 to 30, is further preferably 5 to 30, is still further preferably 5 to 20, is particularly preferably 6 to 15, and is most preferably 6 to 10. Here, it is assumed that the number of carbon atoms does not include the number of carbon atoms in the substituent.

Specific examples of the aromatic ring having an aromatic hydrocarbon group include an aromatic hydrocarbon ring such as benzene, biphenyl, fluorene, naphthalene, anthracene, and phenanthrene; and aromatic heterocycle in which a portion of the carbon atoms which constitute the aromatic hydrocarbon ring is substituted with a heteroatom. Examples of the heteroatom in the aromatic heterocycle include an oxygen atom, a sulfur atom, and a nitrogen atom.

Specific examples of the aromatic hydrocarbon group include a group (an arylene group, and preferably a phenylene group and a naphthylene group) obtained by removing two hydrogen atoms from the above-mentioned aromatic hydrocarbon ring; and a group in which one hydrogen atom of a group (an aryl group) obtained by removing one hydrogen atom from the above-mentioned aromatic hydrocarbon ring is substituted with an alkylene group (for example, a group which one hydrogen atom is removed from an aryl group in an aryl alkyl group such as a benzyl group, a phenethyl group, a 1-naphthyl methyl group, a2-naphthyl methyl group, a 1-naphthyl ethyl group, and a 2-naphthyl ethyl group). The number of carbon atoms of the alkylene group (an alkyl chain in the aryl alkyl group) is preferably 1 to 4, is further preferably 1 or 2, and is particularly preferably 1.

Examples of the substituents that a hydrocarbon group of $W^b$ include an alkyl group having 1 to 5 carbon atoms, an alkoxy group having 1 to 5 carbon atoms, an oxy group (=O), a hydroxyl group (—OH), and an amino group (—NH₂).

Among them, as $W^b$, an aromatic hydrocarbon group is preferable, and as an aromatic ring that the aromatic hydrocarbon group has, benzene, biphenyl, or naphthalene is preferable, and benzene and biphenyl are further preferable.

In general formula (ca-5), $R^{s1}$ to $R^{s4}$ are each independently a substituent.

Examples of the substituents for $R^{s1}$ to $R^{s4}$ include an alkyl group, a halogen atom, a halogenated alkyl group, a carbonyl group, a cyano group, an amino group, an aryl group, an arylthio group, and the groups represented by general formula (ca-r-1) to (ca-r-7).

Examples of the arylthio group as a substituent include a phenylthio group and a biphenylthio group.

In general formula (ca-5), $n_{b1}$ to $n_{b4}$ are each independently an integer of 0 to 3, are preferably 0 or 1, and are further preferably 0.

Specific examples of preferred cation represented by formula (ca-1) include cations represented by the following formulae (ca-1-1) to (ca-1-74).

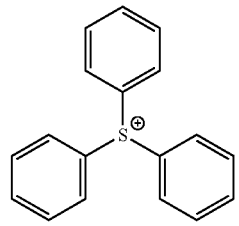

(ca-1-1)

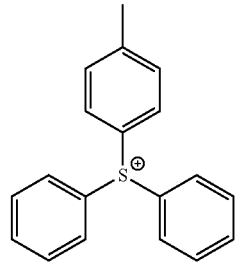

(ca-1-2)

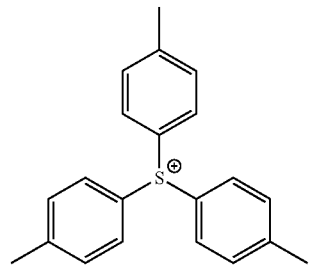

(ca-1-3)

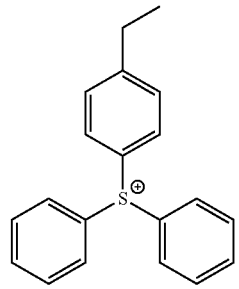

(ca-1-4)

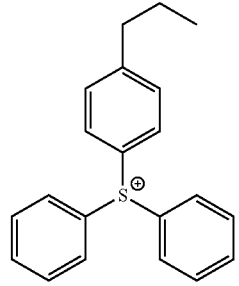

(ca-1-5)

(ca-1-6)
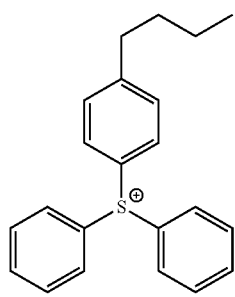
(ca-1-11)
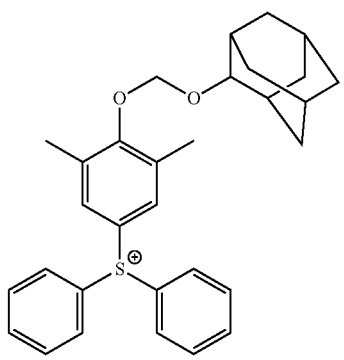
(ca-1-7)
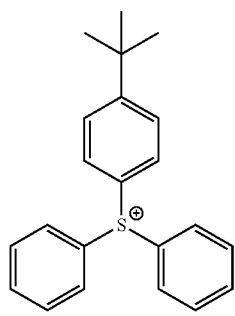
(ca-1-12)
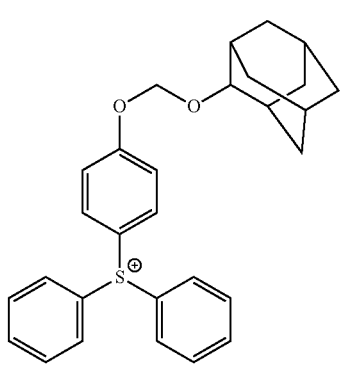
(ca-1-8)
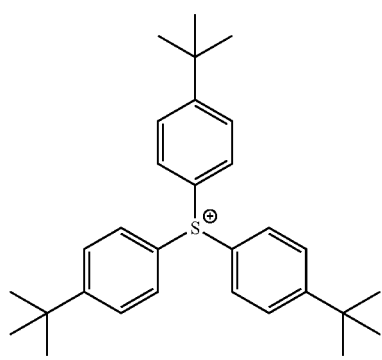
(ca-1-13)
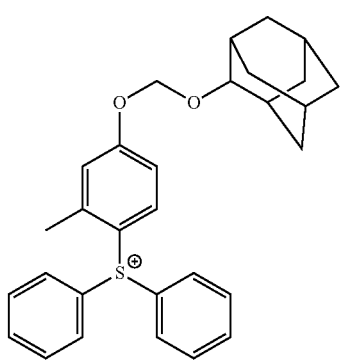
(ca-1-9)
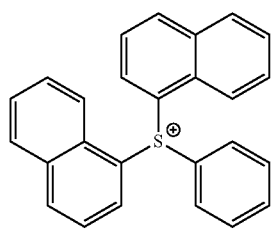
(ca-1-10)
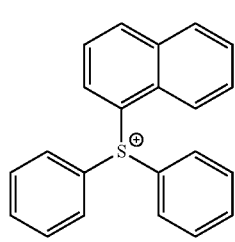
(ca-1-14)
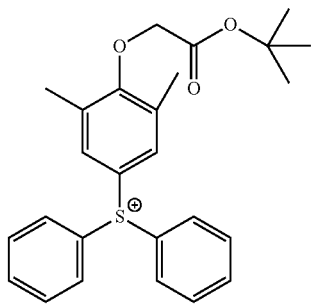

(ca-1-15)
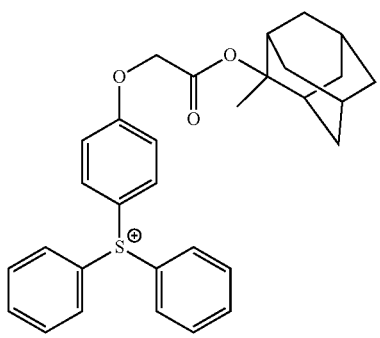
(ca-1-16)
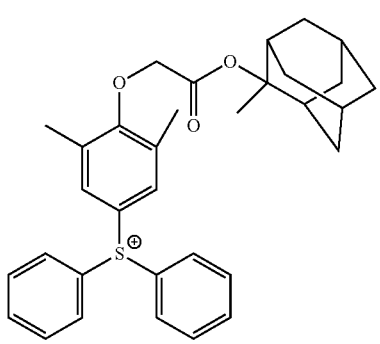
(ca-1-17)
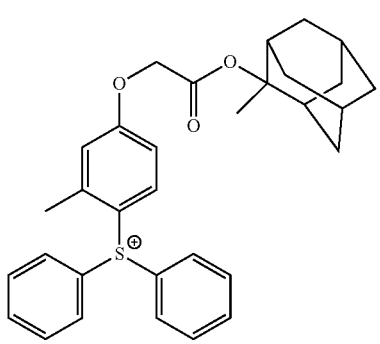
(ca-1-18)
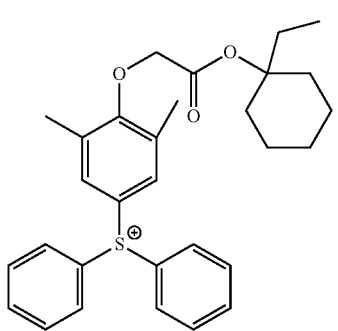
(ca-1-19)
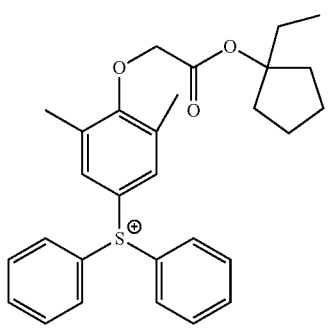
(ca-1-20)
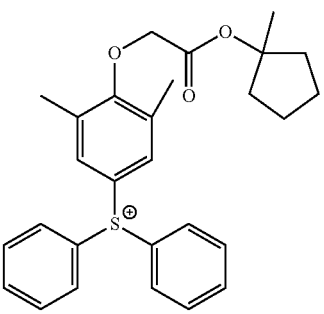
(ca-1-21)
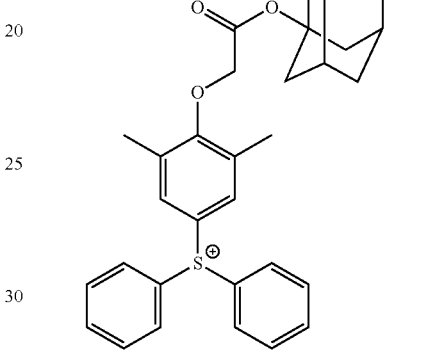
(ca-1-22)
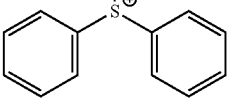
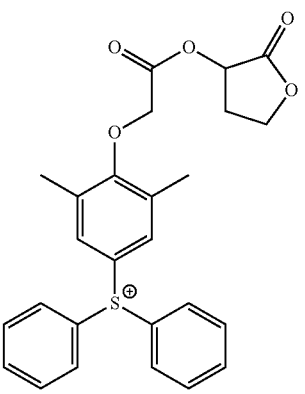
(ca-1-23)
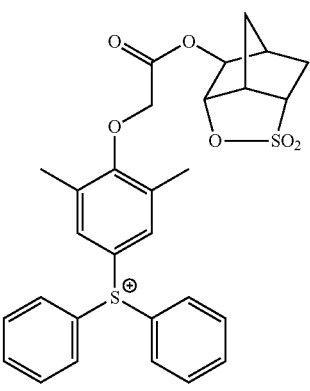

(ca-1-24)
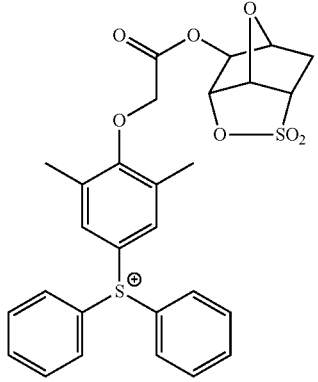
(ca-1-25)
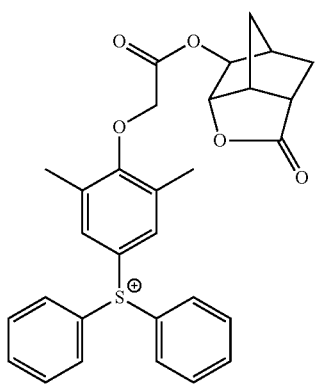
(ca-1-26)
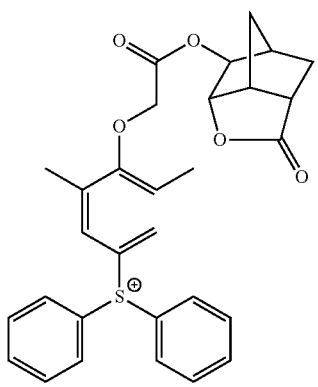
(ca-1-27)
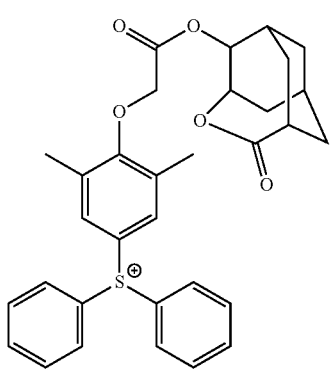
(ca-1-28)
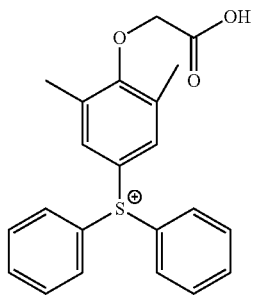
(ca-1-29)
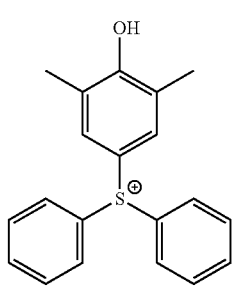
(ca-1-30)
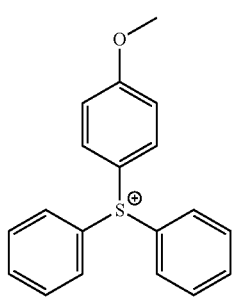
(ca-1-31)
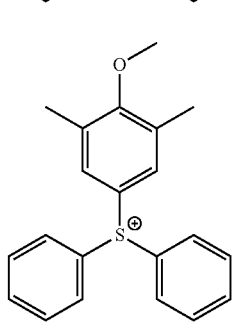
(ca-1-32)
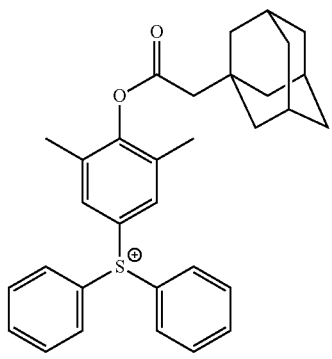

(ca-1-33) 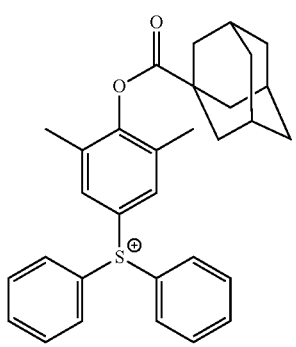
(ca-1-34) 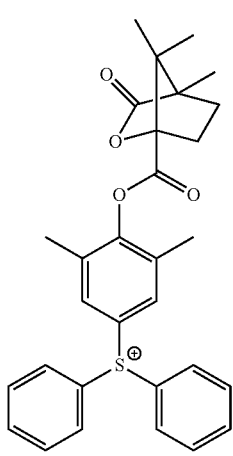
(ca-1-35) 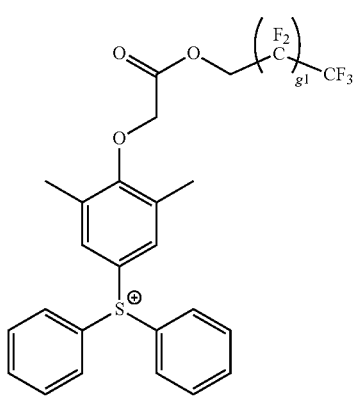
(ca-1-36) 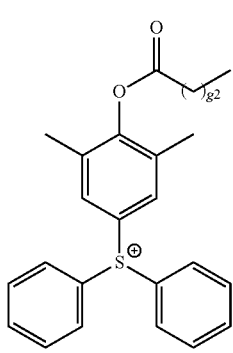
(ca-1-37) 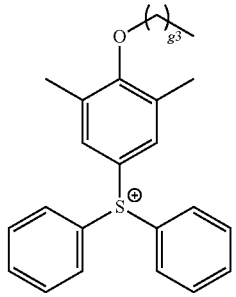
(ca-1-38) 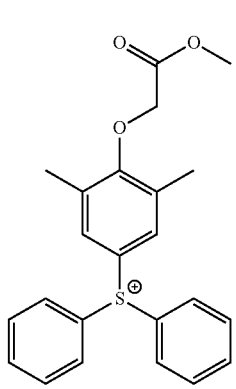
(ca-1-39) 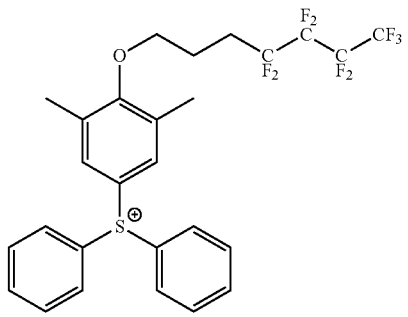
(ca-1-40) 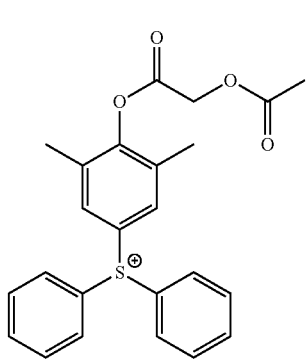

-continued
(ca-1-41)
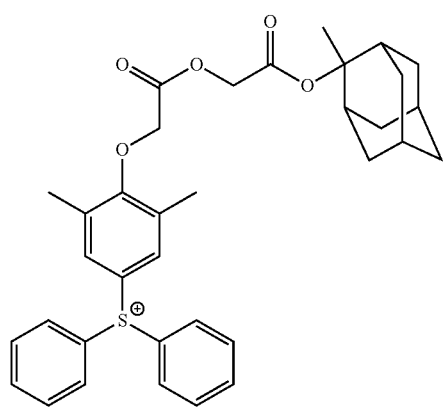
(ca-1-42)
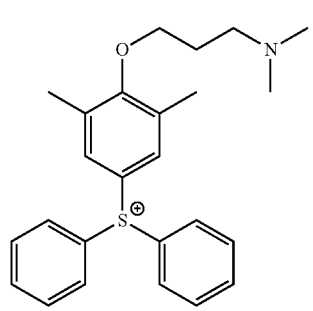
(ca-1-43)
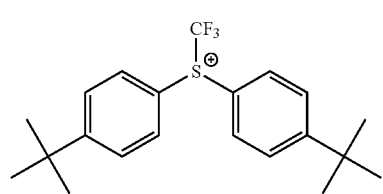
(ca-1-44)
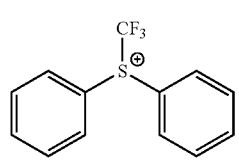
(ca-1-45)
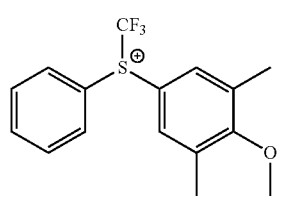
(ca-1-46)
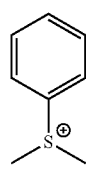
(ca-1-47)
-continued
(ca-1-48)
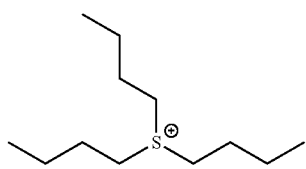
(ca-1-49)
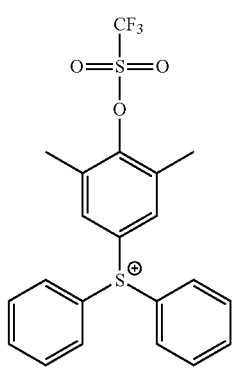
(ca-1-50)
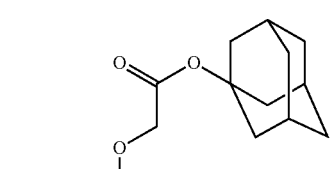
(ca-1-51)
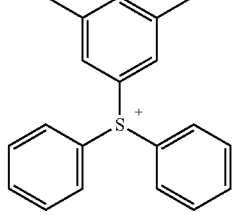
In the formula, g1, g2, and g3 represent repeated numbers; g1 is an integer of 1 to 5, g2 is an integer of 0 to 20, and g3 is an integer of 0 to 20.
(ca-1-52)
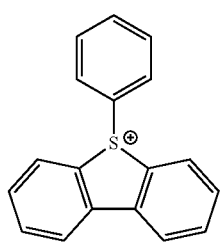

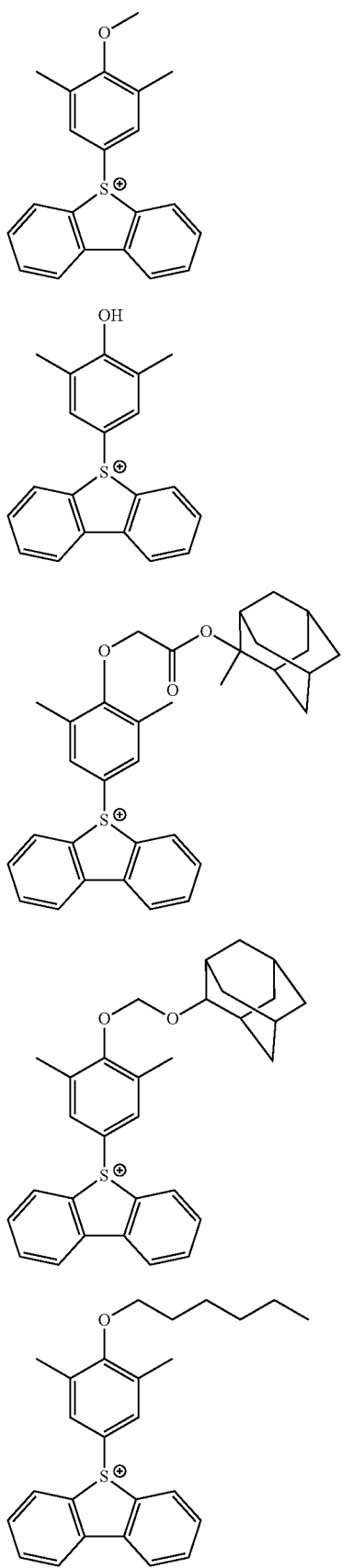
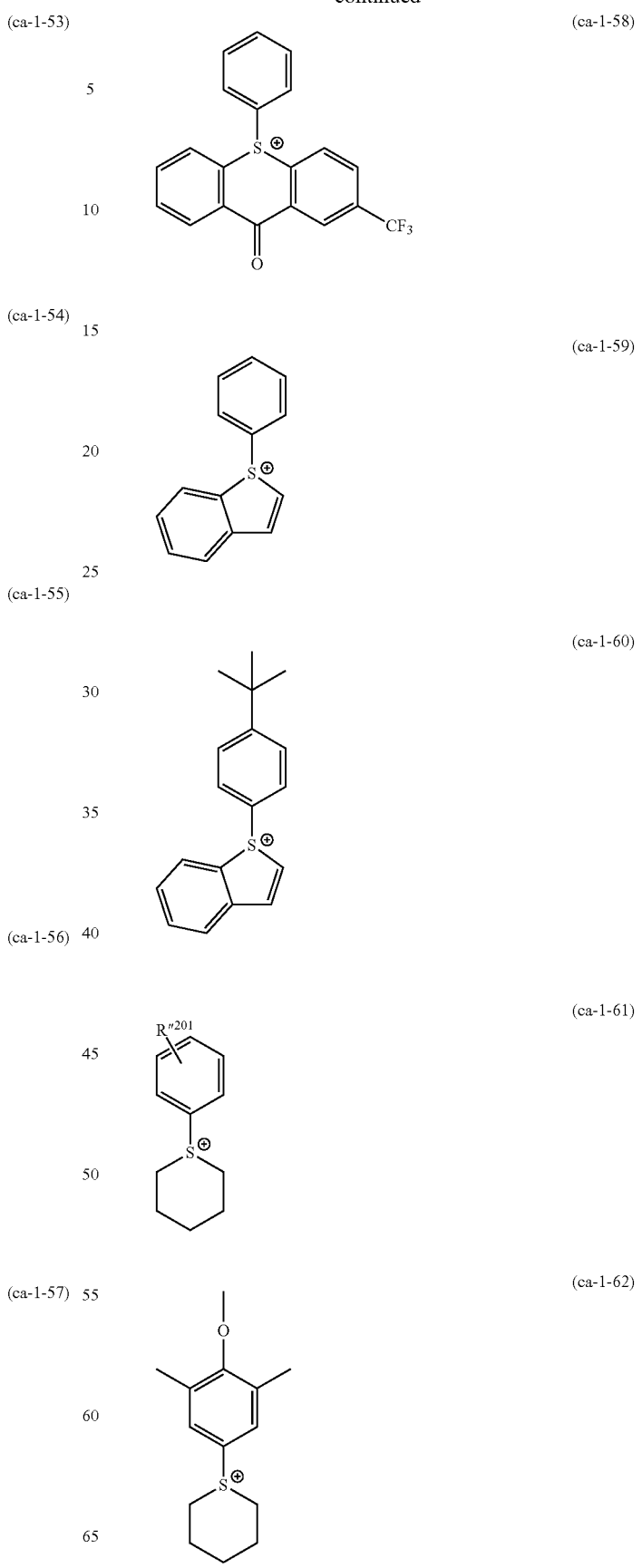

(ca-1-63)
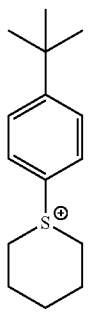
(ca-1-64)
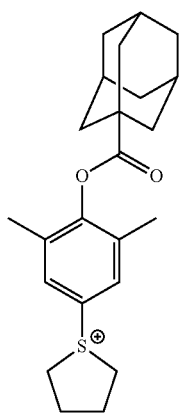
(ca-1-65)
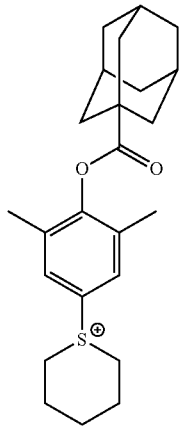
(ca-1-66)
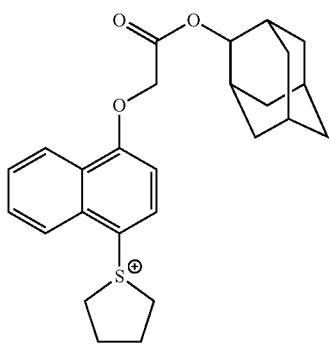
(ca-1-67)
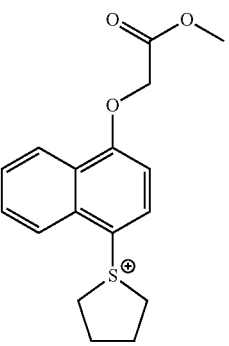
(ca-1-68)
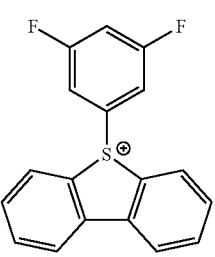
(ca-1-69)
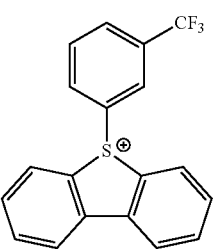
(ca-1-70)
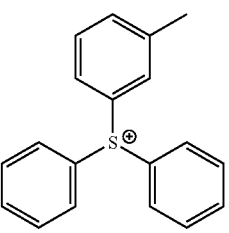
(ca-1-71)
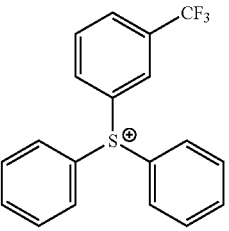

(ca-1-72)

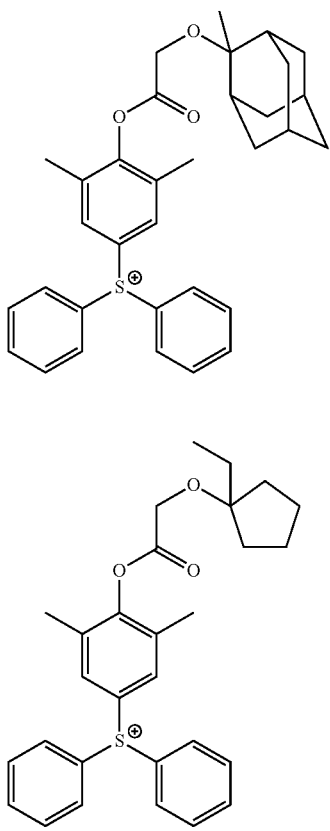

(ca-3-2)

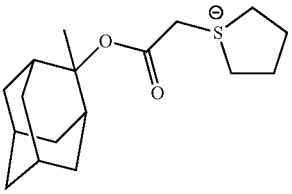

(ca-3-3)

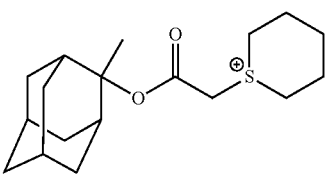

(ca-1-73)

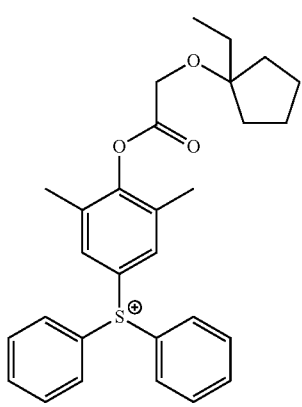

(ca-3-4)

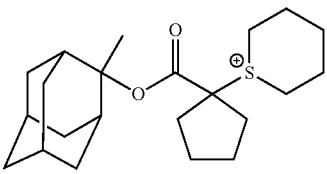

(ca-3-5)

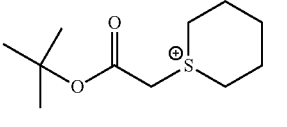

(ca-1-74)

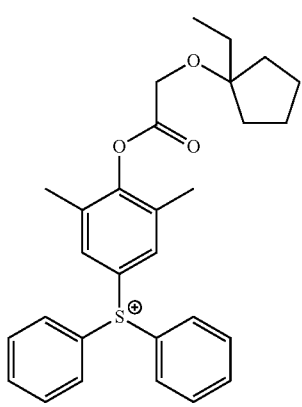

(ca-3-6)

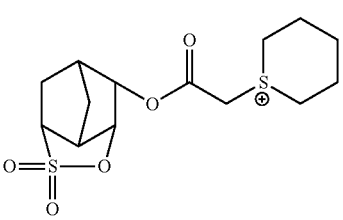

In the formula, $R''^{201}$ is a hydrogen atom or a substituent, and the substituent is the same as a substituent that which may have $R^{201}$ to $R^{207}$ and $R^{210}$ to $R^{212}$.

Specifically, examples of the preferred cation represented by general formula (ca-2) include diphenyl iodonium cation and bis(4-tert-butylphenyl) iodonium cation.

Specifically, examples of the preferred cation represented by general formula (ca-3) include cations represented by general formulae (ca-3-1) to (ca-3-6).

Specifically, examples of the preferred cation represented by general formula (ca-4) include cations represented by general formulae (ca-4-1) and (ca-4-2).

(ca-4-1)

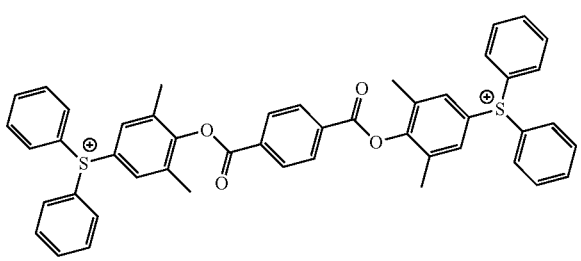

(ca-3-1)

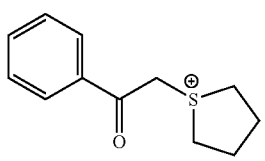

(ca-4-2)

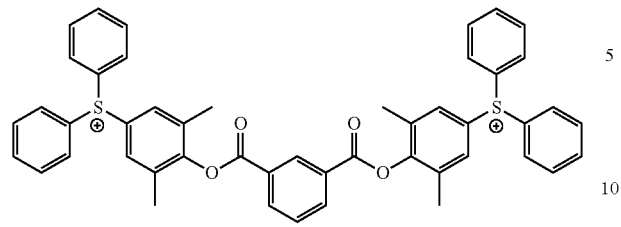

Specifically, examples of the preferred cation represented by general formula (ca-5) include cations represented by general formulae (ca-5-1) and (ca-5-2).

(ca-5-2)

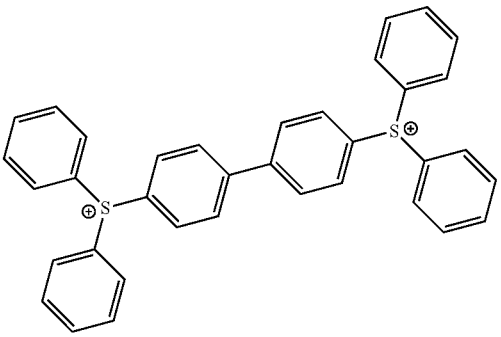

(ca-5-1)

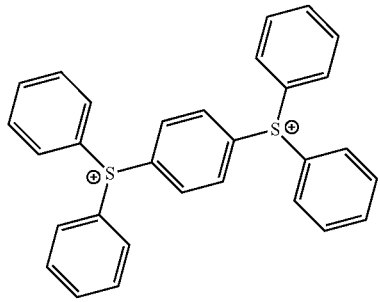

Among them, the cation part $((M^{m+})_{1/m})$ is the cation represented by general formula (ca-1), is preferably the cation represented by general formula (ca-5), and is further preferably the cations respectively represented by general formulae (ca-1-1) to (ca-1-74) or the cations respectively represented by (ca-5-1) and (ca-5-2).

Specific examples of the preferred (B1) component will be described below.

(B1)-1

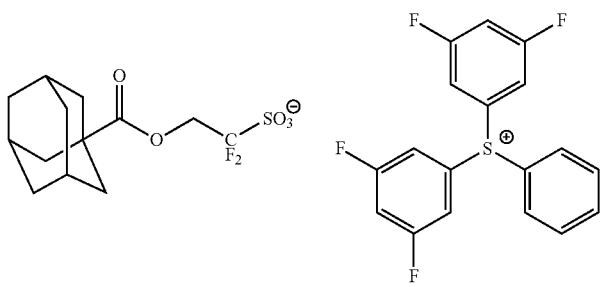

(B1)-2

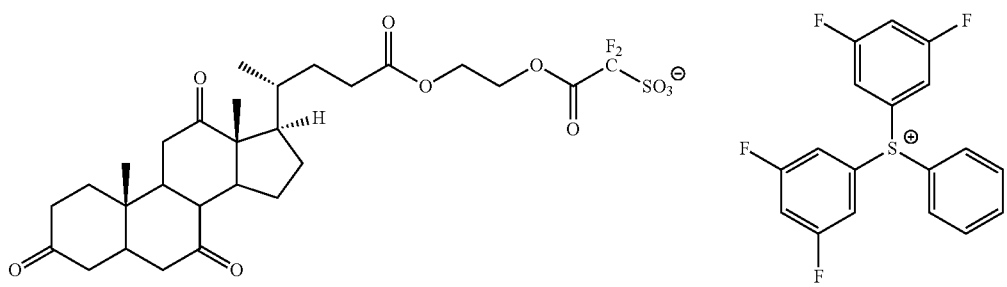

-continued

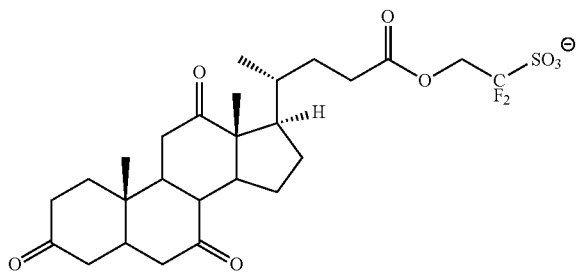
(B1)-4

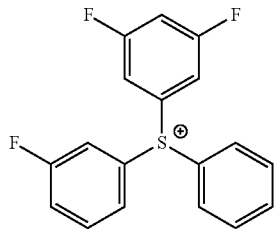
(B1)-3

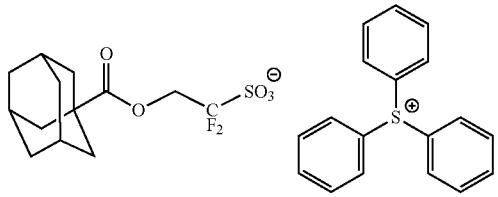
(B1)-5

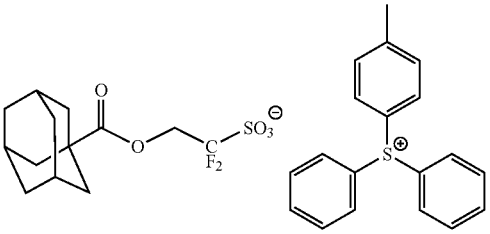
(B1)-6

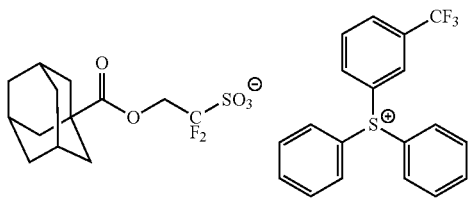
(B1)-7

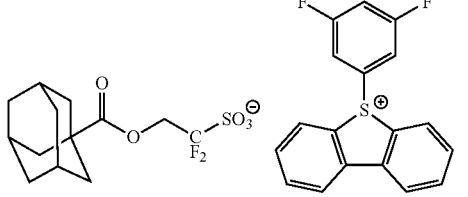
(B1)-8

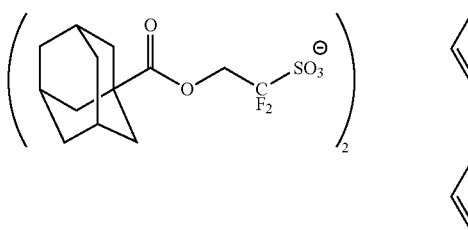
(B1)-9

(B1)-10

(B1)-11

In the resist composition of the present embodiment, the (B1) component may be used alone, or two or more kinds thereof may be used in combination.

In the resist composition of the present embodiment, the content of the (B1) component is preferably 1 to 40 parts by mass, is further preferably 5 to 35 parts by mass, and is still further preferably 9 to 30 parts by mass, with respect to 100 parts by mass of the (A) component.

When the content of the (B1) component is equal to or greater than the preferred lower limit value, in the forming of the resist pattern, the lithography properties such as the sensitivity, the resolution, the reduced line wise roughness (LWR), and the shape are improved. On the other hand, when the content of the (B1) component is equal to or lower than the preferred upper limit value, when the respective components of the resist composition are dissolved in an organic solvent, it is easy to obtain a uniform solution, and the storage stability of the component as a resist composition is improved.

(B2) Component

The resist composition of the present embodiment may contain an acid generator component (hereinafter, referred to as "(B2) component") other than the (B1) component to the extent that the effect of the present invention is not impaired.

The (B2) component is not particularly limited, and examples thereof include components which have been suggested as acid generators for chemically amplified resist compositions.

Examples of such an acid generator include various kinds of acid generators such as an onium salt-based acid generator such as an iodonium salt and a sulfonium salt, an oxime sulfonate-based acid generator; bisalkyl or bisaryl sulfonyl diazomethane, a diazomethane-based acid generator such as poly (bissulfonyl) diazomethane; a nitrobenzylsulfonate-based acid generator, an iminosulfonate-based acid generator, and a disulfone-based acid generator.

Examples of the onium salt-based acid generator include a compound (hereinafter, also referred to as "(b-1) component") represented by general formula (b-1), a compound (hereinafter, also referred to as "(b-2) component") represented by general formula (b-2), or a compound (hereinafter, also referred to as "(b-3) component") represented by general formula (b-3). Note that, it is assumed that the (b-1) component does not include a compound corresponding to the (B1) component.

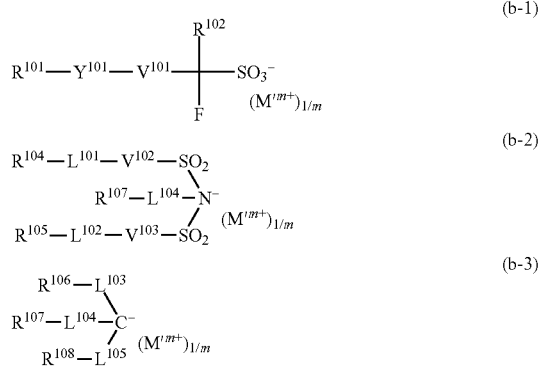

In the formula, $R^{101}$, $R^{104}$ to $R^{108}$ each independently represent a cyclic group which may have a substituent, a chain alkyl group which may have a substituent, or a chain alkenyl group which may have a substituent. $R^{104}$ and $R^{105}$ may be bonded to each other so as to form a ring.

$R^{102}$ is a fluorine atom or a fluorinated alkyl group having 1 to 5 carbon atoms. $Y^{101}$ is a divalent linking group containing a single bond or an oxygen atom. $V^{101}$ to $V^{103}$ each independently represent a single bond, an alkylene group, or a fluorinated alkylene group. $L^{101}$ and $L^{102}$ each independently represent a single bond or an oxygen atom. $L^{103}$ to $L^{105}$ each independently represent a single bond, —CO— or —SO$_2$—. m is an integer of 1 or more, and $M^{m+}$ is an m-valent onium cation.

Anion Part

Anion Part of (b-1) Component

In general formula (b-1), $R^{101}$ is a cyclic group which may have a substituent, a chain alkyl group which may have a substituent, or a chain alkenyl group which may have a substituent.

Cyclic Group which May have a Substituent:

The cyclic group is preferably a cyclic hydrocarbon group, and the cyclic hydrocarbon group may be an aromatic hydrocarbon group, or may be an aliphatic hydrocarbon group. The aliphatic hydrocarbon group means a hydrocarbon group having no aromaticity. In addition, the aliphatic hydrocarbon group may be saturated or unsaturated, and is usually preferably saturated.

The aromatic hydrocarbon group for $R^{101}$ is a hydrocarbon group having an aromatic ring. The number of carbon atoms of the aromatic hydrocarbon group is preferably 3 to 30, is further preferably 5 to 30, is still further preferably 5 to 20, is particularly preferably 6 to 15, and is most preferably 6 to 10. Here, it is assumed that the number of carbon atoms does not include the number of carbon atoms in the substituent.

Specific examples of an aromatic ring having an aromatic hydrocarbon group for $R^{101}$ include benzene, fluorene, naphthalene, anthracene, phenanthrene, biphenyl, or an aromatic heterocycle in which a portion of carbon atoms constituting these aromatic rings is substituted with heteroatoms. Examples of the heteroatom in the aromatic heterocycle include an oxygen atom, a sulfur atom, and a nitrogen atom.

Specific examples of the aromatic hydrocarbon group for $R^{101}$ include a group obtained by removing one hydrogen atom from the aromatic ring (aryl group: for example, a phenyl group and a naphthyl group), a group in which one hydrogen atom of the aromatic ring is substituted with an alkylene group (for example, an aryl alkyl group such as a benzyl group, a phenethyl group, a 1-naphtyl methyl group, a 2-naphtyl methyl group, a 1-naphtyl ethyl group, and a 2-naphtyl ethyl group). The number of carbon atoms of the alkylene group (an alkyl chain in an aryl alkyl group) is preferably 1 to 4, is more preferably 1 to 2, and is particularly preferably 1.

Among them, as an aromatic hydrocarbon group for $R^{101}$, a phenyl group or a naphthyl group is further preferable.

Examples of the cyclic aliphatic hydrocarbon group for $R^{101}$ include an aliphatic hydrocarbon group including a ring in a structure.

Examples of the aliphatic hydrocarbon group including a ring in this structure include an alicyclic hydrocarbon group (a group obtained by removing one hydrogen atom from an aliphatic hydrocarbon ring), a group in which an alicyclic hydrocarbon group is bonded to a terminal of a linear or branched aliphatic hydrocarbon group, and a group in which an alicyclic hydrocarbon group is present in the middle of the linear or branched aliphatic hydrocarbon group.

The number of carbon atoms of the alicyclic hydrocarbon group is preferably 3 to 20, and is further preferably 3 to 12.

The alicyclic hydrocarbon group may be a polycyclic group, or may be a monocyclic group. As the monocyclic alicyclic hydrocarbon group, a group obtained by removing one or more hydrogen atoms from the monocycloalkane is preferable. As the monocycloalkane, a group having 3 to 6 carbon atoms is preferable, and specific examples thereof include cyclopentane and cyclohexane. As the polycyclic alicyclic hydrocarbon group, a group obtained by removing one or more hydrogen atoms from the polycycloalkane is preferable, and as the polycycloalkane, a group having 7 to 30 carbon atoms is preferable. Among them, as polycycloalkane, polycycloalkane having a bridged ring polycyclic skeleton such as adamantane, norbornane, isobornane, tricyclodecane, and tetracyclododecene; and polycycloalkane having a condensed ring-based polycyclic skeleton such as a cyclic group having a steroid skeleton is further preferable.

Among them, as the cyclic aliphatic hydrocarbon group for $R^{101}$, a group obtained by removing one or more hydrogen atom from monocycloalkane or polycycloalkane is preferable, a group obtained by excluding one hydrogen atom from polycycloalkane is further preferable, an adamantyl group and a norbornyl group are particularly preferable, and an adamantyl group is most preferable.

The number of carbon atoms of a linear or branched aliphatic hydrocarbon group that may be bonded to an alicyclic hydrocarbon group is preferably 1 to 10, is further preferably 1 to 6, is further still preferably 1 to 4, and is most preferably 1 to 3.

As a linear aliphatic hydrocarbon group, a linear alkylene group is preferable, and specific examples include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

As a branched aliphatic hydrocarbon group, a branched alkylene group is preferable, and specific examples thereof include an alkyl alkylene group such as an alkyl methylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; an alkyl ethylene group such as —$CH(CH_3)CH_2$—, —$CH(CH_3)CH(CH_3)$—, —$C(CH_3)_2CH_2$—, —$CH(CH_2CH_3)CH_2$—, —$C(CH_2CH_3)_2$—$CH_2$—; an alkyltrimethylene group such as —$CH(CH_3)CH_2CH_2$— and —$CH_2CH(CH_3)CH_2$—; and an alkyltetramethylene group such as —$CH(CH_3)CH_2CH_2CH_2$— and —$CH_2CH(CH_3)CH_2CH_2$—. As an alkyl group in an alkyl alkylene group, a linear alkyl group having 1 to 5 carbon atoms is preferable.

In addition, a cyclic hydrocarbon group for $R^{101}$ may include a heteroatom such as a heterocycle. Specific examples include lactone-containing cyclic groups respectively represented by general formulae (a2-r-1), (a2-r-3) to (a2-r-7), —$SO_2$— containing cyclic groups respectively represented by general formulae (a5-r-1) to (a5-r-4), and other heterocyclic groups respectively represented by chemical formulae (r-hr-1) to (r-hr-16) described above.

Examples of the substituent in a cyclic group of $R^{101}$ include an alkyl group, an alkoxy group, a halogen atom, a halogenated alkyl group, a hydroxyl group, and a carbonyl group.

The alkyl group as a substituent is preferably an alkyl group having 1 to 5 carbon atoms, and is most preferably a methyl group, an ethyl group, a propyl group, an n-butyl group, and a tert-butyl group.

The alkoxy group as a substituent is preferably an alkoxy group having 1 to 5 carbon atoms, is further preferably a methoxy group, an ethoxy group, an n-propoxy group, an iso-propoxy group, an n-butoxy group, and a tert-butoxy group, and is most preferably a methoxy group and an ethoxy group.

Examples of the halogen atom as a substituent include a fluorine atom, a chlorine atom, a bromine atom, and an iodine atom, and among them, the fluorine atom is preferable.

Examples of the halogenated alkyl group as a substituent include a group in which at least one hydrogen atom of an alkyl group having 1 to 5 carbon atoms, such as a methyl group, an ethyl group, a propyl group, an n-butyl group, and a tert-butyl group, is substituted with a halogen atom.

A carbonyl group as a substituent is a group in which a methylene group (—$CH_2$—) constituting a cyclic hydrocarbon group is substituted.

Chain Alkyl Group which May have Substituent:

A chain alkyl group of $R^{101}$ may be a linear alkyl group or a branched alkyl group.

The number of carbon atoms of the linear alkyl group is preferably 1 to 20, is further preferably 1 to 15, is particularly preferably 1 to 11, and is most preferably 1 to 5. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a heneicosyl group, and a docosyl group.

The number of carbon atoms of the branched alkyl group is preferably 3 to 20, is further preferably 3 to 15, and is most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a2-ethylbutyl group, a 1-methylpentyl group, a 2-methylpentyl group, a 3-methylpentyl group, and a 4-methylpentyl group.

Among them, the number of carbon atoms of a chain alkyl group in $R^{101}$ is preferably 1 to 10, and specific examples include a linear alkyl group such as a methyl group, an ethyl group, a propyl group, a butyl group, a pentyl group, a hexyl group, a heptyl group, an octyl group, a nonyl group, and a decyl group; and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group are preferable.

Chain Alkenyl Group which May have Substituent:

A chain alkenyl group of $R^{101}$ may be a linear alkenyl group or a branched alkenyl group, and the number of carbon atoms of the chain-shaped alkenyl group of $R^{101}$ is preferably 2 to 10, is further preferably 2 to 5, and is further preferably 2 to 4, and is particularly preferably 3. Examples of the linear alkenyl group include a vinyl group, a propenyl group (allyl group), and a butynyl group. Examples of the branched alkenyl group include 1-methylvinyl group, 2-methylvinyl group, 1-methyl propenyl group, and 2-methyl propenyl group.

Among them, as a chain alkenyl group for $R^{101}$, a linear alkenyl group is preferable, a vinyl group and a propenyl group are further preferable, and a vinyl group is particularly preferable.

Examples of a substituent in a chain alkyl group or a chain alkenyl group of $R^{101}$ include an alkoxy group, a halogen atom, a halogenated alkyl group, a hydroxy group, a carbonyl group, an amino group, and a cyclic group in $R^{101}$ above.

Among them, $R^{101}$ is preferably the cyclic group which may have a substituent, and is further preferably the cyclic hydrocarbon group which may have a substituent. More specific examples thereof include a group obtained by removing one or more hydrogen atoms from a phenyl group, a naphthyl group, and polycycloalkane; lactone-containing cyclic groups respectively represented by general formulae (a2-r-1), and (a2-r-3) to (a2-r-7); and —$SO_2$— containing cyclic groups respectively represented by general formulae (a5-r-1) to (a5-r-4).

In general formula (b-1), $Y^{101}$ is a divalent linking group containing a single bond or an oxygen atom.

In the case where $Y^{101}$ is a divalent linking group containing an oxygen atom, $Y^{101}$ may contain atoms other than the oxygen atom. Examples of the atoms other than the oxygen atom include a carbon atom, a hydrogen atom, a sulfur atom, and a nitrogen atom.

Examples of the divalent linking group containing an oxygen atom include a non-hydrocarbon-based oxygen atom-containing linking group such as an oxygen atom (ether bond: —O—), an ester bond (—C(=O)—O—), an oxycarbonyl group (—O—C(=O)—), an amide bond (—C(=O)—NH—), a carbonyl group (—C(=O)—), and a carbonate bond (—O—C(=O)—O—); and a combination of the a non-hydrocarbon-based oxygen atom-containing linking group with an alkylene group. A sulfonyl group (—$SO_2$—) may be further linked to the aforementioned combination. Examples of the divalent linking group containing an oxygen atom include linking groups respectively represented by general formulae (y-al-1) to (y-al-7).

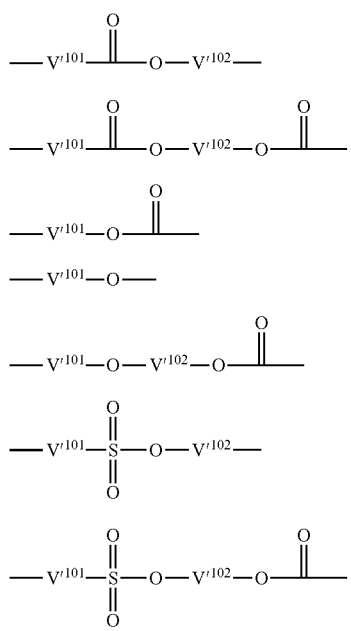

In the formula, $V'^{101}$ is a single bond or an alkylene group having 1 to 5 carbon atoms, and $V'^{102}$ is divalent saturated hydrocarbon group having 1 to 30 carbon atoms.

The divalent saturated hydrocarbon group for $V'^{102}$ is preferably an alkylene group having 1 to 30 carbon atoms, is further preferably an alkylene group having 1 to 10 carbon atoms, and is still further preferably an alkylene group having 1 to 5 carbon atoms.

The alkylene group for $V'^{101}$ and $V'^{102}$ may be a linear alkylene group or a branched alkylene group, and is preferably a linear alkylene group.

Specific examples of the alkylene group for $V'^{101}$ and $V'^{102}$ include a methylene group [—$CH_2$—]; an alkyl methylene group such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; an ethylene group [—$CH_2CH_2$—]; an alkyl ethylene group such as —CH($CH_3$)$CH_2$—, —CH($CH_3$)CH($CH_3$)—, —C($CH_3$)$_2CH_2$—, and —CH($CH_2CH_3$)$CH_2$—; a trimethylene group (an n-propylene group) [—$CH_2CH_2CH_2$—]; alkyl trimethylene group such as —CH($CH_3$)$CH_2CH_2$—, and —$CH_2$CH($CH_3$)$CH_2$—; a tetramethylene group [—$CH_2CH_2CH_2CH_2$—]; an alkyl tetramethylene group such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

Further, a portion of methylene groups in the alkylene group for $V'^{101}$ or $V'^{102}$ may be substituted with a divalent aliphatic cyclic group having 5 to 10 carbon atoms. The aliphatic cyclic group is preferably a divalent group obtained by further removing one hydrogen atom from a cyclic aliphatic hydrocarbon group (a monocyclic aliphatic hydrocarbon group and a polycyclic aliphatic hydrocarbon group) of $Ra'^3$ in general formula (a1-r-1), and is further preferably a cyclohexylene group, a 1,5-adamantylene group, or a 2,6-adamantylene group.

As $Y^{101}$, a divalent linking group containing an ester bond, or a divalent linking group containing an ether bond is preferable, and linking groups respectively represented by general formulae (y-al-1) to (y-al-5) are further preferable.

In general formula (b-1), $V^{101}$ is a single bond, an alkylene group, or a fluorinated alkylene group. The alkylene group and the fluorinated alkylene group for $V^{101}$ preferably have 1 to 4 carbon atoms. Examples of the fluorinated alkylene group for $V^{101}$ include a group in which at least one hydrogen atom of the alkylene group for $V^{101}$ is substituted with a fluorine atom. Among them, $V^{101}$ is preferably a single bond or a fluorinated alkylene group having 1 to 4 carbon atoms.

In general formula (b-1), $R^{102}$ is a fluorine atom or a fluorinated alkyl group having 1 to 5 carbon atoms. $R^{102}$ is preferably a fluorine atom or a perfluoroalkyl group having 1 to 5 carbon atoms, and is further preferably a fluorine atom.

Specific examples of the anion part of the (b-1) component include a fluorinated alkyl sulfonate anion such as trifluoromethanesulfonate anion and perfluorobutanesulfonate anion in the case where $Y^{101}$ is a single bond; and the anion represented by any one of general formulae (an-1) to (an-3) in the case where $Y^{101}$ is a divalent linking group containing an oxygen atom.

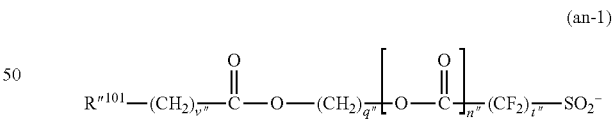

In the formula, $R''^{101}$ is an aliphatic cyclic group which may have a substituent, groups respectively represented by formulae (r-hr-1) to (r-hr-6), or a chain alkyl group which may have a substituent; $R''^{102}$ is an aliphatic cyclic group which may have a substituent, a lactone-containing cyclic group represented by general formulae (a2-r-1), (a2-r-3) to (a2-r-7), or a —SO$_2$— containing cyclic group represented by general formulae (a5-r-1) to (a5-r-4); R'''$^{103}$ is an aromatic cyclic group which may have a substituent, an aliphatic cyclic group which may have a substituent, or a chain alkenyl group which may have a substituent; v'''s are each independently an integer of 0 to 3, q'''s are each independently an integer of 1 to 20, t'' are each independently an integer of 1 to 3, and n'' is an integer of 0 or 1.

The aliphatic cyclic group which may have a substituent for R'''$^{101}$, R'''$^{102}$, and R'''$^{103}$ is preferably a group exemplified as a cyclic aliphatic hydrocarbon group of R$^{101}$ in general formula (b-1). Examples of the substituents include the same substituents as those with which the cyclic aliphatic hydrocarbon group of R$^{101}$ in general formula (b-1) may be substituted.

The aromatic cyclic group which may have a substituent for R'''$^{103}$ is preferably a group exemplified as an aromatic hydrocarbon group of a cyclic hydrocarbon group of R$^{101}$ in general formula (b-1). Examples of the substituents include the same substituents as those with which an aromatic hydrocarbon group of R$^{101}$ in general formula (b-1) may be substituted.

The chain alkyl group which may have a substituent for R'''$^{101}$ is preferably a group exemplified as a chain alkyl group of R$^{101}$ in general formula (b-1). The chain alkenyl group which may have a substituent for R'''$^{103}$ is preferably a group exemplified as a chain alkenyl group of R$^{101}$ in general formula (b-1).

Anion Part of (b-2) Component

In the formula (b-2), R$^{104}$ and R$^{105}$ each independently represent a cyclic group which may have a substituent, a chain alkyl group which may have a substituent, or a chain alkenyl group which may have a substituent, which is the same as a cyclic group which may have a substituent, a chain alkyl group which may have a substituent, or a chain alkenyl group which may have a substituent of R$^{101}$ in general formula (b-1). Here, R$^{104}$ and R$^{105}$ may be bonded to each other so as to form a ring.

R$^{104}$ and R$^{105}$ are preferably a chain alkyl group which may have a substituent, and are further preferably a linear or branched alkyl group, or a linear or branched fluorinated alkyl group.

The number of the carbon atoms of the chain alkyl group is preferably 1 to 10, is further preferably 1 to 7, and is still further preferably 1 to 3. The number of the carbon atoms of the chain alkyl group of R$^{104}$ and R$^{105}$ is preferably as small as possible within the range of the carbon number from the aspect that the solubility with respect to the resist solvent is improved. In the chain alkyl group of R$^{104}$ and R$^{105}$, a large number of the hydrogen atoms which are substituted with a fluorine atom is preferable from the aspect that the strength of the acid becomes stronger and transparency to high energy light of 200 nm or less or electron beam is improved.

The ratio of a fluorine atom in the chain alkyl group, that is, a fluorination rate is preferably 70% to 100, and is further preferably 90% to 100%, and a perfluoroalkyl group in which all hydrogen atoms are substituted with fluorine atoms is most preferable.

In the formula (b-2), V$^{102}$ and V$^{103}$ each independently represent a single bond, an alkylene group, or a fluorinated alkylene group, which is the same as that in V$^{101}$ in the formula (b-1).

In the formula (b-2), L$^{101}$ and L$^{102}$ each independently represent a single bond or an oxygen atom.

Anion Part of (b-3) Component

In the formula (b-3), R$^{106}$ to R$^{108}$ each independently represent an acyclic group which may have a substituent, a chain alkyl group which may have a substituent, or a chain alkenyl group which may have a substituent, which is the same as a cyclic group which may have a substituent, a chain alkyl group which may have a substituent, or a chain alkenyl group which may have a substituent of R$^{101}$ in general formula (b-1).

L$^{103}$ to L$^{105}$ each independently represent a single bond, —CO—, or —SO$_2$—.

Cation Part

In general formulae (b-1), (b-2), and (b-3), m is an integer of 1 or more, M'''$^{m+}$ is an m-valent onium cation, and preferred examples thereof include a sulfonium cation and an iodonium cation. Specific examples thereof include organic cations respectively represented by general formulae (ca-1) to (ca-5).

Specific examples of the preferred cation represented by general formula (ca-1) include the cations respectively represented by general formulae (ca-1-1) to (ca-1-74).

Specific examples of the preferred cation represented by general formula (ca-2) include a diphenyliodonium cation and a bis(4-tert-butylphenyl) iodonium cation.

Specific examples of the preferred cation represented by general formula (ca-3) include the cations respectively represented by general formulae (ca-3-1) to (ca-3-6).

Specific examples of the preferred cation represented by general formula (ca-4) include the cations respectively represented by general formulae (ca-4-1) and (ca-4-2).

Specifically, examples of the preferred cation represented by general formula (ca-5) include the cation represented by general formula (ca-5-1).

Among them, the cation part ((M'''$^{m+}$)$_{1/m}$) is preferably the cation represented by general formula (ca-1), and is further preferably the cations respectively represented by general formula (ca-1-1) to (ca-1-74).

In the resist composition of the present embodiment, the (B2) component may be used alone or two or more kinds thereof may be used in combination.

In the case where the resist composition contains the (B2) component, in the resist composition, the content of the (B2) component is preferably equal to or less than 50 parts by mass, is further preferably 1 to 40 parts by mass, and is still further preferably 5 to 30 parts by mass, with respect to 100 parts by mass of the (A) component.

When the content of the (B2) component is set in the above-described range, it is sufficient to form a pattern. In addition, when the respective components of the resist composition are dissolved in an organic solvent, it is easy to obtain a uniform solution, and the storage stability perform the component as a resist composition is improved, and thus the content is preferably in the above-described range.

Optional Components

The resist composition of the present embodiment may further contain other components (optional components) in addition to the (A) component and (B) component.

Examples of the optional components include a (D) component, an (E) component, an (F) component, and an (S) component as described below.

(D) Component: Acid Diffusion Control Agent Component

The resist composition of the present embodiment may contain an acid diffusion control agent component (hereinafter, referred to as "(D) component") in addition to the (A) component and the (B) component. The (D) component functions as a quencher (acid diffusion control agent) that traps an acid generated upon exposure on the resist composition.

Examples of the (D) component include a photodegradable base (D1) (hereinafter, referred to as "(D1) component) which is decomposed upon exposure to lose acid diffusion controllability, and a nitrogen-containing organic compound (D2) (hereinafter, referred to as "(D2) component) which does not correspond to the (D1) component.

Regarding (D1) Component

With the resist composition containing the (D1) component, it is possible to further improve the contrast between the exposed area and the unexposed area of the resist film at the time of forming the resist pattern.

The (D1) component is not particularly limited as long as the component which is decomposed upon exposure to lose acid diffusion controllability, and preferred examples thereof include one or more compounds selected from the group consisting of a compound (hereinafter, referred to as "(d1-1) component") represented by general formula (d1-1), a compound (hereinafter, referred to as "(d1-2) component") represented by general formula (d1-2), and a compound (hereinafter, referred to as "(d1-3) component") represented by general formula (d1-3).

Since the (d1-1) to (d1-3) components are decomposed in the exposed area of the resist film, the acid diffusion control properties (basicity) are lost. For this reason, the (d1-1) to (d1-3) components do not act as a quencher in the exposed area, but act as a quencher in the unexposed area of the resist film.

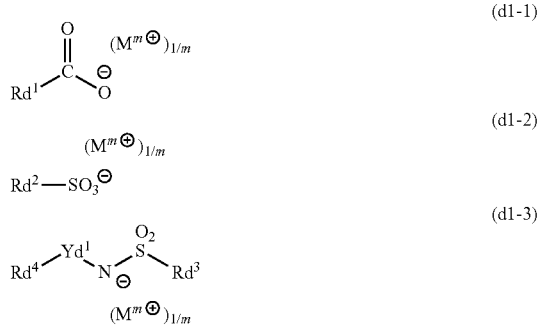

In the formula, $Rd^1$ to $Rd^4$ are a cyclic group which may have a substituent, a chain alkyl group which may have a substituent, or a chain alkenyl group which may have a substituent. Here, it is assumed that a fluorine atom is not bonded to the carbon atom adjacent to S atom in $Rd^2$ in general formula (d1-2). $Yd^1$ is a single bond or a divalent linking group. m is an integer of 1 or more, and $M^{m+}$'s each independently represent an m-valent organic cation.

(d1-1) Component

Anion Part

In the formula (d1-1), $Rd^1$ is a cyclic group which may have a substituent, a chain alkyl group which may have a substituent, or a chain alkenyl group which may have a substituent, and examples thereof include the same group as that of $R^{101}$ in general formula (b-1).

Among them, as $Rd^1$, an aromatic hydrocarbon group which may have a substituent, an aliphatic cyclic group which may have a substituent, and a chain alkyl group which may have a substituent are preferable. Examples of the substituent that the aforementioned groups may have a hydroxyl group, an oxy group, an alkyl group, aryl group, a fluorine atom, a fluorinated alkyl group, and lactone-containing cyclic groups respectively represented by general formulae (a2-r-1) to (a2-r-7), an ether bond, an ester bond, or a combination thereof. In the case where the ether bond and the ester bond are used as a substituent, the alkylene group may be used as being interposed therebetween. In this case, as a substituent, linking groups respectively represented by general formulae (y-al-1) to (y-al-5).

As the aromatic hydrocarbon group, a phenyl group or a naphthyl group is further preferable.

As the aliphatic cyclic group, a group obtained by removing one or more hydrogen atoms from polycycloalkane such as adamantane, norbornane, isobornane, tricyclodecane, and tetracyclododecane.

The number of carbon atoms of a chain alkyl group is preferably 1 to 10, and specific examples include a linear alkyl group such as a methyl group, an ethyl group, a propyl group, a butyl group, a pentyl group, a hexyl group, a heptyl group, an octyl group, a nonyl group, and a decyl group; and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group are preferable.

In the case where the linear alkyl group is a fluorinated alkyl group having a fluorine atom or a fluorinated alkyl group as a substituent, the number of carbon atoms of the fluorinated alkyl group is preferably 1 to 11, is further preferably 1 to 8, and is still further preferably 1 to 4. The fluorinated alkyl group may contain other atoms in addition to the fluorine atom. Examples of other atoms in addition to the fluorine atom include an oxygen atom, a sulfur atom, and a nitrogen atom.

$Rd^1$ is preferably a fluorinated alkyl group in which at least one hydrogen atom of a linear alkyl group is substituted with a fluorine atom, and is particularly preferably a fluorinated alkyl group (a linear perfluoroalkyl group) in which all of the hydrogen atoms of a linear alkyl group are substituted with a fluorine atom.

Hereinafter, specific examples of the preferred anion part of the (d1-1) component will be described.

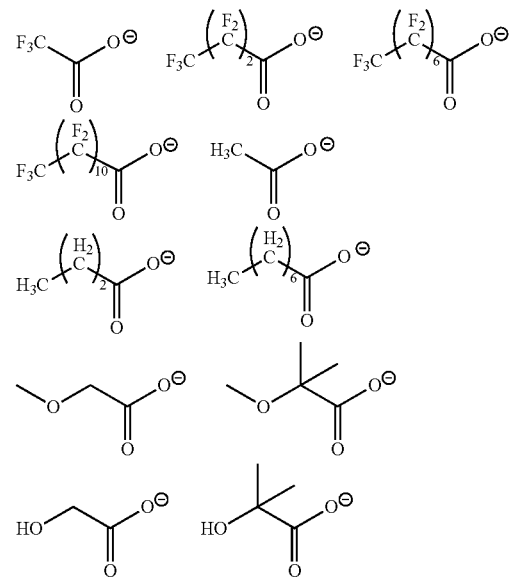

-continued

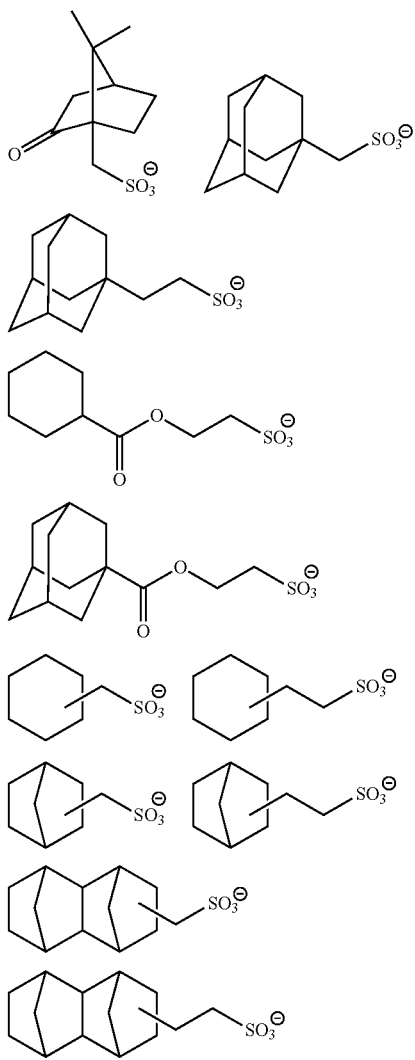

Cation Part

In general formula (d1-1), $M^{m+}$ is an m-valent organic cation.

As the organic cation of $M^{m+}$, the same cations as those respectively represented by general formulae (ca-1) to (ca-5) are preferable, the cation represented by general formula (ca-1) is further preferable, and the cations respectively represented by general formulae (ca-1-1) to (ca-1-74) are still further preferable.

The (d1-1) component may be used alone, or two or more kinds thereof may be used in combination.

(d1-2) Component

Anion Part

In general formula (d1-2), $Rd^2$ is a cyclic group which may have a substituent, a linear alkyl group which may have a substituent, or a linear alkenyl group which may have a substituent, and examples thereof include the same groups as those of $R^{101}$ in general formula (b-1).

Here, it is assumed that a fluorine atom is not bonded to the carbon atom adjacent to S atom in $Rd^2$ (the carbon atom is not fluorine-substituted). With this, the anion of the (d1-2) component becomes an appropriately weak acid anion, and thus the quenching ability as the (D) component is improved.

The $Rd^2$ is preferably a chain alkyl group which may have a substituent, or aliphatic cyclic group which may have a substituent. The number of carbon atoms of the chain alkyl group is preferably 1 to 10, and is further preferably 3 to 10. As the aliphatic cyclic group, a group (which may have a substituent) obtained by removing one or more hydrogen atoms from adamantane, norbornane, isobornane, tricyclodecane, and tetracyclododecane, and is further preferably a group obtained by removing one or more hydrogen atoms from the camphor.

The hydrocarbon group for $Rd^2$ may have a substituent, and examples of the substituent include a substituent which is the same as the substituent which may be contained in the hydrocarbon group (an aromatic hydrocarbon group, an aliphatic cyclic group, a chain alkyl group) for $Rd^1$ of general formula (d1-1).

Specific preferred examples of the anion part having the (d1-2) component will be described as follows.

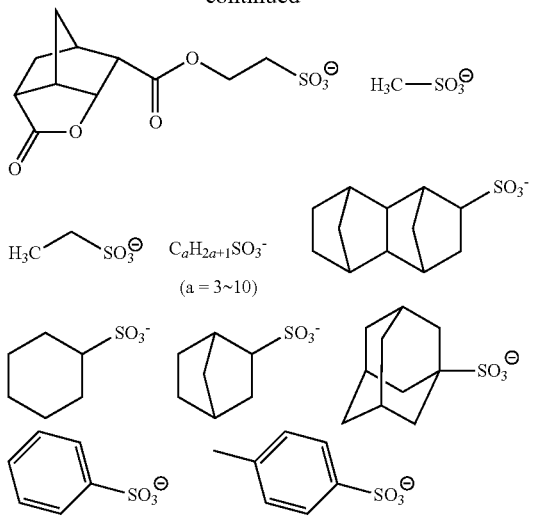

Cation Part

In general formula (d1-2), $M^{m+}$ is an m-valent organic cation, and is the same as $M^{m+}$ in general formula (d1-1)

The (d1-2) component may be used alone, or two or more kinds thereof may be used in combination.

(d1-3) Component

Anion Part

In general formula (d1-3), $Rd^3$ is a cyclic group which may have a substituent, a chain alkyl group which may have a substituent, or a chain alkenyl group which may have a substituent, and examples thereof include the same group as that of $R^{101}$ in general formula (b-1), and a cyclic group containing a fluorine atom, a chain alkyl group, or a chain alkenyl group is preferable. Among them, the fluorinated alkyl group is preferable, and the same grout as the fluorinated alkyl group of $Rd^1$ is further preferable.

In the formula (d1-3), $Rd^4$ is a cyclic group which may have a substituent, a chain alkyl group which may have a substituent, or a chain alkenyl group which may have a substituent, and examples thereof include the same group as that of $R^{101}$ in general formula (b-1).

Among them, the alkyl group which may have a substituent, the alkoxy group, the alkenyl group, and the cyclic group are preferable.

The alkyl group for $Rd^4$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. At least one hydrogen atom in an alkyl group for $Rd^4$ may be substituted with a hydroxyl group, a cyano group, and the like.

The alkoxy group for $Rd^4$ is preferably an alkoxy group having 1 to 5 carbon atoms, and specific examples of the alkoxy group having 1 to 5 carbon atoms include a methoxy group, an ethoxy group, an n-propoxy group, an iso-propoxy group, an n-butoxy group, and a tert-butoxy group. Among them, the methoxy group and the ethoxy group are preferable.

Examples of the alkenyl group for $Rd^4$ include the same group as that of $R^{101}$ in general formula (b-1), and a vinyl group, a propenyl group (an allyl group), a 1-methyl propenyl group, and a 2-methyl propenyl group are preferable. These groups may further have an alkyl group having 1 to 5 carbon atoms or a halogenated alkyl group having 1 to 5 carbon atoms as a substituent.

Examples of the cyclic group for $Rd^4$ include the same group as that of $R^{101}$ in general formula (b-1), and an alicyclic group which is obtained by removing one or more hydrogen atom from cycloalkane such as cyclopentane, cyclohexane, adamantane, norbornane, isobornane, tricyclodecane, and tetracyclododecane, or an aromatic group such as a phenyl group and a naphthyl group is preferable. In the case where $Rd^4$ is an alicyclic group, the resist composition is dissolved well in an organic solvent, and thus the lithography properties become excellent. Further, in the case where $Rd^4$ is an aromatic group, in the lithography in which EUV or the like is set as an exposure light source, the resist composition is excellent in the light absorption efficiency, and thus the sensitivity and the lithography properties become excellent.

In the formula (d1-3), $Yd^1$ is a single bond or a divalent linking group.

The divalent linking group for $Yd^1$ is not particularly limited, and examples thereof include a divalent hydrocarbon group which may have a substituent (an aliphatic hydrocarbon group and an aromatic hydrocarbon group), and a divalent linking group containing a heteroatom. The aforementioned examples are the same as the divalent hydrocarbon group which may have a substituent, and the divalent linking group containing a heteroatom, which are exemplified in the description of the divalent linking group for $Ya^{21}$ in general formula (a2-1).

The $Yd^1$ is preferably a carbonyl group, an ester bond, an amide bond, an alkylene group, or a combination thereof. The alkylene group is preferably a linear or branched alkylene group, and is further preferably a methylene group or an ethylene group.

Specific preferred examples of the anion part of the (d1-3) component will be described as follows.

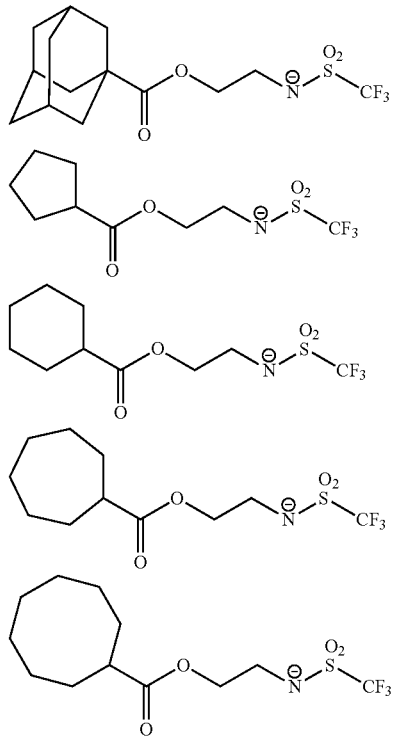

127
-continued
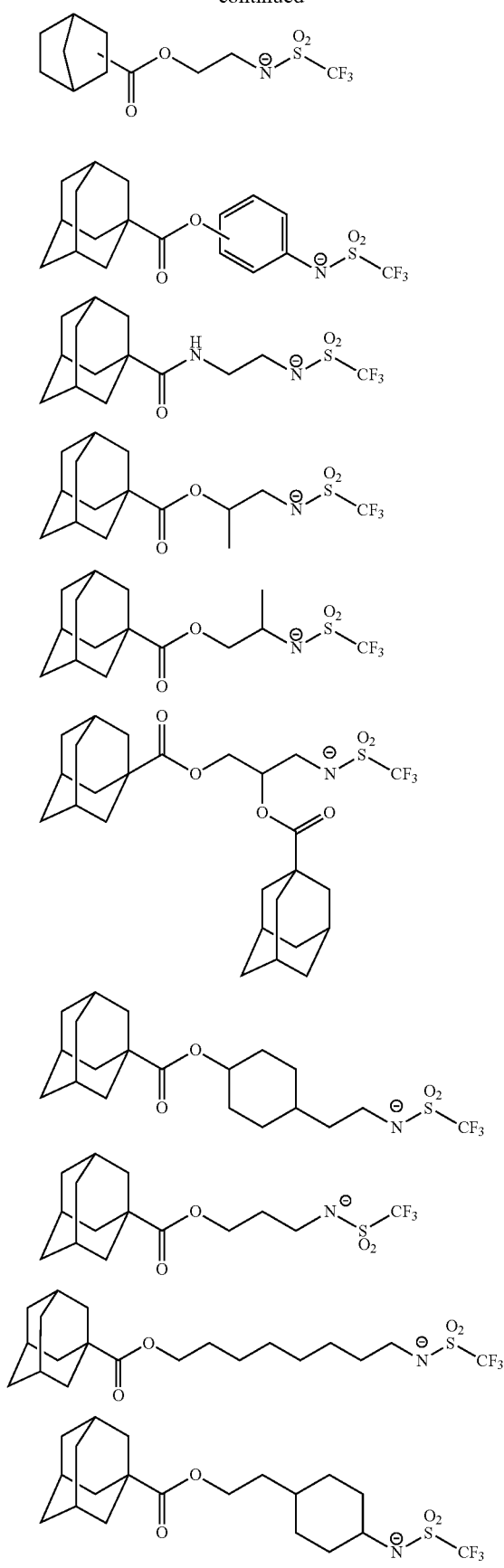
128
-continued
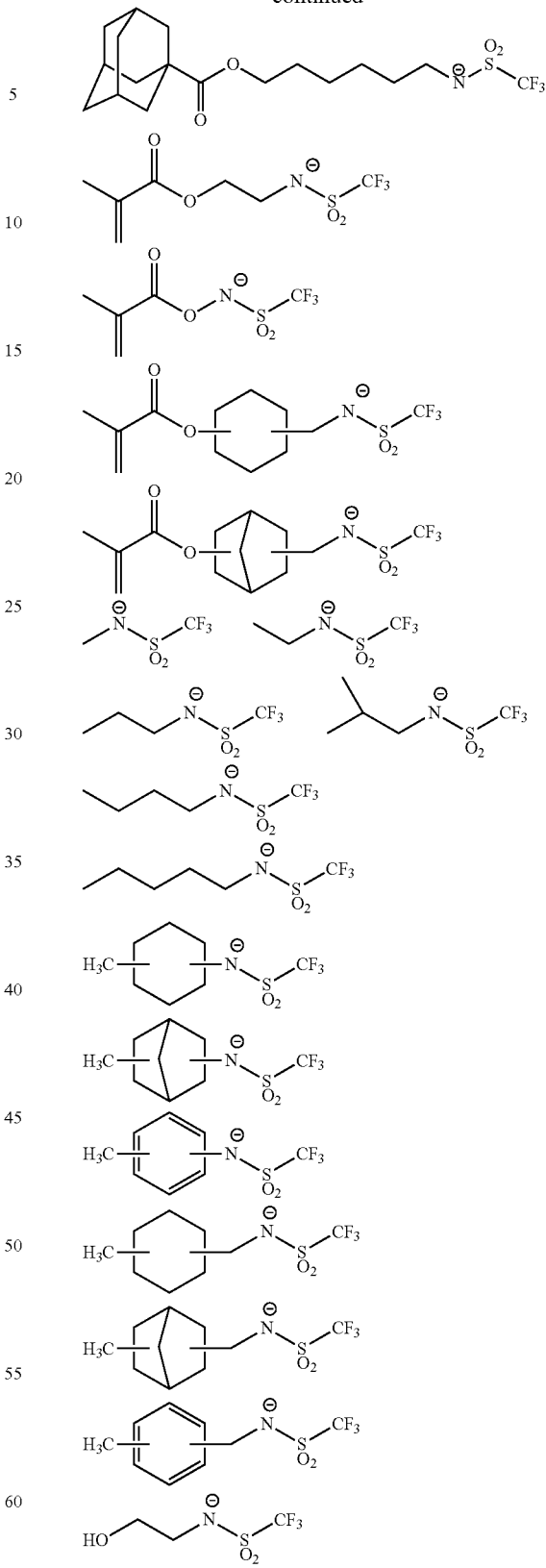
Cation Part
In the formula (d1-3), $M^{m+}$ is an m-valent organic cation, and is the same as $M^{m+}$ in general formula (d1-1)

The (d1-3) component may be used alone, or two or more kinds thereof may be used in combination.

The (D1) component may be obtained by using at least one of the (d1-1) to (d1-3) components, or using two or more kinds of components in combination.

In the case where the resist composition contains the (D1) component, in the resist composition, the content of the (D1) component is preferably 0.5 to 10 parts by mass, is further preferably 0.5 to 8 parts by mass, and is still further preferably 1 to 6 parts by mass, with respect to 100 parts by mass of the (A) component.

When the content of the (D1) component is equal to or greater than the preferred lower limit, it is easy to obtain particularly preferable lithography properties and resist pattern shape. On the other hand, when the (D1) component is equal to or lower than the upper limit, it is possible to maintain the excellent sensitivity, and to obtain excellent throughput.

Method for Preparing (D1) Component:

The method of preparing the (d1-1) component and the (d1-2) component is not particularly limited, and it can be prepared by using the conventional well-known methods.

In addition, the method of preparing the (d1-3) component is not particularly limited, and for example, the same method as the method disclosed in US2012-0149916.

Regarding (D2) Component

As the acid diffusion control agent component, a nitrogen-containing organic compound component (hereinafter, referred to as "(D2) component") which does not correspond to the (D1) component.

The (D2) component is not particularly limited as long as it acts as the acid diffusion control agent, and does not correspond to the (D1), and may be optionally used from the well-known components. Among them, aliphatic amine is preferable, and particularly, secondary aliphatic amine and tertiary aliphatic amine are further preferable.

The aliphatic amine is amine having one or more aliphatic groups, and the number of carbon atoms of the aliphatic group is preferably 1 to 12.

Examples of the aliphatic amine include amine (alkyl amine or alkyl alcohol amine) in which at least one hydrogen atom of ammonia $NH_3$ is substituted with an alkyl group having equal to or less than 12 carbon atoms, or a hydroxyalkyl group or cyclic amine.

Specific examples of the alkyl amine and the alkyl alcohol amine include monoalkyl amines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamine such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, and tri-n-dodecylamine; and alkyl alcohol amine such as diethanolamine, triethanolamine, diisopropanolamine, triisopropanolamine, di-n-octanolamine, and tri-n-octanolamine. Among them, trialkylamine having 5 to 10 carbon atoms is further preferable, and tri-n-pentylamine or tri-n-octylamine is particularly preferable.

Examples of the cyclic amine include a heterocyclic compound containing a nitrogen atom as a heteroatom. The heterocyclic compound may be a monocyclic compound (aliphatic monocyclic amine) or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclocyclo[4.3.0]-5-nonen, 1,8-diazabicyclocyclo[5.4.0]-7-undecene, hexamethylenetetramine, and 1,4-diazabicyclo[2.2.2] octane.

Examples of other aliphatic amines include tris(2-methoxymethoxyethyl) amine, tris{2-(2-methoxyethoxy) ethyl} amine, tris{2-(2-methoxyethoxymethoxy) ethyl} amine, tris{2-(1-methoxyethoxy) ethyl} amine, tris{2-(1-ethoxyethoxy) ethyl} amine, tris{2-(1-ethoxypropoxy) ethyl} amine, tris[2-{2-(2-hydroxyethoxy) ethoxy} ethyl] amine, and triethanolamine triacetate. Among them, triethanolamine triacetate is preferable.

In addition, aromatic amine may be used as the (D2) component.

Examples of the aromatic amine include 4-dimethyl aminopyridine, pyrrole, indole, pyrazole, imidazole, and derivatives thereof, tribenzylamine, 2,6-diisopropylaniline, and N-tert-butoxycarbonylpyrrolidine.

The (D2) component may be used alone, or two or more kinds thereof may be used in combination.

In the case where the resist composition contains the (D2) component in the resist composition, the content of the (D2) component is generally 0.01 to 5 parts by mass with respect to 100 parts by mass of the (A) component. When the content is within the above range, the resist pattern shape, the post exposure stability, and the like are improved.

(E) Component: At Least One Compound Selected from the Group Consisting of an Organic Carboxylic Acid and an Oxo Acid of Phosphorus, and Derivatives Thereof In the resist composition of the present embodiment, in order to prevent the sensitivity from being deteriorated and to improve the resist pattern shape and the post exposure stability, at least one compound (E) (hereinafter, referred to as "(E) component") selected from the group consisting of an organic carboxylic acid and an oxo acid of phosphorus, and derivatives thereof can be contained as an optional component.

As the organic carboxylic acid, for example, an acetic acid, a malonic acid, a citric acid, a malic acid, a succinic acid, a benzoic acid, and a salicylic acid are preferable.

Examples of the oxo acid of phosphorus include a phosphoric acid, a phosphonic acid, and a phosphinic acid, and among them, a phosphonic acid is particularly preferable.

Examples of the derivative of the oxo acid of phosphorus include ester obtained by substituting the hydrogen atom of the oxo acid with a hydrocarbon group, and examples of the hydrocarbon group include an alkyl group having 1 to 5 carbon atoms, and an aryl group having 6 to 15 carbon atoms.

Examples of the derivative of the phosphoric acid include phosphate ester such as phosphoric acid di-n-butyl ester and phosphoric acid diphenyl ester.

Examples of the derivative of the phosphonic acid include phosphonic acid ester such as phosphonic acid dimethyl ester, phosphonic acid-di-n-butyl ester, phenyl phosphonic acid, diphosphonic acid diphonyl ester, and phosphonic acid dibenzyl.

Examples of the derivative of the phosphinic acid include phosphinic acid ester and a phenyl phosphinic acid.

In the resist composition of the present embodiment, the (E) component may be used alone, or two or more kinds thereof may be used in combination.

In the case where the resist composition contains the (E) component, the content of the (E) component in the resist composition is generally 0.01 to 5 parts by mass with respect to 100 parts by mass of the (A) component.

(F) Component: Fluorine Additive Component

The resist composition of the present embodiment may contain a fluorine additive component (hereinafter, referred to as "(F) component") so as to impart water repellency to the resist film.

Examples of the (F) component include a fluorine-containing polymer compound which is disclosed in Japanese Unexamined Patent Application, Publication No. 2010-002870, disclosed in Japanese Unexamined Patent Application, Publication No. 2010-032994, disclosed in Japanese Unexamined Patent Application, Publication No. 2010-277043, disclosed in Japanese Unexamined Patent Application, Publication No. 2011-13569, disclosed in Japanese Unexamined Patent Application, Publication No. 2011-128226.

Specific examples of the (F) component include a polymer having a structural unit (f1) represented by general formula (f1-1). Examples of the preferred polymer include a polymer (homopolymer) composed of a structural unit (f1) represented by general formula (f1-1) only; a copolymer of the structural unit (f1) and the structural unit (a1); and a copolymer of the structural unit (f1), a structural unit derived from an acrylic acid or a meth acrylic acid, and the structural unit (a1). Here, the structural unit (a1) which is copolymerized with the structural unit (f1) is preferably a structural unit derived from 1-ethyl-1-cyclooctyl (meth)acrylate, and a structural unit derived from 1-methyl-1-adamantyl (meth)acrylate.

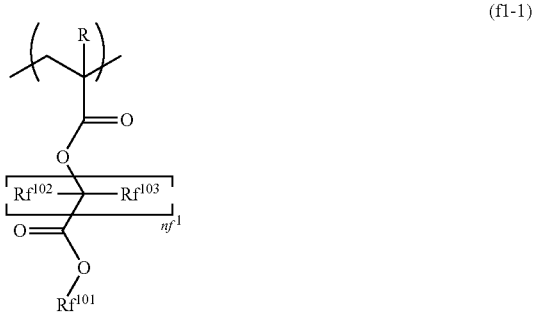

(f1-1)

In the formula, R is the same as described above, $Rf^{102}$ and $Rf^{103}$ each independently represent a hydrogen atom, a halogen atom, an alkyl group having 1 to 5 carbon atoms, or a halogenated alkyl group having 1 to 5 carbon atoms, $Rf^{102}$ and $Rf^{103}$ may be the same as or different from each other. $nf^1$ is an integer of 1 to 5, $Rf^{101}$ is an organic group containing a fluorine atom.

In general formula (f1-1), R which is bonded to an α-position carbon atom is the same as described above. R is preferably a hydrogen atom or a methyl group.

In general formula (f1-1), examples of the halogen atom of $Rf^{102}$ and $Rf^{103}$ include a fluorine atom, a chlorine atom, a bromine atom, and an iodine atom, among them, the fluorine atom is particularly preferable. The alkyl group having 1 to 5 carbon atoms of $Rf^{102}$ and $Rf^{103}$ is the same as the alkyl group having 1 to 5 carbon atoms for R, and is preferably a methyl group or an ethyl group. Specific examples of the halogenated alkyl group having 1 to 5 carbon atoms for $Rf^{102}$ and $Rf^{103}$ include a group in which at least one hydrogen atom of an alkyl group having 1 to 5 carbon atoms is substituted with a halogen atom.

Examples of the halogen atom include a fluorine atom, a chlorine atom, a bromine atom, and an iodine atom, and the fluorine atom is particularly preferable. Among them, as $Rf^{102}$ and $Rf^{103}$, a hydrogen atom, a fluorine atom, or an alkyl group having 1 to 5 carbon atoms is preferable, and a hydrogen atom, a fluorine atom, a methyl group, or an ethyl group is further preferable.

In general formula (f1-1), $nf^1$ is an integer of 1 to 5, is preferably an integer of 1 to 3, and is further preferably an integer of 1 or 2.

In general formula (f1-1), $Rf^{101}$ is an organic group containing a fluorine atom, and is preferably a hydrocarbon group containing a fluorine atom.

The hydrocarbon group containing a fluorine atom may be a linear, branched, or cyclic hydrocarbon group, and the number of carbon atoms of the hydrocarbon group is preferably 1 to 20, is further preferably 1 to 15, and particularly preferably 1 to 10.

Further, in the hydrocarbon group containing a fluorine atom, 25% or more of hydrogen atom in the hydrocarbon group is preferably fluorinated, 50% or more of hydrogen atom is further preferably fluorinated, and 60% or more of hydrogen atom is particularly preferably fluorinated from the aspect that the hydrophobicity of the resist film at the time of immersion exposure is enhanced.

Among them, as $Rf^{101}$, a fluorinated hydrocarbon group having 1 to 6 carbon atoms is preferable, and trifluoromethyl group, —$CH_2$—$CF_3$, —$CH_2$—$CF_2$—$CF_3$, —$CH(CF_3)_2$, —$CH_2$—$CH_2$—$CF_3$, and —$CH_2$—$CH_2$—$CF_2$—$CF_2$—$CF_3$ are particularly preferable.

The mass average molecular weight (Mw) (in terms of the standard polystyrene by gel permeation chromatography) of the (F) component is preferably 1,000 to 50,000, is further preferably 5,000 to 40,000, and is most preferably 10,000 to 30,000. When the mass average molecular weight is equal to or less than the upper limit of the aforementioned range, the solubility with respect to a resist solvent is sufficient in the case where the (F) component is used as a resist, and when the mass average molecular weight of the (F) component is equal to or greater than the lower limit of the aforementioned range, dry etching resistance and a resist pattern cross-sectional shape are improved.

The dispersivity (Mw/Mn) of the (F) component is preferably 1.0 to 5.0, is further preferably 1.0 to 3.0, and is most preferably 1.2 to 2.5.

In the resist composition of the present embodiment, the (F) component may be used alone, or two or more kinds thereof may be used in combination.

In the case where the resist composition contains the (F) component, the content of the (F) component is generally 0.5 to 10 parts by mass with respect to 100 parts by mass of the (A) component.

(S) Component: Organic Solvent Component

The resist composition of the present embodiment can be prepared by dissolving a resist material into an organic solvent component (hereinafter, referred to as "(S) component").

The (S) component may be a component which can form a homogeneous solution by dissolving the respective components to be used, and any one of well-known conventional solvents of the chemically amplified resist composition is properly selected so as to be used as the (S) component.

Examples of the (S) component include lactones such as γ-butyrolactone; ketones such as acetone, methyl ethyl ketone, cyclohexanone, methyl-n-pentyl ketone, methyl isopentyl ketone, and 2-heptanone; polyhydric alcohols such as ethylene glycol, diethylene glycol, propylene glycol, and dipropylene glycol; derivatives of polyhydric alcohols such as a compound having an ether bond such as ethylene glycol monoacetate, diethylene glycol monoacetate, propylene glycol monoacetate, or dipropylene glycol monoacetate, and a compound having an ester bond such as monoalkyl ether or monophenyl ether such as monomethyl ether, monoethyl ether, monopropyl ether, and monobutyl ether of the compound having the polyhydric alcohol or the ester bond [among them, propylene glycol monomethyl ether acetate (PGMEA), and propylene glycol monomethyl ether (PGME), are preferable]; cyclic ethers such as dioxane, esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethyl benzyl ether, cresyl methyl ether, diphenyl ether, dibenzyl ether, phenetole, butyl phenyl ether, ethyl benzene, diethyl benzene, pentyl benzene, isopropyl benzene, toluene, xylene, cymene, and mesitylene; and dimethyl sulfoxide (DMSO).

In the resist composition of the present embodiment, the (S) component may be used alone or may be used as a mixed solvent of two or more kinds thereof.

Among them, PGMEA, PGME, γ-butyrolactone, EL, and cyclohexanone are preferable.

In addition, a mixed solvent obtained by mixing PGMEA and a polar solvent is also preferable. The mixing ratio (mass ratio) may be properly determined in consideration of the compatibility of the PGMEA with the polar solvent, and the ratio is preferably 1:9 to 9:1, and is further preferably 2:8 to 8:2.

More specifically, in the case of mixing EL or cyclohexane as the polar solvent, the mass ratio of PGMEA to EL or cyclohexane is preferably 1:9 to 9:1, and is further preferably 2:8 to 8:2. In addition, in the case of mixing PGME as a polar solvent, the mass ratio of PGMEA to PGME is preferably 1:9 to 9:1, is further preferably 2:8 to 8:2, and still further preferably 3:7 to 7:3. In addition, a mixed solvent obtained by mixing PGMEA, PGME, and cyclohexane is also preferable.

Further, as the (S) component, a mixed solvent obtained by mixing at least one selected from PGMEA and EL with γ-butyrolactone is also preferable. In this case, as the mixing ratio, the mass ratio of the former to the latter is preferably set to be 70:30 to 95:5.

The content of the (S) component used is not particularly limited, and is properly set in accordance with the coated film thickness at a concentration that can be applied to a substrate or the like. Generally, the (S) component is used such that the concentration of solid contents of the resist composition is 1 to 20% by mass, and is preferably 2 to 15% by mass.

It is possible to contain miscible additives to the resist composition of the present embodiment as necessary, for example, in order to improve the performance of the resist film, an additional resin, a dissolution inhibitor, a plasticizer, a stabilizer, a colorant, a halation inhibitor, and a dye can be added and contained.

Method for Forming Resist Pattern

A method for forming a resist pattern according to the present embodiment of the present invention includes a step of forming a resist film on a support by using the resist composition according to the present embodiment, a step of exposing the resist film, and a step of developing the exposed resist film to form a resist pattern.

The method for forming a resist pattern of the present embodiment can be performed in the following manner.

First, the support is coated with the resist composition according to the present embodiment by using a spinner, and the coated film is subjected to a bake (Post Applied Bake (PAB)) treatment at a temperature of 80° C. to 150° C. for 40 to 120 seconds, preferably for 60 to 90 seconds, so as to form a resist film.

Then, the resist film is exposed via a mask (a mask pattern) on which a predetermined pattern is formed, or is selectively exposed without the mask pattern by lithography or the like due to direct irradiation of an electron beam by using an exposure apparatus such as an electron beam lithography apparatus, and an EUV exposure apparatus, and then is subjected to a bake (Post Exposure Bake (PEB)) treatment at a temperature of 80° C. to 150° C. for 40 to 120 seconds (preferably for 60 to 90 seconds).

Subsequently, the resist film is subjected to the developing treatment. In the developing treatment, an alkali developing solution is used in the case of the alkali developing process, and a developing solution (organic developing solution) containing an organic solvent is used in the case of the solvent developing process.

After the developing treatment, a rinse treatment is preferably performed. In the rinse treatment, water rinsing is preferably performed by using pure water in the case of the alkali developing process, and a rinsing liquid containing an organic solvent is preferably used in the case of the solvent developing process.

In the case of the solvent developing process, a treatment of removing the developing solution or the rinsing liquid which is attached on the pattern by a supercritical fluid may be performed after the developing treatment and the rinse treatment.

Drying is performed after the developing treatment and the rinse treatment. In addition, in some cases, a bake (post bake) treatment may be performed after the developing treatment.

In this way, it is possible to form a resist pattern.

The support is not particularly limited, and it is possible to use conventionally well-known supports. Examples thereof include a substrate for electronic parts and a substrate on which a prescribed wiring pattern is formed. More specifically, examples of the support include a metallic substrate such as a silicon wafer, copper, chromium, iron, and aluminum, and a glass substrate. As the wire pattern material, for example, it is possible to use copper, aluminum, nickel, and gold.

In addition, a support obtained by providing an inorganic and/or organic film on the substrate may be used as the support. Examples of the inorganic film include an inorganic antireflection film (inorganic BARC). Examples of the organic film include an organic antireflection film (organic BARC) or a lower layer organic film obtained by using a multilayer resist method.

Here, the multilayer resist method is a method of providing at least a single layer of organic film (lower layer organic film) and at least single layer of resist film (upper layer resist film) on the substrate, and then performing the patterning of the lower layer organic film by setting the resist pattern formed on the upper layer resist film as a mask. With such a method, it is possible to form a pattern with a high aspect ratio. That is, according to the multilayer resist method, since the required thickness can be secured by the lower layer organic film, the resist film can be thinned and a fine pattern with the high aspect ratio can be formed.

The multilayer resist method basically includes a method (two-layer resist method) of setting a two-layer structure of an upper layer resist film and a lower layer organic film, and a method (three-layer resist method) of setting a multilayer (three or more layers) structure of providing one or more intermediate layers (thin metal film and the like) between the upper layer resist film and the lower layer organic film.

The wavelength used in the exposure is not particularly limited, and examples thereof include radiations such as ArF excimer laser, KrF excimer laser, $F_2$ excimer laser, extreme ultraviolet rays (EUV), vacuum ultraviolet rays (VUV), electron beams (EB), X rays, and soft X rays. The resist composition is highly useful when being used for KrF excimer laser, ArF excimer laser, EB or EUV, is further useful when being used for ArF excimer laser, EB or EUV, and is particularly useful when being used for EB or EUV.

As a method for exposing a resist film, a typical exposure (dry exposure) performed in an inert gas such as air or nitrogen, or liquid immersion lithography may be employed.

The liquid immersion lithography is an exposing method performed in such a manner that a space between a resist film and a lens at the lowermost position of an exposure apparatus is filled with a solvent (liquid immersion medium) having a refractive index larger than the refractive index of air, and exposure (immersion exposure) is performed in that state.

The liquid immersion medium is preferably a solvent having a refractive index which is larger than refractive index of air, and is smaller than the refractive index of the resist film to be exposed. The refractive index of the solvent is not particularly limited as long as it is within the range.

Examples of the solvent having a refractive index which is larger than refractive index of air, and is smaller than the refractive index of the resist film include water, a fluorinated inert liquid, a silicon solvent, and a hydrocarbon solvent.

Specific examples of the fluorinated inert liquid include a liquid having a fluorine compound as a main component, such as $C_3HCl_2F_5$, $C_4F_9OCH_3$, $C_4F_9OC_2H_5$, and $C_5H_3F_7$, and the boiling point thereof is preferably 70° C. to 180° C., and is further preferably 80° C. to 160° C. When the fluorinated inert liquid has the boiling point within the above-described range, after completion of the exposure, the medium used for the liquid immersion can be removed by a simple method.

The fluorinated inert liquid is particularly preferably a perfluoroalkyl compound in which all hydrogen atoms of an alkyl group are substituted with a fluorine atom. Specific examples of the perfluoroalkyl compound include a perfluoroalkyl ether compound and a perfluoroalkylamine compound.

Further, specifically, examples of the perfluoroalkyl ether compound include perfluoro (2-butyl-tetrahydrofuran) (boiling point 102° C.), and examples of the perfluoroalkylamine compound include perfluorotributylamine (boiling point of 174° C.).

As the liquid immersion medium, water is preferably used in terms of cost, safety, environmental problems, and versatility.

Examples of an alkali developing solution used for the developing treatment in the alkali developing process include 0.1 to 10% by mass of tetramethyl ammonium hydroxide (TMAH) aqueous solution.

The organic solvent containing organic developing solution used for the developing treatment in the solvent developing process may be a solvent in which the (A) component ((A) component before exposure) can be dissolved, and can be appropriately selected from well-known organic solvents. Specific examples thereof include a polar solvent such as a ketone-based solvent, an ester-based solvent, an alcohol-based solvent, a nitrile-based solvent, an amide-based solvent, and an ether-based solvent, and a hydrocarbon solvent.

The ketone-based solvent is an organic solvent containing C—C(=O)—C in the structure. The ester-based solvent is an organic solvent containing C—C(=O)—O—C in the structure. The alcohol-based solvent is an organic solvent containing an alcoholic hydroxyl group in the structure. The "alcoholic hydroxyl group" means a hydroxyl group which is bonded to a carbon atom of an aliphatic hydrocarbon group. The nitrile-based solvent is an organic solvent containing a nitrile group in the structure. The amide-based solvent is an organic solvent containing an amide group in the structure. The ether-based solvent is an organic solvent containing C—O—C in the structure.

In the organic solvent, an organic solvent which contains various kinds of functional groups characterizing each solvent in the structure is also present. In this case, the organic solvent is regarded to correspond to all of the respective organic solvents which contain each of the functional groups that the organic solvent has. For example, diethylene glycol monomethyl ether corresponds to any one of the alcohol-based solvent and the ether-based solvent in the above-described solvent kinds.

The hydrocarbon solvent consists of hydrocarbons which may be halogenated, and does not contain a substituent except for a halogen atom. Examples of the halogen atom include a fluorine atom, a chlorine atom, a bromine atom, and an iodine atom, and among them, the fluorine atom is preferable.

Among the above examples, the organic solvent containing an organic developing solution is preferably a polar solvent, and the ketone-based solvent, the ester-based solvent, and the nitrile-based solvent are preferable.

Examples of the ketone-based solvent include 1-octanone, 2-octanone, 1-nonanone, 2-nonanone, acetone, 4-heptanone, 1-hexanone, 2-hexanone, diisobutyl ketone, cyclohexanone, methyl cyclohexanone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, propylene carbonate, γ-butyrolactone, and methyl amyl ketone (2-heptanone). Among them, the ketone-based solvent is preferably methyl amyl ketone (2-heptanone).

Examples of the ester-based solvent include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate, and propyl-3-methoxypropionate. Among them, the ester-based solvent is preferably butyl acetate.

Examples of the nitrile-based solvent include acetonitrile, propionitrile, valeronitrile, and butyronitrile.

In organic developing solution, well-known additives can be mixed as necessary. Examples of the additives include a surfactant. The surfactant is not particularly limited, and examples thereof include an ionic or nonionic fluorine-based and/or silicon-based surfactant.

The surfactant is preferably a nonionic surfactant, and is further preferably a nonionic fluorine-based surfactant or a nonionic silicon-based surfactant.

In the case of mixing the surfactant, the mixing content is generally 0.001 to 5% by mass, is preferably 0.005 to 2% by mass, and is further preferably 0.01 to 0.5% by mass, with respect to the entire content of the organic developing solution.

The developing treatment can be implemented by using a well-known rinsing method, and examples thereof include a method of dipping the support into the developing solution a certain period of time (a dipping method), a method of raising the developing solution on the surface of the support by surface tension and resting for a certain period of time (a puddle method) a method of spraying the developing solution on the surface of the support (a spray method), and a method of continuously coating a support which rotates at a constant speed with the developing solution while scanning a coating nozzle (a dynamic dispense method).

As the organic solvent containing a rinsing liquid used in the rinse treatment after the developing treatment in the solvent developing process, an organic solvent in which a resist pattern is not easily dissolved can be used by appropriately selected from the organic solvents exemplified as the organic solvent used in the organic developing solution. Typically, at least one solvent selected from a hydrocarbon solvent, a ketone-based solvent, an ester-based solvent, an alcohol-based solvent, an amide-based solvent, and an ether-based solvent is used. Among them, at least one selected from the hydrocarbon solvent, the ketone-based solvent, the ester-based solvent, the alcohol-based solvent, and the amide-based solvent is preferably used, at least one selected from the alcohol-based solvent and the ester-based solvent is further preferably used, and the alcohol-based solvent is particularly preferable.

The alcohol-based solvent used in the rinsing liquid is preferably monohydric alcohol having 6 to 8 carbon atoms, or the monohydric alcohol may be linear, branched, or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol, and benzyl alcohol. Among them, 1-hexanol, 2-heptanol, and 2-hexanol are preferable, and 1-hexanol and 2-hexanol are further preferable.

These organic solvents may be used alone, or two or more kinds thereof may be used in combination. In addition, an organic solvent other than the above-described organic solvents may be used in the mixture with water. Here, when it comes to the developing properties, the mixing content in the rinsing liquid is preferably equal to or less than 30% by mass, is further preferably equal to or less than 10% by mass, is still further preferably equal to or less than 5% by mass, and is particularly preferably equal to or less than 3% by mass with respect to the total content of the rinsing liquid.

In the rinsing liquid, well-known additives can be mixed as necessary. Examples of the additives include a surfactant. Examples of the surfactant include the same surfactant as described above, and a nonionic surfactant is preferable, a nonionic fluorine-based surfactant or a nonionic silicon-based is further preferable.

In the case of mixing the surfactant, the mixing content is generally 0.001 to 5% by mass, is preferably 0.005 to 2% by mass, and is further preferably 0.01 to 0.5% by mass, with respect to the entire content of the rinsing liquid.

The rinse treatment (washing treatment) using a rinsing liquid can be implemented by using a well-known rinsing method. Examples of a method of the rinse treatment include a method of continuously coating a support which rotates at a constant speed with the rinsing liquid (a rotary coating method), a method of dipping the support into the rinsing liquid (a dip method) for a certain period of time, and a method of spraying the rinsing liquid to the surface of the support (a spray method).

In the resist composition of the present embodiment, the resin component (A1) having the structural unit (a0) represented by general formula (a0-1), and the compound (B1) represented by general formula (b1) are used in combination. Due to high affinity between the (A1) component and the (B1) component, the (B1) component is easy to uniformly disperse in the resist film. As a result, in the method for forming a resist pattern of the embodiment as described above, it is presumed that the satisfactory development contrast is obtained, high sensitivity and improved lithography properties are realized, and thus a resist pattern having an excellent shape can be formed.

EXAMPLES

Hereinafter, the present invention will be more specifically described with reference to examples; however, the invention is not limited thereto.

In the present examples, a compound represented by chemical formula (1) is denoted as a "compound (1)", and the same is applied to other compounds represented by other chemical formulae.

Preparation of Base Material Component (Polymer)

Polymers A-1 to A-6, which were used in Examples, were obtained by performing the radical polymerization of the following monomers which correspond to structural units for constituting each polymer at a predetermined molar ratio.

(a21)

-continued (a01)

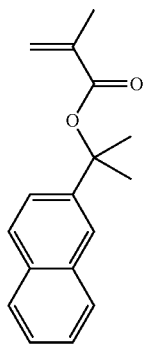

(a91)

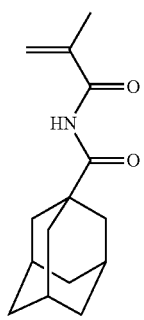

(st1)

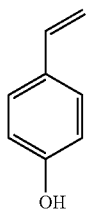

(a11)

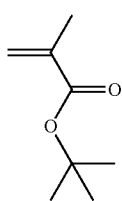

The obtained polymers A-1 to A-4 were described below.

Regarding the obtained polymers, the copolymer composition ratio (the ratio of each of the structural units (molar ratio) in the polymer) was obtained by $^{13}$C-NMR. In addition, the mass average molecular weight (Mw) and the molecular weight dispersivity (Mw/Mn) were obtained by GPC measurement in terms of standard polystyrene.

A-1
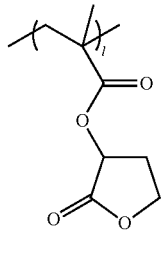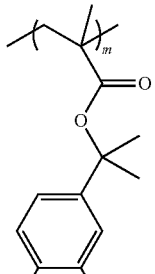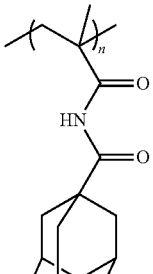

A-2
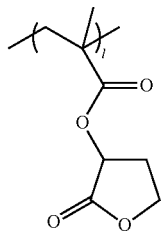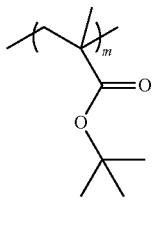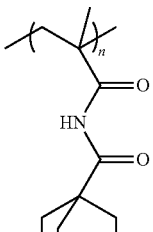

Polymer A-1:
Copolymer composition ratio: l/m/n=45/30/25
Mass average molecular weight (Mw): 8100
Molecular weight dispersivity (Mw/Mn): 1.74
Polymer A-2:
Copolymer composition ratio: l/m/n=45/30/25
Mass average molecular weight (Mw): 7700
Molecular weight dispersivity (Mw/Mn): 1.76

A-3
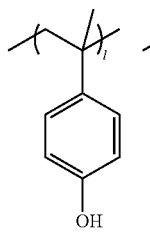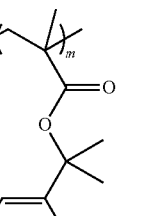

A-4
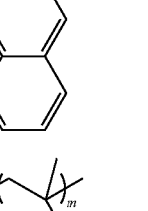

Polymer A-3:
Copolymer composition ratio: l/m=60/40
Mass average molecular weight (Mw): 6800
Molecular weight dispersivity (Mw/Mn): 1.64

Polymer A-4:
Copolymer composition ratio: l/m=60/40
Mass average molecular weight (Mw): 5800
Molecular weight dispersivity (Mw/Mn): 1.53

Preparation Examples of Compounds

Synthesis Example 1

Oxalyl chloride (6.15 g) and dimethyl formamide (0.03 g) were added dropwise to a mixture of dehydrocholic acid (15.0 g) and dichloromethane (135 g), and the resultant was stirred at room temperature for 3 hours. The obtained reaction solution was concentrated, thereby obtaining a compound (15.6 g) represented by general formula (a).

Identification of the compound represented by general formula (a) obtained by the above synthesis will be described below.

$^1$H-NMR (DMSO-d$^6$) δ (ppm)=3.02-2.80 (m, 5H) 2.39-1.80 (m, 14H), 1.66-1.53 (m, 1H), 1.52-1.21 (m, 7H), 1.07 (S, 3H), 0.86 (d, 3H)

Synthesis Example 2

A compound (11.5 g) represented by general formula (a), acetonitrile (105 g), and a salt (9.92 g) and triethylamine (2.63 g) represented by general formula (b) were mixed and stirred at room temperature for 24 hours. The obtained reaction solution was filtered and concentrated. The obtained residue was dissolved in tetrahydrofuran (hereinafter referred to as "THF") (100 g), then t-butyl methyl ether (50.0 g) was added dropwise thereto to thereby precipitate a white solid. Thereafter, the solvent was removed by decantation, and a white solid was collected. After dissolving the white solid in THF (100 g), t-butyl methyl ether (50.0 g) was added dropwise to the resulting solution to thereby precipitate a white solid. The same operation was repeated four times so as to obtain a white solid, then the white solid, dichloromethane (95.0 g), and ion exchanged water (50.0 g) were added and stirred at room temperature for 30 minutes, and then liquid separation was performed so as to collect an organic layer. Ion exchanged water (50.0 g) was added to the collected organic layer, and the mixture was stirred at room temperature for 30 minutes, and then separated, thereby collecting the organic layer. This washing operation was repeated twice. The obtained organic layer was concentrated, thereby obtaining a salt (3.40 g) represented by general formula (c).

Identification of the compound represented by general formula (c) obtained by the above synthesis will be described below.

$^1$H-NMR (DMSO-d$^6$) δ (ppm)=8.82 (s, 1H), 4.50-4.40 (m, 2H), 4.30-4.20 (m, 2H), 3.15-2.95 (m, 8H), 2.84 (t, 1H), 2.55-1.64 (m, 16H), 1.55-1.45 (m, 1H), 1.33-1.05 (m, 16H), 1.01 (s, 3H), and 0.75 (d, 3H)

$^{19}$F-NMR (DMSO-d$^6$) δ (ppm)=−106.8 (t, 2F)

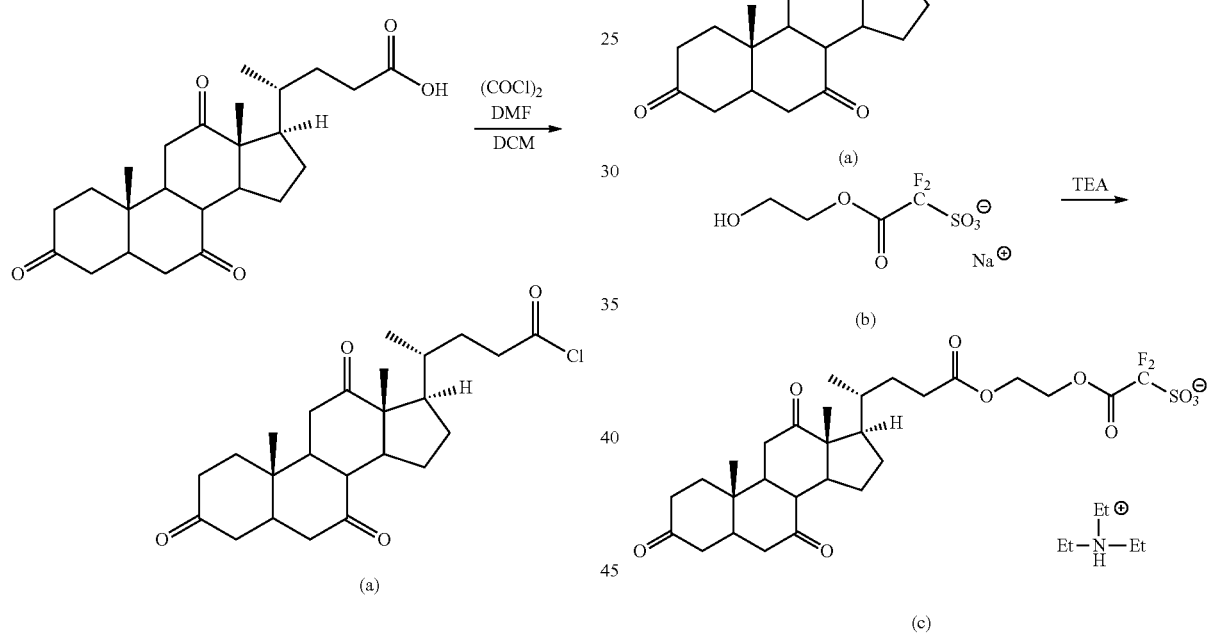

Synthesis Example 3

The salt (14.0 g) represented by general formula (c), the salt (9.88 g) represented by general formula (d), dichloromethane (186 g), and ion exchanged water (88.9 g) were mixed, and stirred for 30 minutes at room temperature, and then liquid separation was performed so as to collect an organic layer. Ion exchanged water (186 g) was added to the collected organic layer, and the mixture was stirred at room temperature for 30 minutes, and then separated, thereby collecting the organic layer. This washing operation was repeated three times. The obtained organic layer was concentrated, thereby obtaining a salt (14.9 g) represented by general formula (e).

Identification of the compound represented by general formula (e) obtained by the above synthesis will be described below.

$^1$H-NMR (DMSO-d$^6$) δ (ppm)=7.77-7.98 (m, Ph, 11H), 4.50-4.40 (m, 2H), 3.15-2.95 (m, 4H), 2.55-1.64 (m, 16H), 1.55-1.55-1.05 (m, 12H), 0.75 (d, 3H)
$^{19}$F-NMR (DMSO-d$^6$) δ (ppm)=−101.2 (s, 2F), −106.8 (t, 2F)

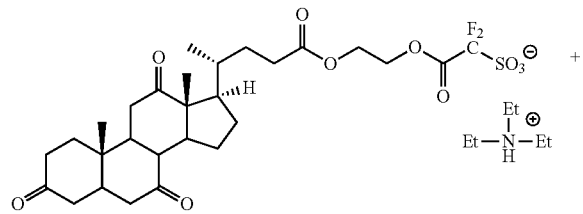

Preparation of Resist Compositions

Examples 1 to 11, Comparative Examples 1 to 13

The components indicated in Tables 1 and 2 were mixed and dissolved to prepare each resist composition.

TABLE 1

|  | (A) Component | | (B1) Component | (D) Component | (S) Component |
|---|---|---|---|---|---|
| Example 1 | (A)-1 [50] | (A)-3 [50] | (B1)-1 [16.0] | (D)-1 [3.0] | (S)-1 [6000] |
| Example 2 | (A)-1 [50] | (A)-3 [50] | (B1)-2 [22.8] | (D)-1 [3.0] | (S)-1 [6000] |
| Example 3 | (A)-1 [50] | (A)-3 [50] | (B1)-3 [21.4] | (D)-1 [3.0] | (S)-1 [6000] |
| Example 4 | (A)-1 [50] | (A)-3 [50] | (B1)-4 [14.2] | (D)-1 [3.0] | (S)-1 [6000] |
| Example 5 | (A)-1 [50] | (A)-3 [50] | (B1)-5 [14.6] | (D)-1 [3.0] | (S)-1 [6000] |
| Example 6 | (A)-1 [50] | (A)-3 [50] | (B1)-6 [15.9] | (D)-1 [3.0] | (S)-1 [6000] |
| Example 7 | (A)-1 [50] | (A)-3 [50] | (B1)-7 [14.2] | (D)-1 [3.0] | (S)-1 [6000] |
| Example 8 | (A)-1 [50] | (A)-3 [50] | (B1)-8 [15.1] | (D)-1 [3.0] | (S)-1 [6000] |
| Example 9 | (A)-1 [50] | (A)-3 [50] | (B1)-9 [15.8] | (D)-1 [3.0] | (S)-1 [6000] |
| Example 10 | (A)-1 [50] | (A)-3 [50] | (B1)-10 [18.7] | (D)-1 [3.0] | (S)-1 [6000] |
| Example 11 | (A)-1 [50] | (A)-3 [50] | (B1)-11 [20.6] | (D)-1 [3.0] | (S)-1 [6000] |

TABLE 2

|  | (A) Component | (B1) Component | (B2) Component | (D) Component | (S) Component |
|---|---|---|---|---|---|
| Comparative Example 1 | (A)-2 [50] | (A)-4 [50] | — | (B2)-1 [11.7] | (D)-1 [3.0] | (S)-1 [6000] |
| Comparative Example 2 | (A)-2 [50] | (A)-4 [50] | — | (B2)-1 [11.7] | (D)-1 [3.0] | (S)-1 [6000] |
| Comparative Example 3 | (A)-2 [50] | (A)-4 [50] | (B1)-1 [16.0] | — | (D)-1 [3.0] | (S)-1 [6000] |
| Comparative Example 4 | (A)-2 [50] | (A)-4 [50] | (B1)-2 [22.8] | — | (D)-1 [3.0] | (S)-1 [6000] |
| Comparative Example 5 | (A)-2 [50] | (A)-4 [50] | (B1)-3 [21.4] | — | (D)-1 [3.0] | (S)-1 [6000] |
| Comparative Example 6 | (A)-2 [50] | (A)-4 [50] | — | (B2)-2 [10.0] | (D)-1 [3.0] | (S)-1 [6000] |
| Comparative Example 7 | (A)-2 [50] | (A)-4 [50] | — | (B2)-3 [10.4] | (D)-1 [3.0] | (S)-1 [6000] |
| Comparative Example 8 | (A)-2 [50] | (A)-4 [50] | — | (B2)-4 [11.6] | (D)-1 [3.0] | (S)-1 [6000] |
| Comparative Example 9 | (A)-2 [50] | (A)-4 [50] | — | (B2)-5 [9.9] | (D)-1 [3.0] | (S)-1 [6000] |
| Comparative Example 10 | (A)-2 [50] | (A)-4 [50] | — | (B2)-6 [10.8] | (D)-1 [3.0] | (S)-1 [6000] |
| Comparative Example 11 | (A)-2 [50] | (A)-4 [50] | — | (B2)-7 [11.6] | (D)-1 [3.0] | (S)-1 [6000] |
| Comparative Example 12 | (A)-2 [50] | (A)-4 [50] | — | (B2)-8 [14.5] | (D)-1 [3.0] | (S)-1 [6000] |

TABLE 2-continued

| | (A) Component | (B1) Component | (B2) Component | (D) Component | (S) Component |
|---|---|---|---|---|---|
| Comparative Example 13 | (A)-2 [50] | (A)-4 [50] | (B2)-9 [16.4] | (D)-1 [3.0] | (S)-1 [6000] |

Each abbreviation in Tables 1 and 2 has the following meaning. In addition, the numerical value in brackets is the compounding amount (parts by mass).

(A)-1: polymer A-1
(A)-2: polymer A-2
(A)-3: polymer A-3
(A)-4: polymer A-4
(B1)-1: compound represented by chemical formula (B1)-1
(B1)-2: compound represented by chemical formula (B1)-2
(B1)-3: compound represented by chemical formula (B1)-3
(B1)-4: compound represented by chemical formula (B1)-4
(B1)-5: compound represented by chemical formula (B1)-5
(B1)-6: compound represented by chemical formula (B1)-6
(B1)-7: compound represented by chemical formula (B1)-7
(B1)-8: compound represented by chemical formula (B1)-8
(B1)-9: compound represented by chemical formula (B1)-9
(B1)-10: compound represented by chemical formula (B1)-10
(B1)-11: compound represented by chemical formula (B1)-11

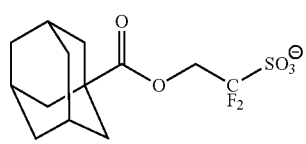
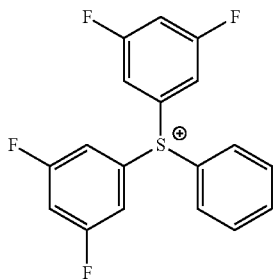

(B1)-1

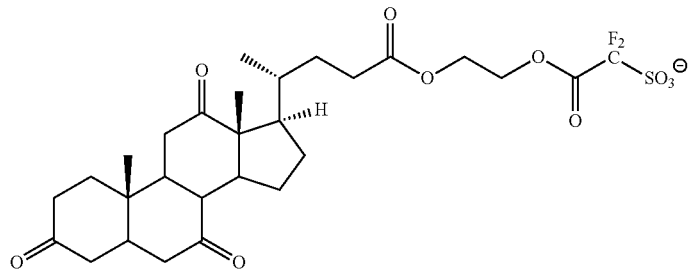
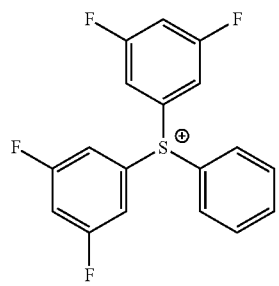

(B1)-2

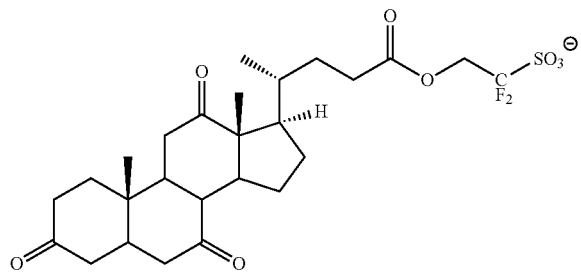
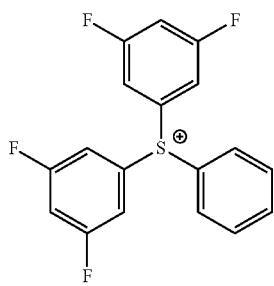

(B1)-3

-continued

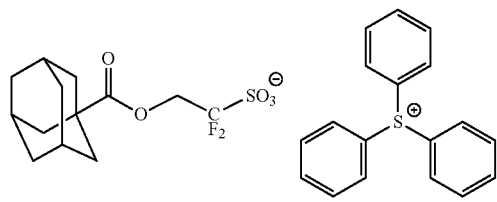
(B1)-4

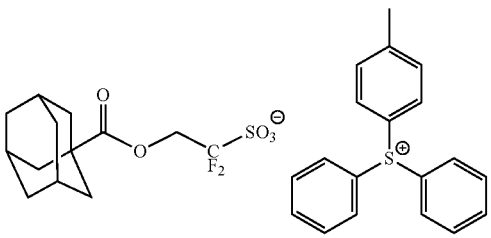
(B1)-5

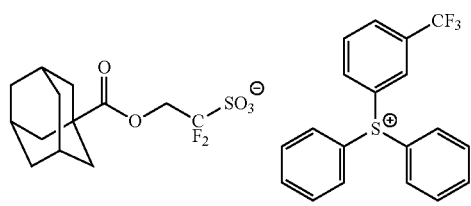
(B1)-6

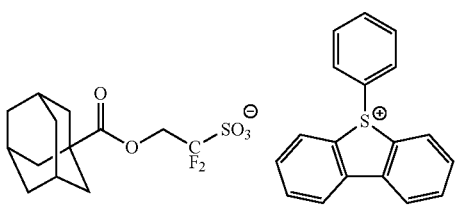
(B1)-7

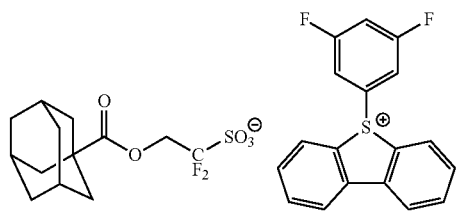
(B1)-8

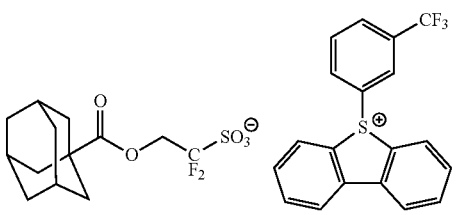
(B1)-9

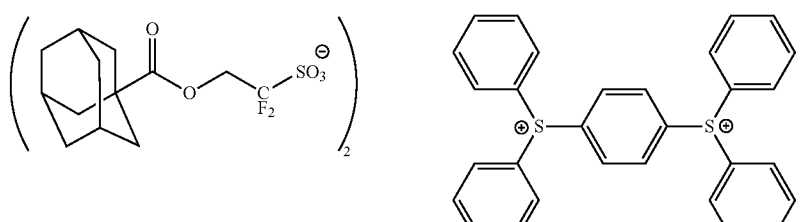
(B1)-10

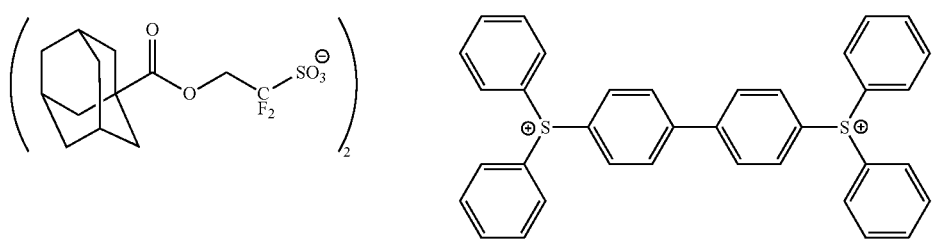
(B1)-11

(B2)-1: compound represented by chemical formula (B2)-1
(B2)-2: compound represented by chemical formula (B2)-2
(B2)-3: compound represented by chemical formula (B2)-3
(B2)-4: compound represented by chemical formula (B2)-4
(B2)-5: compound represented by chemical formula (B2)-5
(B2)-6: compound represented by chemical formula (B2)-6
(B2)-7: compound represented by chemical formula (B2)-7
(B2)-8: compound represented by chemical formula (B2)-8
(B2)-9: compound represented by chemical formula (B2)-9

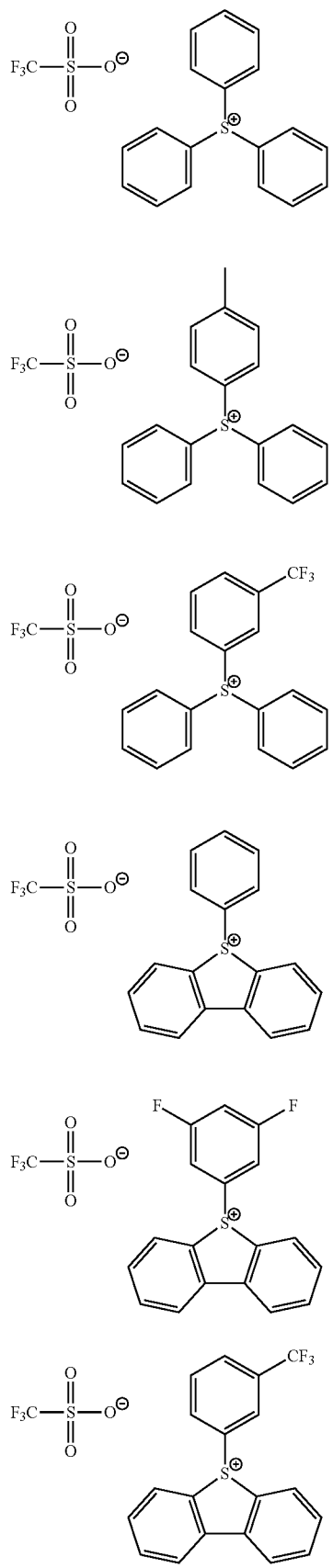

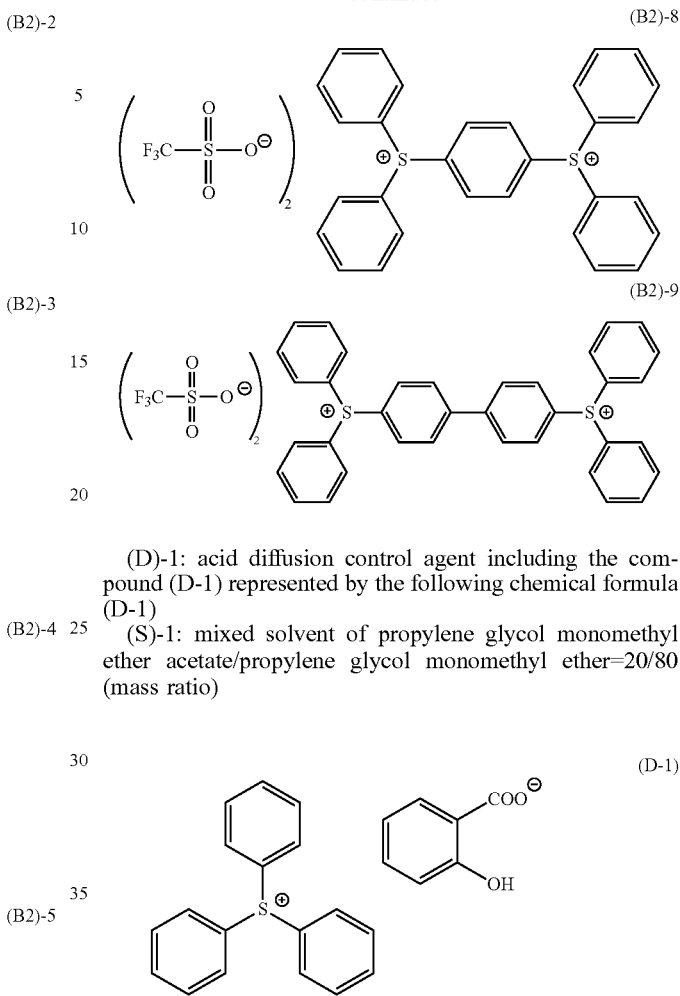

(D)-1: acid diffusion control agent including the compound (D-1) represented by the following chemical formula (D-1)

(S)-1: mixed solvent of propylene glycol monomethyl ether acetate/propylene glycol monomethyl ether=20/80 (mass ratio)

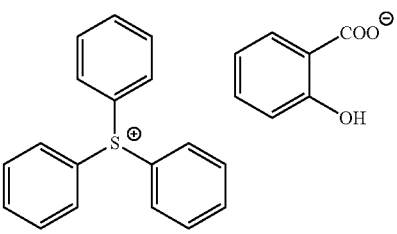

Formation of Resist Pattern

An 8-inch silicon substrate treated with hexamethyldisilazane (HMDS) was coated with the resist composition of each example with a spinner, was subjected to a pre-baking (PAB) treatment at 110° C. for 60 seconds on a hot plate, and was dried to thereby form a resist film having a film thickness of 30 nm.

Next, on the resist film, lithography (exposure) was performed using an electron beam drawing apparatus JEOL-JBX-9300FS (manufactured by JEOL Ltd.) at an acceleration voltage of 100 kV setting a 1:1 line and space pattern (hereinafter, referred to as an "LS pattern") having a line width of 50 to 16 nm as a target size. Thereafter, a post exposure bake (PEB) treatment was performed at 110° C. for 60 seconds.

Then, the resist film was subjected to an alkaline developing at 23° C. for 60 seconds with an aqueous solution containing 2.38% by mass of tetramethyl ammonium hydroxide (TMAH) "NMD-3" (product name, prepared by Tokyo Ohka Kogyo Co., Ltd).

Thereafter, water rinsing was performed for 60 seconds with pure water.

As a result, a 1:1 LS pattern having a line width of 50 to 16 nm was formed.

Evaluation of Optimal Exposure Amount (Eop)

The optimum exposure dose (μC/cm²) at which the LS pattern having a target size was formed was obtained according to the above resist pattern forming method, and was shown as "Eop (μC/cm$^2$)" in Table 3.

Evaluation of Resolution

The limit resolution at the Eop, specifically, when the LS pattern is formed by gradually increasing the exposure amount from the optimum exposure amount Eop, the minimum dimension of the pattern resolved without collapse was measured by a scanning electron microscope S-9380 (manufactured by Hitachi High-Technologies Corporation), and was shown as "resolution performance (nm)" in Table 3.

Evaluation of Line-Width Roughness (LWR)

Regarding the LS pattern formed by the above "Forming of resist pattern", 3σ which is a scale indicating LWR was obtained, and was shown as "LWR (nm)" in Table 3.

"3σ" (unit: nm) indicates three times the value of the standard deviation (σ) obtained from the result of the measurement performed by measuring a line width at each of 400 positions in the longitudinal direction of the line with a scanning electron microscope (acceleration voltage of 800 V, product name: S-9380, manufactured by Hitachi High-Technologies Corporation).

It means that as the value of 3σ is small, the roughness of the line side wall is small, thereby obtaining the LS pattern having more uniform width.

Evaluation of LS Pattern Shape

The shape of the LS pattern formed by the above "Formation of resist pattern" was observed with a scanning electron microscope (SEM, acceleration voltage of 800 V, product name: SU-8000, manufactured by Hitachi High-Technologies Corporation), and was shown as "shape" in Table 3.

What is claimed is:

1. A resist composition which generates an acid upon exposure and whose solubility in a developing solution changes under an action of the acid, the resist composition comprising:

a base material component (A) whose solubility in a developing solution changes under the action of an acid and which contains a resin component (A1) having a structural unit (a0) represented by general formula (a0-1) and a structural unit (a9) represented by general formula (a9-1):

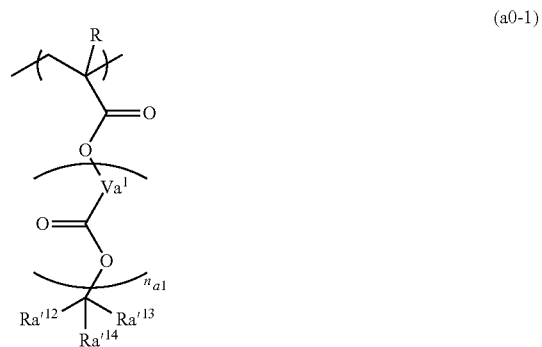

(a0-1)

wherein, R represents a hydrogen atom, an alkyl group having 1 to 5 carbon atoms, or a halogenated alkyl group having 1 to 5 carbon atoms, Va$^1$ is a divalent hydrocarbon group which may have an ether bond, $n_{a1}$ represents an integer of 0 to 2, Ra$'^{12}$ and Ra$'^{13}$ each independently represent a monovalent chain saturated hydrocarbon group having 1 to 10 carbon atoms or a

TABLE 3

| | PAB (° C.) | PEB (° C.) | Eop (μC/cm$^2$) | Resolution performance (nm) | LWR (nm) | Shape |
|---|---|---|---|---|---|---|
| Example 1 | 110 | 110 | 80 | 26 | 4.2 | Rectangular shape |
| Example 2 | 110 | 110 | 85 | 26 | 4.3 | Rectangular shape |
| Example 3 | 110 | 110 | 85 | 24 | 4.2 | Rectangular shape |
| Example 4 | 110 | 110 | 95 | 26 | 4.6 | Rectangular shape |
| Example 5 | 110 | 110 | 90 | 28 | 4.5 | Rectangular shape |
| Example 6 | 110 | 110 | 85 | 24 | 4.3 | Rectangular shape |
| Example 7 | 110 | 110 | 90 | 26 | 4.4 | Rectangular shape |
| Example 8 | 110 | 110 | 90 | 26 | 4.5 | Rectangular shape |
| Example 9 | 110 | 110 | 85 | 24 | 4.3 | Rectangular shape |
| Example 10 | 110 | 110 | 80 | 26 | 4.4 | Rectangular shape |
| Example 11 | 110 | 110 | 75 | 26 | 4.4 | Rectangular shape |
| Comparative Example 1 | 110 | 110 | 135 | 50 | 8.6 | Head-clad shape |
| Comparative Example 2 | 110 | 110 | 130 | 40 | 8.3 | Head-clad shape |
| Comparative Example 3 | 110 | 110 | 125 | 40 | 7.2 | Head-clad shape |
| Comparative Example 4 | 110 | 110 | 135 | 35 | 7.2 | Head-clad shape |
| Comparative Example 5 | 110 | 110 | 135 | 35 | 7.0 | Head-clad shape |
| Comparative Example 6 | 110 | 110 | 155 | 40 | 8.2 | Head-clad shape |
| Comparative Example 7 | 110 | 110 | 150 | 40 | 8.6 | Head-clad shape |
| Comparative Example 8 | 110 | 110 | 135 | 35 | 7.9 | Head-clad shape |
| Comparative Example 9 | 110 | 110 | 135 | 40 | 8.8 | Head-clad shape |
| Comparative Example 10 | 110 | 110 | 140 | 35 | 7.9 | Head-clad shape |
| Comparative Example 11 | 110 | 110 | 130 | 40 | 8.2 | Head-clad shape |
| Comparative Example 12 | 110 | 110 | 125 | 35 | 8.5 | Head-clad shape |
| Comparative Example 13 | 110 | 110 | 125 | 35 | 8.4 | Head-clad shape |

From the results shown in Table 3, according to the resist composition of the present embodiment to which the present invention is applied, in the forming of the resist pattern, it is possible to confirm that high sensitivity and improved lithography properties are realized and thus a resist pattern having an excellent shape can be formed.

hydrogen atom, at least one hydrogen atom of the chain saturated hydrocarbon group may be substituted, and Ra$'^{14}$ represents a phenyl group which may have a substituent, a naphthyl group which may have a substituent, or an anthryl group which may have a substituent;

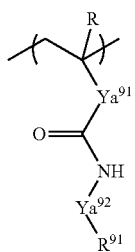

(a9-1)

wherein R is a hydrogen atom, an alkyl group having 1 to 5 carbon atoms, or a halogenated alkyl group having 1 to 5 carbon atoms, $Ya^{91}$ is a single bond or a divalent linking group, $Ya^{92}$ is a divalent linking group, and $R^{91}$ is a hydrocarbon group which may have a substituent; and an acid generator component (B) which generates an acid upon exposure and contains a compound (B1) represented by general formula (b1):

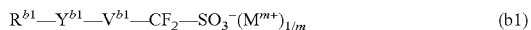

(b1)

wherein, $R^{b1}$ represents a cyclic hydrocarbon group which may have a substituent, $Y^{b1}$ represents a divalent linking group containing an ester bond (—C(=O)—O— or —O—C(=O)—), $V^{b1}$ represents an alkylene group, a fluorinated alkylene group, or a single bond, m is an integer of 1 or more, and $M^{m+}$ is an m-valent organic cation.

2. The resist composition according to claim 1, wherein a ratio of the structural unit (a0) in the resin component (A1) is 20 to 70 mol % with respect to a total of the entire structural units for constituting the resin component (A1).

3. The resist composition according to claim 1, wherein a content of the compound (B1) is 1 to 40 parts by mass with respect to 100 parts by mass of the base material component (A).

4. The resist composition according to claim 1, wherein the resin component (A1) further comprises a structural unit (a2) containing a lactone-containing cyclic group, an —SO$_2$— containing cyclic group, or a carbonate-containing cyclic group.

5. The resist composition according to claim 1, wherein the base material (A) further comprises a polymer compound (A1-1-2) having the structural unit (a0) which is different from the resin component (A1).

6. The resist composition according to claim 5, wherein the polymer compound (A1-1-2) further comprises the structural unit (a10) represented by general formula (a10-1):

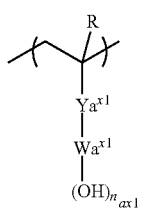

(a10-1)

wherein R represents a hydrogen atom, an alkyl group having 1 to 5 carbon atoms, or a halogenated alkyl group having 1 to 5 carbon atoms; $Ya^{x1}$ represents a single bond or a divalent linking group; $Wa^{x1}$ is a ($n_{ax1}$+1) valent aromatic hydrocarbon group; and $n_{ax1}$ is an integer 1 to 3.

7. The resist composition according to claim 6, wherein the base component (A) comprises:

the resin component (A1) having a repeated structure of the structural unit (a0), a structural unit (a2) containing a lactone-containing cyclic group, an —SO$_2$— containing cyclic group, or a carbonate-containing cyclic group, and the structural unit (a9); and the polymer compound (A1-1-2) having a repeated structure of the structural unit (a0) and the structural unit (a10).

8. The resist composition according to claim 5, wherein the resin component (A1) further comprises a structural unit (a2) containing a lactone-containing cyclic group, an —SO$_2$— containing cyclic group, or a carbonate-containing cyclic group.

9. A method for forming a resist pattern, comprising:
forming a resist film on a support by using the resist composition according to claim 1;
exposing the resist film; and
developing the exposed resist film to form a resist pattern.

10. The method for forming a resist pattern according to claim 9, wherein the resist film is exposed to extreme ultraviolet ray (EUV) or an electron beam (EB).

11. A resist composition which generates an acid upon exposure and whose solubility in a developing solution changes under an action of the acid, the resist composition comprising:

a base material component (A) whose solubility in a developing solution changes under the action of an acid and which contains a resin component (A1) having a structural unit (a0) represented by general formula (a0-1) and a structural unit (a10) represented by general formula (a10-1):

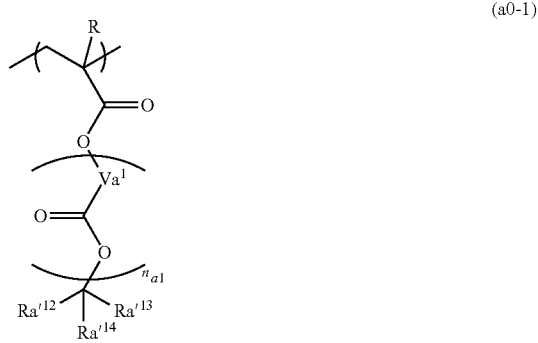

(a0-1)

wherein, R represents a hydrogen atom, an alkyl group having 1 to 5 carbon atoms, or a halogenated alkyl group having 1 to 5 carbon atoms, $Va^1$ is a divalent hydrocarbon group which may have an ether bond, $n_{a1}$ represents an integer of 0 to 2, $Ra'^{12}$ and $Ra'^{13}$ each independently represent a monovalent chain saturated hydrocarbon group having 1 to 10 carbon atoms or a hydrogen atom, at least one hydrogen atom of the chain saturated hydrocarbon group may be substituted, and Ra'^14 represents a phenyl group which may have a substituent, a naphthyl group which may have a substituent, or an anthryl group which may have a substituent,

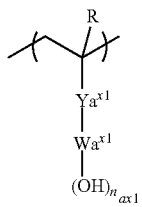

(a10-1)

wherein R represents a hydrogen atom, an alkyl group having 1 to 5 carbon atoms, or a halogenated alkyl group having 1 to 5 carbon atoms; $Ya^{x1}$ represents a single bond or a divalent linking group; $Wa^{x1}$ is a $(n_{ax1}+1)$ valent aromatic hydrocarbon group; and $n_{ax1}$ is an integer 1 to 3; and an acid generator component (B) which generates an acid upon exposure and contains a compound (B1) represented by general formula (b1):

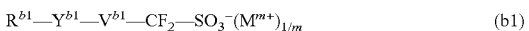

$$R^{b1}-Y^{b1}-V^{b1}-CF_2-SO_3^-(M^{m+})_{1/m} \quad (b1)$$

wherein, $R^{b1}$ represents a cyclic hydrocarbon group which may have a substituent, $Y^{b1}$ represents a divalent linking group containing an ester bond (—C(=O)—O— or —O—C(=O)—), $V^{b1}$ represents an alkylene group, a fluorinated alkylene group, or a single bond, m is an integer of 1 or more, and $M^{m+}$ is an m-valent organic cation.

12. The resist composition according to claim 11, wherein a ratio of the structural unit (a0) in the resin component (A1) is 20 to 70 mol % with respect to a total of the entire structural units for constituting the resin component (A1).

13. The resist composition according to claim 11, wherein a content of the compound (B1) is 1 to 40 parts by mass with respect to 100 parts by mass of the base material component (A).

* * * * *